(12) United States Patent
Grizot

(10) Patent No.: US 8,927,247 B2
(45) Date of Patent: Jan. 6, 2015

(54) I-CREI DERIVED SINGLE-CHAIN MEGANUCLEASE AND USES THEREOF

(75) Inventor: Sylvestre Grizot, La Garenne Colombes (FR)

(73) Assignee: Cellectis, S.A., Paris (FR)

( * ) Notice: Subject to any disclaimer, the term of this patent is extended or adjusted under 35 U.S.C. 154(b) by 943 days.

(21) Appl. No.: 12/864,998

(22) PCT Filed: Feb. 2, 2009

(86) PCT No.: PCT/IB2009/000439
§ 371 (c)(1),
(2), (4) Date: Mar. 22, 2011

(87) PCT Pub. No.: WO2009/095793
PCT Pub. Date: Aug. 6, 2009

(65) Prior Publication Data
US 2011/0179506 A1  Jul. 21, 2011

Related U.S. Application Data

(63) Continuation-in-part of application No. PCT/IB2008/001331, filed on Jan. 31, 2008.

(51) Int. Cl.
C12N 9/16 (2006.01)
C07K 14/00 (2006.01)
C12N 9/22 (2006.01)

(52) U.S. Cl.
CPC .............. *C12N 9/22* (2013.01); *C07K 2319/00* (2013.01)
USPC ............................ 435/196; 435/195; 530/350

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 5,006,333 | A | 4/1991 | Saifer et al. |
| 5,272,071 | A | 12/1993 | Chappel |
| 5,436,150 | A | 7/1995 | Chandrasegaran |
| 5,474,896 | A | 12/1995 | Dujon et al. |
| 5,641,670 | A | 6/1997 | Treco et al. |
| 5,792,632 | A | 8/1998 | Dujon et al. |
| 5,801,030 | A | 9/1998 | McVey et al. |
| 5,830,729 | A | 11/1998 | Jaisser et al. |
| 5,843,701 | A | 12/1998 | Gold et al. |
| 5,866,361 | A | 2/1999 | Dujon et al. |
| 5,948,678 | A | 9/1999 | Dujon et al. |
| 5,962,327 | A | 10/1999 | Dujon et al. |
| 6,037,162 | A | 3/2000 | Raveh |
| 6,063,630 | A | 5/2000 | Treco et al. |
| 6,172,188 | B1 | 1/2001 | Thastrup et al. |
| 6,232,112 | B1 | 5/2001 | Catcheside |
| 6,238,924 | B1 | 5/2001 | Dujon et al. |
| 6,395,959 | B1 | 5/2002 | Dujon et al. |
| 6,528,313 | B1 | 3/2003 | Le Mouellic et al. |
| 6,528,314 | B1 | 3/2003 | Le Mouellic et al. |
| 6,610,545 | B2 | 8/2003 | Dujon et al. |
| 7,309,605 | B1 | 12/2007 | Dujon et al. |
| 7,462,758 | B2 | 12/2008 | Biesgen |
| 7,842,489 | B2 | 11/2010 | Arnould et al. |
| 7,897,372 | B2 | 3/2011 | Duchateau et al. |
| 8,021,867 | B2 | 9/2011 | Smith et al. |
| 2003/0096249 | A1 | 5/2003 | Westphal et al. |
| 2003/0228583 | A1 | 12/2003 | Amacher et al. |
| 2004/0002092 | A1 | 1/2004 | Arnould et al. |
| 2004/0019916 | A1 | 1/2004 | Zarling et al. |
| 2004/0203153 | A1 | 10/2004 | Le Mouellic et al. |
| 2005/0064474 | A1 | 3/2005 | Urnov et al. |
| 2005/0172365 | A1 | 8/2005 | Puchta et al. |
| 2006/0206949 | A1 | 9/2006 | Arnould et al. |

FOREIGN PATENT DOCUMENTS

| | | |
|---|---|---|
| EP | 419621 A1 | 4/1991 |
| WO | 9117271 | 11/1991 |
| WO | 9118980 | 12/1991 |
| WO | 9119818 | 12/1991 |
| WO | 9308278 | 4/1993 |
| WO | 9418313 | 8/1994 |
| WO | 9509233 | 4/1995 |
| WO | 9614408 | 5/1996 |
| WO | 0046385 A1 | 8/2000 |
| WO | 0046386 A2 | 8/2000 |
| WO | 0047775 A1 | 8/2000 |
| WO | 0170946 A2 | 9/2001 |
| WO | 0242497 A2 | 5/2002 |
| WO | 02/099105 A2 | 12/2002 |
| WO | 03078619 A1 | 9/2003 |
| WO | 2004/031346 A2 | 4/2004 |
| WO | 2004067736 A2 | 8/2004 |
| WO | 2006/097784 A1 | 9/2006 |
| WO | 2006/097853 A1 | 9/2006 |
| WO | 2006/097854 A1 | 9/2006 |
| WO | 2007/034262 A1 | 3/2007 |
| WO | 2007/047859 A2 | 4/2007 |

(Continued)

OTHER PUBLICATIONS

Office Action from U.S. Appl. No. 11/908,934, mailed Oct. 14, 2010, and Jan. 25, 2010.

(Continued)

*Primary Examiner* — Richard Hutson
(74) *Attorney, Agent, or Firm* — Kenyon & Kenyon LLP

(57) ABSTRACT

A new I-CreI derived single-chain meganuclease comprising two domains, each domain comprising a portion of a parent I-CreI monomer which extends at least from the beginning of the first alpha helix to the end of the C-terminal loop and said two domains being joined by a peptidic linker which allows them to fold as a I-CreI dimer that is able to bind and cleave a chimeric DNA target comprising one different half of each parent homodimeric I-CreI meganuclease target sequence. Use of said I-CreI derived single-chain meganuclease for genetic engineering, genome therapy and antiviral therapy.

10 Claims, 29 Drawing Sheets

(56) References Cited

FOREIGN PATENT DOCUMENTS

| WO | 2007/049095 A1 | 5/2007 |
| WO | 2007/049156 A2 | 5/2007 |
| WO | 2007/057781 A2 | 5/2007 |
| WO | 2007/060495 A1 | 5/2007 |
| WO | 2007/093836 A1 | 8/2007 |
| WO | 2007/093918 A1 | 8/2007 |
| WO | 2008/002198 A1 | 1/2008 |
| WO | 2008/002199 A2 | 1/2008 |
| WO | 2008/002274 A1 | 1/2008 |
| WO | 2008/010009 A1 | 1/2008 |
| WO | 2008/010093 A2 | 1/2008 |
| WO | 2008/059317 A1 | 5/2008 |
| WO | 2008/059382 A2 | 5/2008 |
| WO | 2008/093152 A1 | 8/2008 |
| WO | 2008/093249 A2 | 8/2008 |
| WO | 2008/015253 A1 | 12/2008 |
| WO | 2008/149176 A1 | 12/2008 |
| WO | 2008/152524 A2 | 12/2008 |
| WO | 2009/059195 A2 | 5/2009 |
| WO | 2009/095742 A1 | 8/2009 |
| WO | 2009/095793 A1 | 8/2009 |
| WO | 2010/026443 A1 | 3/2010 |
| WO | 2004/067753 A2 | 8/2012 |

OTHER PUBLICATIONS

Office Action from U.S. Appl. No. 10/388,230 mailed Jul. 14, 2011; Nov. 15, 2010; May 24, 2010; Nov. 25, 2008; Jun. 14, 2007; and Feb. 9, 2006.

Office Action from U.S. Appl. No. 10/507,736, mailed Jan. 27, 2011; Jun. 25, 2010; Aug. 5, 2009, and Aug. 1, 2008.

Notice of Opposition to a European Patent No. 1 485 475, dated Jun. 5, 2008.

Summons to Attend Oral Proceedings issued for European Patent No. 1 485475, dated Jun. 30, 2009.

Response to Summons to Attend Oral Proceedings for European Patent No. 1 485475, filed Sep. 18, 2009.

Response to Opposition to European Patent No. 1 485475, filed Jan. 13, 2009.

Response to Oral Proceedings to European Patent No. 1 485475, received Jun. 30, 2009, filed Sep. 18, 2009.

Appeal filed for European Patent No. 1 485475, filed Jun. 8, 2010. (French).

Appeal filed for European Patent No. 1 485475, filed Jun. 17, 2010.

Sussman et al., "Isolation and characterization of new homing endonuclease specificities at individual target site positions," (2004) J. Mol. Biol. 342:31-41.

Arnould et al., "Engineered I-CreI derivatives cleaving sequences from the human XPC gene can induce highly efficient gene correction in mammalian cells," J. Mol Biol, (2007) vol. 371, pp. 49-65.

Ashworth et al., "Computational redesign of endonucleases DNA binding and cleavage specificity," Nature, (2006), vol. 441, pp. 656-659.

Belfort et al., "Homing endonucleases: keeping the house in order," Nucleic Acids Res, , (1997), vol. 25, pp. 3379-3388.

Bolduc et al., "Structural and biochemical analyses of DNA and RNA binding by a bifunctional homing endonuclease and group I intron splicing factor," Genes Dev, (2003), vol. 17, pp. 2875-2888.

Chen, "Enzyme engineering: rational redesign versus directed evolution," Trends Biotechnol, (2001), vol. 19, pp. 13-14.

Chen et al., "Directed evolution of homing endonuclease I-SceI with altered sequence specificity," Protein Eng Des Sel, (2009), vol. 22, pp. 249-256.

Chevalier et al, "Flexible DNA Target Site Recognition by Divergent Homing Endonuclease Isoschizomers I-CreI and I-MsoI," J Mol. Biol. (2003), vol. 329, pp. 253-269.

Doyon et al., "Directed evolution and substrate specificity profile of homing endonuclease I-SceI," J Am Chem Soc, (2006), vol. 128, pp. 2477-2484.

Durai et al., "Zinc finger nucleases: custom-designed molecular scissors for genome engineering of plant and mammalian cells," Nucleic Acids Res. (2005), vol. 33, pp. 5978-5990.

Edgell et al, "Barriers to intron promiscuity in bacteria," J Bacteriol (2000), vol. 182, pp. 5281-5289.

Edgell, "Selfish DNA: homing endonucleases find a home," Curr Bioi, (2009) vol. 19, pp. R115-R117.

Eklund et al., "Altered target site specificity variants of the I-Ppol His-Cys box homing endonuclease," Nucleic Acids Res. (2007), vol. 35, pp. 5839-5850.

Fajardo-Sanchez et al., "Computer design of obligate heterodimer meganucleases allows efficient cutting of custom DNA sequences," Nucleic Acids Res. (2008), vol. 36(7), pp. 2163-2173.

Flick et al., "DNA binding and cleavage by the nuclear intron-encoded homing endonuclease I-Ppol," Nature, (1998), vol. 394, pp. 96-101.

Gimble et al., "Assessing the plasticity of DNA target site recognition of the PI-SceI homing endonuclease using a bacterial two-hybrid selection system," J Mol Biol, (2003) vol. 334, pp. 993-1008.

Gimble, "Engineering Homing Endonulceases for Genomic Applications," in Homing Endonucleases and Inteins, (2005), Belfort, Derbyshire, Stoddard and Woods, Eds. Springer-Verlag, Berlin Heidelberg [Table of Contents Only].

Grizot et al., "Efficient targeting of a SCID gene by an engineered single-chain homing endonuclease," Nucleic Acids Res, (2009a), vol. 37, pp. 5405-5419.

Grizot et al., "Generation of redesigned homing endonucleases comprising DNA-binding domains derived from two different scaffolds," Nucleic Acids Res, (2009b) 1-13; doi:l0.1093/nar/gkpl171, published on-line on Dec. 21, 2009.

Harris et al., "Engineering enzyme specificity," Curr Opin Chem Biol. (1998), vol. 2, pp. 127-132.

Koufopanou et al., "Adaptation for horizontal transfer in a homing endonuclease," Mol Biol. Evol, (2002), vol. 19, pp. 239-246.

Li et al., "Generation of single-chain Laglidadg homing endonucleases from native homodimeric precursor proteins," Nucleic Acids Res, (2009), vol. 37, pp. 1650-1662.

Loizos et al., "Evolution of mobile group I introns: recognition of intron sequences by an intron-encoded endonuclease," Proc Natl Acad Sci USA, (1994), vol. 91, pp. 11983-11987.

Loizos et al., "Intron-encoded endonuclease I-TevII binds across the minor groove and induces two distinct conformational changes in its DNA substrate," J Mol Biol, (1996), vol. 255, pp. 412-424.

Lucas et al., "Rapid evolution of the DNA-binding site in LAGLIDADG homing endonucleases," Nucleic Acids Res (2001), vol. 29, pp. 960-969.

Matsumura et al., "Crystal structure of intein homing endonuclease II encoded in DNA polymerase gene from hyperthermophilic archaeon Thermococcus kodakaraensis strain KOD1," Proteins, (2006), vol. 63, pp. 711-715.

Monnat et al., "Generation of Highly Site-Specific DNA Double-Strand Break in Human Cells by the Homing Endonucleases I-Ppol and I-CreI," Biochem Biophys Res Commun, (1999), vol. 255, pp. 88-93.

Moure et al., "Crystal structure of the intein homing endonuclease PI-SceI bound to its recognition sequence," Nat Struct Biol. (2002), vol. 9, pp. 764-770.

Moure et al., "The crystal structure of the gene targeting homing endonuclease I-SceI reveals the origins of its target site specificity," J. Mol Biol. , (2003), vol. 334, pp. 685-695.

Nakayama et al., "Structure of a hyperthermophilic archaeal homing endonuclease, I-Tsp06II: contribution of cross-domain polar networks to thermostability," J Mol Biol. (2007), vol. 365, pp. 362-378.

Ngo, et al., "The protein folding problem and tertiary structure prediction," (1994), Merz et al. (ed.) Birkhauser, Boston, MA pp. 433 and 492-495.

Nomura et al. "Recognition of a common rDNA target site in archaea and eukarya by analogous LAGLIDADG and His-Cys box homing endonucleases," Nucleic Acids Res (2008), vol. 36, pp. 6988-6998.

Prieto et al., "The C-tenninal loop of the homing endonuclease I-CreI is essential for site recognition, DNA binding and cleavage," Nucleic Acids Res (2007), vol. 35, pp. 3262-3271.

(56) References Cited

OTHER PUBLICATIONS

Roberts et al., "REBASE—enzymes and genes for DNA restriction and modification," Nucleic Acids Res , (2007), vol. 35, pp. D269-D270.
Rochaix et al., "The chloroplast ribosomal intron of Chlamydomonas reinhardtii codes for a polypeptide related to mitochondrial maturases," Nucleic Acids Res, (1985), vol. 13, pp. 975-984.
Redondo et al., "Molecular basis of xeroderma pigmentosum group C DNA recognition by engineered meganucleases," Nature (2008), vol. 456, pp. 107-111.
Rosen et al., "Homing endonuclease I-CreI derivatives with novel DNA target specificities," Nucleic Acids Res, (2006), vol. 34, pp. 4791-4800.
Scalley-Kim et al., "Coevolution of a homing endonuclease and its host target sequence," J Mol Biol. (2007) , vol. 372, pp. 1305-1319.
Seligman et al., "Genetic analysis of the Chlamydomonas reinhardtii I-CreI mobile intron homing system in *Escherichia coli*," Genetics(1997) , vol. 147, pp. 1653-1664.
Chevalier, B. S. et al, "The Homing Endonuclease I-CreI Uses Three Metals, One of Which is Shared Between the Two Active Sites," Nat Struct Biol, 8:312-316 (2001).
Perbal, B., A Practical Guide to Molecular Cloning, John Wiley & Sons, New York. Table of Content (1984).
Pabo, C. O. et al., "Design and Selection of Novel CYS2 HIS2 Zinc Finger Proteins," Annu. Rev. Biochem., 70: 313-340 (2001).
Moure, C. M. et al., "The Crystal Structure of the Gene Targeting Homing Endonuclease I-SceI Reveals the Origins of its Target Site Specificity," Mol. Biol, 334: 685-695 (2003).
Moure, C. M. et al., "Crystal Structure of the Intein Homing Endonuclease PI-SceI Bound to its Recognition Sequence," Nat. Struc. Biol., 9: 764-770 (2002).
Choo, Y. et al., "Toward a code for the interactions of zinc fingers with DNA: Selection of randomized fingers displayed on phage", Proc. Natl. Acad. Sci., 91: 11163-11167 (1994).
Miller, J. H. et al., Gene Transfer Vectors for Mammalian Cells, Cold Spring Harbor Laboratory. Table of Content (1987).
Coffin, J. M., Retroviridae: The viruses and their replication, in Fundamental Virology, Third Ed. B.N. Fields, et al., Eds., Lippincott-Raven Publishers, Philadelphia (1996).
Mayer, R. J. et al., Immunochemical Methods in Cell and Molecular Biology, Academic Press, London. Table of Content (1987).
Maeder, M. L. et al., "Rapid 'Open-Source' Engineering of Customized Zinc-Finger Nucleases for Highly Efficient Gene Modification", Mol. Cell, 31:294-301.
Doyon, J. B. et al., "Directed Evolution and Substrate Specificity Profile of Homing Endonuclease I-SceI". J. Am. Chem. Soc., 128: No. 7, 2477-2484 (2006).
Paques et al., "Meganucleases and DNA Double-Strand Break-Induced Recombination: Perspectives for Gene Therapy," Current Gene Therapy, 7: 49-66 (2007).
Perrin et al., "Asymmetrical Recognition and Activity of the I-SceI Endonuclease on its Site and on Intron-exon Junctions," Embo J, 12: 2939-2947 (1993).
Pfeifer et al., "Transduction of Liver Cells by Lentiviral Vectors: Analysis in Living Animals by Fluorescence Imaging", Molecular Therapy, vol. 3, No. 3 (2001).
Philpott et al., "Viral Vectors for Gene Therapy," Encyclopedia of Life Sciences, 1-6 (2007).
Plaintiff Cellectis's Brief in Support of its Proposed Claim Construction, Nov. 2, 2009.
Plessis et al., "Site-Specific Recombination Determine by I-SceI, a Mitochondrial Group I Intron-Encoded Endonuclease Expressed in the Yeast Nucleus," Genetics, 130:451-460 (1992).
Poland et al., "Structural Insights into the Protein Splicing Mechanism of PI-SCeI," J Biol Chem, 275: 16408-16413 (2000).
Porteus et al., "Chimeric Nucleases Stimulate Gene Targeting in Human Cells," Science, 300, 763 (2003).
Porteus et al., "Efficient Gene Targeting Mediated by Adeno-Associated Virus and DNA Double-Strand Breaks," Mol Cell biol, 23: 3558-3565 (2003).
Posfai et al., "Markerless Gene Replacement in *Escherichia coli* Stimulated by a Double-strand Break in the Chromosome," N.A.R., 27:4409-4415 (1999).
Prieto et al., "Generation and Analysis of Mesophilic Variants of the Thermostable Archael I-DMOI Homing Endonuclease," J. Biol. Chem., 283: 4364-4374 (2008).
Puchta et al., "Two Different but Related Mechanisms are Used in Plants for the Repair o Genomic Double-strand Breaks by Homologous Recombination," PNAS, 93:5055-5060 (1996).
Puchta, "Double-Strand Break-Induced Recombination Between Ectopic Homologous Sequences in Somatic Plant Cells," Genetics, 152:1173-1181 (1999).
Puchta et al., "Homologous Recombination in Plant Cells is Enhanced by in vivo Induction of Double Strand Breaks into DNA by a Site-specific Endonuclease," Nucleic Acids Res, 21: 5034-5040 (1993).
Quirk et al., "Intron Mobility in the T-Even Phages: Hight Frequency Inheritance of Group I Introns Promoted by Intron Open Reading Frames," Cell, 56: 455-465 (1989).
Redondo et al., "Molecular Basis of Xeroderma Pigmentosum Group C DNA Recognition by Engineered Meganucleases," Nature, 456: 107—(2008).
Reynolds et al., "Represion of the HIV-1 5' LTR Promoter and Inhibition of HIV-1 Replication by Using Engineered Zinc-finger Transcription Factors," PNAS, 100:1615-1620 (2003).
Rong et al., "Targeted Mutagenesis by Homologous Recombination I D. Melanogaster," Genes Dev, 16:1568-1581 (2002).
Rouet et al., "Introduction of Double-Strand Breaks into the Genome of Mouse Cells by Expression of a Rare-Cutting Endonuclease," Mol Cell Biol, 14: 8096-8106 (1994).
Rowe et al., Table of Content, The Handbook of Pharmaceutical Excipients, 2003.
Rudin et al., "Genetic and Physical Analysis of Double-Stranded Break Repair and Recombination in *Saccharomyces cerevisiae*," Genetics, 122: 519-534 (1989).
Russell, "Replicating Vectors for Gene Therapy of Cancer: Risks, Limitations and prospects," European Journal Cancer (1994), 30A(8): 1165-117.
Schaefer et al., "Efficient Gene Targeting in the Moss Physcomitrella Patens," Plant J, 11(6): 1195-1206 (1997).
Schiestl et al., "Integration of DNA Fragments by Illegitimate Recombination in *Saccharonmyces cerevisiae*," Proc. Natl. Acad. Sci., 88: 7585-7589 (1991).
Seligman et al., "Mutations Altering the Cleavage Specificity of a Homing Endonuclease," Nucleic Acids Research, 30: 3870-3879 (2002).
Siebert et al., "Efficient Repair of Genomic Double-Strand Breaks by Homologous Recombination Between Directly Repeated Sequences in the Plant Genome," The Plant Cell, 14: 1121-1131 (2002).
Silva et al., "Crystal Structure of the Thermostable Archael Intron-encoded Endonuclease I-Dmol," J Mol Biol, 286:1123-1136 (1999).
Sirven et al., "The Human Immunodeficiency Virus Type-1 Central DNA Flap is a Crucial Determinant of Lentiviral Vector Nuclear Import and Gene Transduction of Human Hematopoietc Stem Cells," Blood, vol. 96, No. 13, 4103-4110 (2000).
Smith et al., "Requirements for Double-Strand Cleavage by Chimeric Restriction Enzymes with Zinc Finger DNA-recognition Domains," Nucleic Acid Research, 28:3361-3369 (2000).
Smith et al., "A Detailed Study of the Substrate Specificity of a Chimeric Restriction Enzyme," Nucleic Acids Research, 27: 674-681 (1999).
Smith et al., "A Combinatorial Approach to Create Artificial Homing Endonucleases Cleaving Chosen Sequences," Nucleic Acids Research, 34: e149 (2006).
Stoddard, Expert Report of Bary L. Stoddard, Ph.D. on the Meaning of the Asserted Claims in Cellectis's Patents, Jan. 16, 2009.
Tabuchi et al., "An In Vitro DNA Virus for In Vitro Evolution," FEBS Letters, 508: 309-312 (2001).
Thierry et al., "Cleavage of Yeast and Bacteriophage T7 Genomes at a Single Site Using the Rare Cutter Endonuclease I-Sce I," Nucleic Acids Research, 19:189-190 (1991).

(56) References Cited

OTHER PUBLICATIONS

Thomas et al., "Introduction of Homologous DNA Sequences into Mammalian Cells Induces Mutations in the Cognate Gene," Nature, 324: 34-38 (1986).
Thomas et al., "High Frequency Targeting of Genes to Specific Sites in the Mammalian Genome," Cell, 44: 419-428 (1986).
Thomas et al., "Targeting of Genes to Specific Sites in the Mammalian Genome," Cold Spring Harb Symp Quant Biol, 51:1101-1113 (1986).
Thomas et al., "Progress and Problems with the Use of Viral Vectors for Gene Therapy," Nature, vol. 346, No. 4: 335-346 (2003).
Takata et al., "Homologous Recombination and Non-homologous End-joining Pathways of DNA Double-Strand Break Repair Have Overlapping Roles in the Maintenance of Chromosomal Integrity in Vertebrate Cells," Embo J. 17: 5497-5508 (1998).
Verma et al., "Gene Therapy: Promises, Problems and Prospects," Nature, vol. 389, 239-242 (1997).
Wadia et al., "Protein Transduction Technology," Curr Opin Biotechnol, 13: 52-56 (2002).
Watson et al., p. 41. Recombinant DNA, 1983.
Wilson, "Pointing Fingers at the Limiting Step in Gene Targeting," Nature Biotechnology, 21(7): 759-760 (2003).
Wilson et al., "Good News on the Clinical Gene Transfer Front," Human Gene Therapy, 19: 429-430 (2008).
Yoon et al., "Targeted Gene Correction of Episomal DNA in Mammalian Cells Mediated by a Chimeric RNA-DNA Oligonucleotide," PNAS, 93: 2071-2076 (1996).
Zennou et al., "HIV-1 Genome Nuclear Import is Mediated by a Central DNA Flap," Cell, 101: 173-185 (2000).
Zhang et al., "A New Logic for DNA Engineering Using Recombination in *Escherichia coli*," Nat. Genet, 20: 123-128 (1998).
Zhang et al., "High Levels of Foreign Gene Expression in Hepatocytes after Tail Vein Injections of Naked Plasmid DNA," Human Gene Therapy, 10:1735-1737 (1999).
Zhong et al., "Adeno-Associated viral Vectors in Gene Therapy," Encyclopedia of Life Sciences, 1-8 (2007).
Office Actions from U.S. Appl. No. 10/543,556 mailed Jun. 6, 2012; Aug. 23, 2011; May 14, 2009; and Aug. 19, 2008.
2nd Request for Ex Parte Reexamination in related US Patent No. 7,897,372 filed Feb. 6, 2012.
Denial of Feb. 6, 2012 Request for Ex Parte Reexamination mailed Mar. 7, 2012, Control No. 90/012,131.
3rd Request for Ex Parte Reexamination in related US Patent No. 7,897,372 filed Sep. 7, 2012.
Chevalier et al., "Flexible DNA Target Site Recognition by Divergent Homing Endonuclease Isoschizomers I-CreI and IMsoI," (2003) J. Mol. Biol., vol. 329, pp. 253-269.
Lucas et al., "Rapid evolution of the DNA-binding site in LAGLIDADG Homing Endonucleases," Nucleaic Acids Research, 2001, vol. 29, No. 4, pp. 960-969.
Ngo et al., "The Protein Folding Problem and Tertiary Structure Prediction," 1994, Merz et al. (ed.), Birkhauser, Boston, MA, pp. 433 and 492-295.
Seligman et al., "Genetic Analysis of the Chlamydomonas reinhardtil I-CreI Mobile Intron Homing System in *Escharichia coli*," Genetics, 1997, vol. 147, pp. 1653-1664.
Sussman et al., Isolation and characterization of new homing endonuclease specificities at individual target.
Sequence Listing: PDB: 1G9Y A, Chain A, Homing Endonuclease I-Crei DNA Substrate Complex with Calcium Protrin NCBI, at http://www.ncbi.nlm.hih.gov/protein/13786774, Sep. 19, 2012.
In re: *Cellectis S.A.* v. *Precision Biosciences, Inc.*, in the United States District Court for the District of Delaware, C.A. No. 11-173-SLR-MPT "Cellectic's Opening Brief on Claims Construction Issues", filed Aug. 15, 2012, Total pp. 839. Part 1 of 3 (279 pages).
In re: *Cellectis S.A.* v. *Precision Biosciences, Inc.*, in the United States District Court for the District of Delaware, C.A. No. 11-173-SLR-MPT "Cellectic's Opening Brief on Claims Construction Issues", filed Aug. 15, 2012, Total pp. 839. Part 2 of 3 (279 pages).
In re: *Cellectis S.A.* v. *Precision Biosciences, Inc.*, in the United States District Court for the District of Delaware, C.A. No. 11-173-SLR-MPT "Cellectic's Opening Brief on Claims Construction Issues", filed Aug. 15, 2012, Total pp. 839. Part 3 of 3 (281 pages).
In re: *Cellectis S.A.* v. *Precision Biosciences, Inc.*, in the United States District Court for the District of Delaware, C.A. No. 11-173-SLR-MPT, Cellectis's Answering Brief on Claim Constructions Issues, filed Sep. 7, 2012, 282 pages.
In re: *Cellectis S.A.* v. *Precision Biosciences, Inc.*, in the United States District Court for the District of Delaware, C.A. No. 11-173-SLR, "Precision Biosciences Third Supp. Responses to Cellectis's First set of Interrogatories", Redacted Version (126 pages).
In re: *Cellectis S.A.* v. *Precision Biosciences, Inc.*, in the United States District Court for the District of Delaware, C.A. No. 11-173-SLR, "Precision Biosciences Fourth Supp. Responses to Cellectis's First set of Interrogatories (No. 3)", Redacted Version (144 pages).
In re: *Cellectis S.A.* v. *Precision Biosciences, Inc.*, in the United States District Court for the District of Delaware, C.A. No. 1:11-cv-00173-SLR-MPT, "Expert Declaration of David Edgell, Ph.D. on the meaning of Claim Terms in Cellectis's '372 Patent" filed Aug. 15, 2012 )130 pages.
Aiuti et al., "Correction of ADA-SCID by Stem Cell Gene Therapy Combined with Nonmyeloablative Conditioning," Science, 196: 2410-2413 (2002).
Aiuti et al., "Gene Therapy for Immunodeficiency Due to Adenosine Deaminase Deficiency," The New England Journal of Medicine, vol. 360, No. 5, 447-458 (2009).
Arimondo et al., "Directing Topoisomerase I Mediated DNA Cleavage to Specific Sites by Camptothecin Tethered to Minor- and Major-Groove Ligands," Angew Chem Int. Ed Engl, 40:3045-3048 (2001).
Arimondo et al., "Design of New Anti-Cancer Agents Based on Topoisomerase Poisons Targeted to Specific DNA Sequences," Curr Med. Chem Anti-Canc Agents, 1:219-235 (2001).
Arnould et al., "Engineering of Large Numbers of Highly Specific Homing Endonucleases that Induce Recombination on Novel DNA Targets," J. Mol. Biol, 355: 443-458 (2006).
Ausubel et al., "Chapter 8, Mutagenesis in Cloned DNA", Current Protocol in Molecular Biology, John Wiley and Sons.
Bae et al., "Human Zinc Fingers as Building Blocks in the Construction of Artificial Transcription Factors," Nat. Biotechnol, 21: 275-280 (2003).
Bell-Pedersen et al., "A Site-Specific Endonuclease and Co-conversion of Flanking Exons Associated with the Mobile td Intron of Phage T4," Gene, 82:119-126 (1989).
Bell-Pedersen et al., "Intron Mobility in Phage T4 is Dependent Upon a Distinctive Class of Endonucleases and Independent of DNA Sequences Encoding the Intron Core: Mechanistic and Evolutionary Implications," Nucleic Acids Res, 18: 3763-3770 (1990).
Kaplitt et al., "Safety and Tolerability of Gene Therapy with an Adeno-Associated Virus (AAV) Borne GAD Gene for Parkinson's Disease: An Open Label, Phase 1 Trial," Lancet, 369: 2097-2105 (2007).
Karberg et al., "Group II Introns as Controllable Gene Targeting Vectors for Genetic Manipulation of Bacteria," Nat. Biotechnol, 19: 1162-1167 (2001).
Kim et al., "Hybrid Restriction Enzymes: Zinc Finger Fusions to Fok I Cleavage Domain," PNAS, 93:1156-1160 (1996).
Kim et al., "Chimeric Restriction Endonuclease," PNAS, 91: 883-887 (1994).
Kim, et al., "Use of the Human Elongation Factor 1? Promoter as a Versatile and Efficient Expression System," Gene, 91:217-223 (1990).
Kohn et al., "Occurrence of Leukaemia Following Gene Therapy of X-Linked Scid," Nature Reviews—Cancer, (3):477-488 (2003).
Lacroix et al., "Automated Discovery and Design of Novel Meganucleases," Cellectis S.A., 1-21.
Lanio et al., "On the Possibility and Limitation of Rational Protein Design to Expand the Specificity of Restriction Enzyme: A Case Study Employing EcoRV as the Target," Protein Eng., 13: 275-281 (2000).
Liang et al., "Homology-directed Repair is a Major Double-Strand Break Repair Pathway in Mammalian Cells," PNAS, 95: 5172-5177 (1998).

(56) References Cited

OTHER PUBLICATIONS

Lin et al., "Capture of DNA Sequences at Double-Strand Breaks in Mammalian Chromosomes," Genetics, 158:1665-1674 (2001).
Liu et al., "Dydrodynamics-based Transfection in Animals by Systemic Administration of Plasmid DNA," Gene Therapy, 6: 1258-1266 (1999).
Gorman et al., "Directed Gene Modification via Triple Helix Formation," Curr Mol. Med, 1: 391-399 (2001).
Guo et al., Group II Introns Designed to Insert into Therapeutically Relevant DNA Target Sites in Human Cells, 289: 452-457 (2000).
Gura, "Systems for Identifying New Drugs Are Often Faulty," Science 1997, pp. 1041-1042.
Haber, "Mating-Type Gene Switching in *Saccharomyces cerevisiae*," Annu Rev Genet, 32: 561-599 (1998).
Haber, "In Vivo Biochemistry: Physical Monitoring of Recombination Induced by Site-specific Endonucleases," Bioessays, 17: 609-620 (1995).
Hacein-Bey-Abina et al., "LMO2-Associated Clonal T Cell Proliferation in Two Patients after Gene Therapy for SCID-X1," Science, 415-419 (2003).
Haines et al., Current Protocols in Human Genetics (1994), Table of Contents, Wiley Online Library, Online ISBN: 9780471142904.
Hanes et al., "In Vitro Selection and Evolution of Functional Proteins by Using Ribosome Display," PNAS, 94: 4937-4942 (1997).
Harding et al., "Intravenous Administration of an AAV-2 vector for the expression of factor IX in mice and a dog model of hemophilia B", Gene Therapy, 11:204-213 (2004).
He et al., "Antibody-ribosome-mRNA (ARM) Complexes as Efficient Selection Particles for In Vitro Display and Evolution of Antibody Combining Sites," Nucl. Acids Res, 25: 5132-5143 (1997).
Heath et al., "The Structure of I-CreI, a Group I Intron-encoded Homing Endonuclease," Nat. Struct Biol, 4: 468-476 (1997).
Henry I et al., "Lago Z and LagZ, Two Genes Derived from the LacZ Gene to Study Epigenetics," C R Acad Sci III, 322, 1061-1070 (1999).
Hess et al., Table of Contents, Pharmaceutical Dosage Forms and Their Use, 1985.
Hu et al., "Probing the Structure of the PI-SceI-DNA Complex by Affinity Cleavage and Affinity Photocross-linking," J Biol Chem, 275: 2705-2712 (2000).
Ichiyanagi et al., "Crystal Structure of an Archaeal Intein-encoded Homing Enconuclease PI-Pful," J Mol Biol, 300: 889-901 (2000).
International Search Report of PCT/IB2004/000848 dated Jul. 23, 2004.
Interlocutory Decision in Opposition Proceedings issued for EP 03744485.8-2405, Feb. 8, 2010.
Isalan et al., "Engineering Nucleic Acid-Binding Proteins by Phage Display," Methods Mol Biol, 148: 417-429 (2001).
Isalan et al., "A Rapid, Generally Applicable Method to Engineer Zinc Fingers Illustrated by Targeting the HIV-1 Promoter," Nat. Biotechnol, 19: 656-660 (2001).
Isalan et al., "Rapid, High-Throughput Engineering of Sequence-Specific Zinc Finger DNA-Binding Proteins," Methods Enzymol, 340: 593-609 (2001).
Jacquier et al., "An Intron-Encoded Protein Is Active in a Gene Conversion Process That Spread an Intron into a Mitochondrial Gene," Cell, 41: 383-394 (1985).
Jasin, "Genetic Manipulation of genomes with Rare-Cutting Endonucleases," Trends in Genetics, vol. 12, No. 6, 224-228 (1996).
Joung et al., "A Bacterial Two-hybrid Selection System for Studying Protein-DNA and Protein-protein Interactions," PNAS, 97:7382-7387 (2000).
Jurica et al., "DNA Recognition and Cleavage by the LAGLIDADG Homing Endonuclease I-CreI", Molecular Cell, 2: 469-476 (1998).
Kadyk et al., "Sister Chromatids Are Preferred Over Homologs as Substrates for Recombinational Repair in *Saccharomyces cerevisiae*," Genetics, 132:387-402 (1992).
Liu et al., "Naked DNA in Gene Therapy," Encyclopedia of Life Science, 1-4 (2005).
Logan et al., "Advances in Lentiviral Vector Design for Gene-Modification of Hematopoietic Stem Cells, "Current Opinion in Biotechnology, 13: 429-436 (2002).
Maggos, "Technology, Industrializing DNA Modification," BioCentury, Cellectis091508, PREC197169 (Jan. 22, 2007).
Marcaida et al., "Crystal Structure of I-Dmol in Complex with its Target DNA Provides New Insights into Meganuclease Engineering," PNAS, 105: 16888-16893 (2008).
Meganuclease I-Sce I (Omega-Nuclease), Cat No. 11 362 399 001, Version Nov. 2004. Roche.
Miller et al., "Human Gene Targeting by Adeno-Associated Virus Vectors Is Enhanced by DNA Double-Strand Breaks," Mol Cell Biol, 23: 3550-3557 (2003).
Miller et al., "Retroviral Vectors in Gene Therapy", Encyclopedia of Life Science, 1-5 (2005).
Moore et al., "Design of Polyzin Finger Peptides with Structured Linkers," PNAS, 98: 1432-1436 (2001).
Moore et al., "Improved DNA Binding Specificity from Polyzinc Finger Peptides by Using Strings of Two-finger Units," PNAS, 98: 1437-1441 (2001).
Mueller et al., "Exon Conconversion Biases Accompanying Intron Homing: Battle of the Nucleases," Genes Dev, 10: 2158-2166 (1996).
Murphy, "Use of Bacteriophage ? Recombination Functions to Promote Gene Replacement in *Escherichia coli*," J. Bacteriol, 180:2063-2071(1998).
Papworth et al., "Inhibition of Herpes Simplex Virus 1 Gene Expression by Designer Zinc-finger Transcription Factors," PNAS, 100:1621-1626 (2003).
Paques et al., "Multiple Pathways of Recombination Induced by Double-Strand Breaks in *Saccharomyces cerevisiae*," Microbial Mol Biol Rev, 63: 349-404 (1999).
Paques et al., "Two Pathways for Removal of Nonhomologous DNA Ends During Double-Strand Break Repair in *Saccharomyces cerevisiae*," Mol. Cell. Boil, 17: 6765-6771 (1997).
Bibikova et al., "Stimulation of Homologous Recombination Through Targeted Cleavage by Chimeric Nucleases," Mol. Cell Biol, 21: 289-297 (2001).
Bibikova et al., "Enhancing Gene Targeting with Designed Zinc Finger Nucleases," Science, 300, 764 (2003).
Biet et al., Homologous Recombination and Gene Targeting (in French with English abstract), Compes Rendues-Biologies, 326(1): 51-64 (2003).
Bonetta, "Getting Proteins Into Cells: The Discovery and Commercialization of Protein Transduction Domains Frees Researchers from Transfection Troubles," The Scientist, 16: 38-40 (2002).
Buerstedde et al., "Increased Ratio of Targeted to Random Integration after Transfection of Chicken B Cell Lines," Cell, 67: 179-188 (1991).
Cabaniols et al., "Robust Cell Lin Development Using Meganucleases," Methods in Molecular Biology, (2008), vol. 435: 31-45.
Chames et al., "In Vivo Selection of Engineered Homing Endonucleases using Double-Strand Break Induced Homologous Recombination," Nucleic Acids Res., 33: e178 (2005).
Cavazzana-Calvo et al., "Gene Therapy of Human Sever Combined Imminodificiency (SCID)-X1 Disease," Science, 288: 669-672 (2000).
Chevalier et al., "Design, Activity, and Structure of a Highly Specific Artificial Endonuclease," Molecular Cell, 10:895-905 (2002).
Chevalier et al, "Homing Endonucleases: Structural and Functional Insight Into Catalysts of Intron/Intein Mobility," Nucleic Acids Resarch, 29: 3757-3774 (2001).
Chevalier et al, "The Homing Endonuclease I-CreI Uses Three Metals, One of Which is Shared Between the Two Active Sites," Nat Struct Biol, 8:312-316 (2001).
Chiurazzi et al., "Enhancement of Somatic Intrachromosomal Homologous Recombination in Arabidopsis by the HO Endonuclease," Plant Cell, 8:2057-2066 (1996).
Choulika et al., "Induction of Homologous Recombination if Mammalian Chromosomes by Using the I-SceI System of *Saccharomyces cerevisiae*," Mol Cell Biol, 15: 1968-1973 (1995).

(56) References Cited

OTHER PUBLICATIONS

Choulika et al., "The Yeast I-SceI Meganuclease Induces Site-Directed Chromosomal Recombination in Mammalian Cells," C R Acad Sci III,1994 317:1013-9 (1994).

Coffin, "Chapter 26, Retroviridae: The Viruses and their Replication," Fundamental Virology, 3rd ed., B.N. Fields, Lippincott-Raven Publishers, Philadelphia, 1996.

Cohen-Tannoudji et al., "I-SceI-Induced Gene Replacement at Natural Locus in Embryonic Stem Cells," Mol Cell Biol, 18: 1444-1448 (1998).

Colleaux et al., "Recognition and Cleavage Site of the Intron-encoded Omega Transposase," PNAS, 85:6022-6026 (1998).

Colleaux et al., "Universal Code Equivalent of a Yeast Mitochondrial Intron Reading Frame Is Expressed into E. Coli as a Specific Double Strand Endonuclease," Cell, 44:521-533 (1986).

Delacote et al., "Importance of the cell cycle Pphase for the choice of the appropriate DSB repair pathway, for genome stability maintenance", Cell Cycle, 7:1, 33-38 (2008).

Delahodde et al., "Site-Specific DNA Endonuclease and RNA Mautrase Activities of Two Homologous Intron-Encoded Proteins from Yeast Mitochondria," Cell, 56: 431-441 (1989).

Doetschman et al., "Targeted Mutation of the Hprt Gene in Mouse Embryonic Stem Cells," PNAS, 85: 8583-8587 (1988).

Donoho et al., "Analysis of Gene Targeting and Intrachromosomal Homologous Recombination Stimulated by Genomic Double-Strand Breaks in Mouse Embryonic Stem Cells," Mol Cell Biol, 18: 4070-4078 (1998).

Duan et al., "Crystal Structure of PI-SceI, a Homing Endonuclease with Protein Splicing Activity," Cell, 89: 555-564 (1997).

Dujon et al., "Group I Introns as Mobile Genetic Elements: Facts and Mechanistic Speculations—a Review," Gene, 82: 91-126 (1989).

Dujon et al., "Cellectis. Celletis' 5th Scientific Advisory Board Meeting. Report of the Meeting," p. 1-4, Dec. 16-17, 2004.

Dujon et al., "Homing Endonucleases and the Yeast Mitochondrial Locus—A Historical Perspective," Nucleic Acids and Molecular Biology, 16: 11-31 (2005).

Durrenberger et al., "Chloroplast Ribosomal Intron of Chlamydomonas Reinhardtil: In Vitro Self-Splicing, DNA Endonuclease Activity and In Vivo Mobility," the EMBO J, 10:3495-3501 (1991).

Eisenschmidt et al., "A Fluorimetric Assay for On-line Detection of DNA Cleavage by Restriction Endonucleases," Journal of Biotechnology, 96: 185-191 (2002).

Epinat et al., "A Novel Engineered Meganuclease Induces Homologous Recombination in Yeast and Mammalian Cells", Nucleic Acids Research, 31: 2952-2962 (2003).

Essers et al., "Disruption of Mouse RAD54 Reduces Ionizing Radiation Resistance and Homologous Recombination," Cell, 89: 195-204 (1997).

Fairhead et al., "Consequences of Unique Double-Stranded Breaks in Yeast Chromosomes: Death or Homozygosis," Mol Gen Genet, 240:170-188 (1993).

Feigin et al., "Modulation of Metabolic Brain Networks After Subthalamic Gene Therapy for Parkinson's Disease," PNAS, 104: 1959-19564 (2007).

Fischer et al., "Gene Therapy for Human Severe Combined Immunodeficiencies," Isr. Med. Assoc J. 4:51-54 (2002).

Fischer et al., "LM02 and Gene Therapy for Severe Combined Immunodificiency," The New England Journal of Medicine, 2526-2527 (2004).

Fishman-Lobell et al., "Removal of Nonhomologous DNA Ends in Double-Strand Break Recombination: The Role of the Yeast Ultraviolet Repair Gene RAD 1," Science, 258: 480-484 (1992).

Ford et al., "Protein Transduction: An Alternative to Genetic Intervention?" Gene Ther, 8: 1-4 (2001).

Galetto et al., "Target Approaches for Gene Therapy and the Emergence of Engineered Meganucleases," Expert Opin. Biol. Ther, 9:1289-1303 (2009).

Gasior et al., "Assembly of RecA-like Recombinases: Distinct Roles for Mediator Proteins in Mitosis and Meiosis," PNAS, 98: 8411-8418 (2001).

Gaspar et al., "Gene Therapy of X-Linked Severe Combined Immunodificiency by Use of a Pseudotyped Gammaretroviral Vector," Lancet, 364: 2181-2187 (2004).

Goncz et al., "Application of SHFR to Gene Therapy of Monogenic Disorders," Gene Therapy, 9: 691-69 (2002).

Prieto, J. et al., "The C-terminal Loop of the Homing Endonuclease I-CreI is Essential for Site Recognition, DNA Binding and Cleavage", Nucleic Acid Research, vol. 31, No. 10 3262-3271 (2007).

Rebar, E. J. et al., "Zinc Finger Phage: Affinity Selection of Fingers with New DNA-Binding Specificities", Science 263: 671-673 (1994).

Jamieson, A. C. et al., "Drug Discovery with Engineered Zinc-Finger Proteins", Nat. Rev. Drug Discov., 2: 361-368 (2003).

Redondo, P. et al., "Molecular Basis of Xeroderma Pigmentosum Group C DNA Recognition by Engineered Meganucleases," Nature (2008), vol. 456, pp. 107-113.

Rogakou, E. P. et al., "DNA Double-stranded Break Induce Histone H2AX Phosphorylation on Serine 139*", J. Biol. Chem., 273: 5858 (1998).

Rosen, L. E. et al., "Homing Endonuclease I-CreI Derivatives with Novel DNA Target Specificities," Nucleic Acids Res., 34: 4791-4800 (2006).

Rouet, P. et al., "Introduction of Double-Strand Breaks into the Genome of Mouse Cells by Expression of a Rare-Cutting Endonuclease," Mol Cell Biol, 14: 8096-8106 (1994).

Sambrook, J. et al., Molecular Cloning: A Laboratory Manual, 3rd ed., Cold Spring Harbor, New York, Cold Spring Harbor Laboratory Press. Table of content. 2001.

Seligman, L. M. et al., "Mutations Altering the Cleavage Specificity of a Homing Endonuclease," Nucleic Acids Research, 30: 3870-3879 (2002).

Silva, G. H. et al., "Crystal Structure of the Thermostable Archael Intron-encoded Endonuclease I-Dmol," J Mol Biol, 286:1123-1136 (1999).

Silva, G. H. et al., "From Monomeric to Homodimeric Endonucleases and Back: Engineering Novel Specificity of LAGLIDADG Enzymes", Science Direct, 744-754, (2006).

Smith, J. et al., "A Combinatorial Approach to Create Artificial Homing Endonucleases Cleaving Chosen Sequences", Nucleic Acid Research, vol. 34, No. 22, 1-12, (2006).

Smith, J. et al., "A Detailed Study of the Substrate Specificity of a Chimeric Restriction Enzyme," Nucleic Acids Research, 27: 674-681 (1999).

Sussman, D. et al., "Isolation and Characterization of New Homing Endonuclease Specificities at Individual Target Site Positions," J. Mol. Biol., 342: 31-41 (2004).

Urnov, F. D. et al., "Highly Efficient Endogenous Human Gene Correction Using Designed Zinc-Finger Nucleases," Nature, 435: 646-651 (2005).

Wadia, J. S. et al., "Protein Transduction Technology," Curr. Opin. Biotechnl., 13: 52-56 (2002).

Weir, D. M. et al., Handbook of Experimental Immunology, vol. I-IV, Cold Spring Harbor, New York. Table of Content (1986).

Alwin, S. et al., "Custom Zinc-Finger Nucleases for Use in Human Cells," Mol. Ther., 12: 610-617 (2005).

Bibikova, M. et al., "Targeted Chromosomal Cleavage and Mutagenesis in Drosophila using Zinc-Finger Nucleases," Genetics, 161: 1169-1175 (2002).

Arnould, S. et al., "Engineering of Large Numbers of Highly Specific Homing Endonucleases that Induce Recombination on Novel DNA Targets," J. Mol. Biol, 355: 443-458 (2006).

Ashworth, J. et al., "Computational Redesign of Endonuclease DNA Binding and Cleavage Specificity," Nature, 441: 656-659 (2006).

Beumer, K. et al., "Efficient Gene Targeting in Droscophila With Zinc Finger Nucleases", Genetics 172: 2391-2403 (2006).

Jurica, M. S. et al., "DNA Recognition and Cleavage by the LAGLIDADG Homing Endonuclease I-CreI," Molecular Cell, 2: 469-476 (1998).

(56) References Cited

OTHER PUBLICATIONS

Isalan, M. et al., "A Rapid, Generally Applicable Method to Engineer Zinc Fingers Illustrated by Targeting the HIV-1 Promoter," Nat. Biotechnol, 19: 656-660 (2001).
Woodward, J., Immobilized Cells and Enzymes: A Practical Approach, IRL Press, Oxford, England. Table of Content (1986).
Ichiyanagi, K. et al., "Crystal Structure of an Archaeal Intein-encoded Homing Enconuclease PI-Pful," J Mol Biol, 300: 889-901 (2000).
Bolduc, J. M. et al., "Structural and Biochemical Analyses of DNA and RNA Binding by a Bifunctional Homing Endonuclease and Group I Intron Splicing Factor," Genes Dev,. 17: 2875-2888 (2003).
Catto, L. et al., "Protein assembly and DNA looping by the FokI restriction endonuclease", Nucleic Acids Res., 34: 1711-1720 (2006).
Chevalier, B. et al, "Flexible DNA Target Site Recognition by Divergent Homing Endonuclease Isoschizomers I-CreI and I-MsoI," J. Mol. Biol., 329: 253-269 (2003).
Duan, X. et al., "Crystal Structure of PI-SceI, a Homing Endonuclease with Protein Splicing Activity," Cell, 89: 555-564 (1997).
Lucas, P. et al., "Rapid Evolution of the DNA-binding site in LAGLIDADG Homing Endonucleases," Nucleic Acids Research, 29(4): 960-969 (2001).
Kim, Jin-Soo et al., "Getting a handhold on DNA: Design of poly-zinc finger proteins with femtomolar dissociation constants", Proc. Natl. Acad. Sci. 95: 2812-2817 (1998).
Freshney, R. I. et al., Culture of Animal Cells: A Manual of Basic Technique. Alan R. Liss, Inc., New York. Table of Content (1987).
Gait, M. J., ed., Oligonucleotide Synthesis: A practical Approach, IRL Press, Oxford, England. Table of Content. (1984).
Gietz, R. D. et al., "Transformation of Yeast by Lithium Acetate/Single-Stranded Carrier DNA/Polyethylene Glycol Method", Methods Enzymol., 350: 87-96 (2002).
Gimble, F. S. et al., "Assessing the Plasticity of DNA Target Site Recognition of the PI-SceI Homing Endnuclease Using a Bacterial Two-hybrid Selection System", J. Mol. Biol., 334: 993-1008 (2003).
Gouble, A. et al., "Efficient in toto targeted recombination in mouse liver by meganucleaseinduced double-strand break", J. Gene Med., 8: 616-622 (2006).
Grindl, W. et al "The Protein Splicing domain of the Homing Endlocuclease PI-SceI is Responsible for Specific DNA Binding," Nucleic Acids Res., 26: 1857-1862 (1998).
Hacein-Bey-Abina, S. et al., "LMO2-Associated Clonal T Cell Proliferation in Two Patients after Gene Therapy for SCID-X1," Science, 415-419 (2003).
Hames, B. D., Transcription and Translation: A Practical Approach, IRL Press, Oxford, England. Table of Content (1984).
Hames, B. D. et al. ed, Nucleic Acid Hybridization: A Practical Approach, IRL Press, Oxford, England. Table of Content. 1984.
Shen et al., "DNA binding and cleavage by the HNH homing endonuclease I-HmuI," J. Mol Biol, (2004), vol. 342, pp. 43-56.
Spiegel et al., "The Structure of I-CeuI Homing Endonuclease: Evolving Asymmetric DNA Recognition from a Symmetric Protein Scaffold," Structure, (2006), vol. 14, pp. 869-880.
Stoddard, "Homing endonuclease structure and function," Q Rev Biophys, (2005), vol. 38, pp. 49-95.
Sussman et al., "Isolation and characterization of new homing endonuclease specificities at individual target site positions," J Mol. Biol. (2004), vol. 342, pp. 31-41.
Takeuchi et al, "Optimization of in vivo activity of a bifunctional homing endonuclease and maturase reverses evolutionary degradation," Nucleic Acids Res, (2009), vol. 37, pp. 877-890.
Tao et al., "Milestones in directed enzyme evolution," Curr Opin Chem Biol, (2002), vol. 6, pp. 858-864.
Van Roey et al., "Intertwined structure of the DNA-binding domain of intron endonuclease I-TevI with its substrate." EMBO J, (2001), vol. 20, pp. 3631-3637.
Wang et al.. "Purification, biochemical characterization and protein-DNA interactions of the I-CreI endonuclease produced in *Escherichia coli*," Nucleic Acids Res, (1997), vol. 25, pp. 3767-3776.
Weinstock et al., "A model of oncogenic rearrangements: differences between chromosomal translocation mechanisms and simple double-strand break repair," Blood, (2006a), vol. 107, pp. 777-780.
Weinstock et al., "Modeling oncogenic translocations: distinct roles for double-strand break repair pathways in translocation formation in mammalian cells," DNA Repair (Amst), (2006b), vol. 5, pp. 1065-1074.
Wu et al., "Intein-mediated purification of cytotoxic endonuclease I-TevI by insertional inactivation and pH-controllable splicing," Nucleic Acids Res, (2002), vol. 30, pp. 4864-4871.
Zhao et al., "The restriction fold turns to the dark side: a bacterial homing endonuclease with a PD-(D/E)-XK motif," EMBO J, (2007), vol. 26, pp. 2432-2442.
Office Action from U.S. Appl. No. 10/543,556 mailed Aug. 23, 2011 and Jun. 6, 2012.
Office Action from U.S. Appl. No. 12/091,216 mailed Jul. 16, 2012, Feb. 1, 2012.
Office Action from U.S. Appl. No. 10/388,230 mailed Nov. 15, 2010, Jul. 14, 2011.
Office Action from U.S. Appl. No. 10/507,736 mailed Jan. 27, 2011.
Office Action from U.S. Appl. No. 12/482,124 mailed Aug. 23, 2012.
Office Action from U.S. Appl. No. 13/021,473 mailed May 3, 2011.
Office Action from U.S. Appl. No. 13/524,995 mailed Nov. 23, 2012.
Office Action from U.S. Appl. No. 12/710,969 mailed Jul. 14, 2010.
Office Action from U.S. Appl. No. 11/908,934 mailed Mar. 14, 2011, Jul. 21, 2010, Dec. 14, 2009.
Office Action from U.S. Appl. No. 12/091,632 mailed Dec. 13, 2012 and Apr. 16, 2012.
Office Action from U.S. Appl. No. 12/892,708 mailed Jun. 4, 2012.
Office Action from U.S. Appl. No. 12/449,329 mailed Jun. 1, 2012.
Office Action from U.S. Appl. No. 12/663,445 mailed Nov. 28, 2012 and May 4, 2012.
Request for Ex Parte Reexamination filed Jul. 22, 2011 in related US Patent No. 7,842,489.
Denial of Jul. 22, 2011 Request for Ex Parte Reexamination mailed Sep. 28, 2011, Control No. 90/011,806.
Petition for Review of Sep. 28, 2011 Order Denying Request for Ex Parte Reexamination filed Oct. 28, 2011.
Order granting Oct. 28, 2011 Petition mailed Jul. 30, 2012.
1st Request for Ex Parte Reexamination in related US Patent No. 7,897,372 filed May 10, 2011, Control No. 90/011,665.
Order granting May 10, 2011 Replacement Request for Ex Parte Reexamination mailed Jul. 8, 2011, Control No. 90/011,665.
Office Action in Reexamination Control No. 90/011,665 mailed Jan. 18, 2012.
Response to Jan. 18, 2012 Office Action in Reexamination Control No. 90/011,665 filed May 2, 2012.

```
                              -11 -10 -9 -8 -7 -6 -5 -4 -3 -2 -1  1  2  3  4  5  6  7  8  9 10 11
C1221     (SEQ ID NO: 21)  CAAAACGTCGTACGACGTTTTG
10GAG_P   (SEQ ID NO: 27)  CGAGACGTCGTACGACGTCTCG
10GTA_P   (SEQ ID NO: 28)  CGTAACGTCGTACGACGTTACG
 5TCT_P   (SEQ ID NO: 29)  CAAAACTCTGTACAGAGTTTTG
C1        (SEQ ID NO: 26)  CGAGATGTCACACAGAGGTACG
C3        (SEQ ID NO: 30)  CGAGATGTCGTACGACATCTCG
C4        (SEQ ID NO: 31)  CGTACCTCTGTACAGAGGTACG
```

```
                              -11 -10 -9 -8 -7 -6 -5 -4 -3 -2 -1  1  2  3  4  5  6  7  8  9 10 11
C1221       (SEQ ID NO: 21) C  A  A  A  A  C  G  T  C  G  T  A  C  G  A  C  G  T  T  T  T  G
10GAG_P     (SEQ ID NO: 27) C  G  A  G  A  C  G  T  C  G  T  A  C  G  A  C  G  T  C  T  C  G
10CAT_P     (SEQ ID NO: 32) C  C  A  T  A  C  G  T  C  G  T  A  C  G  A  C  G  T  A  T  G  G
5CTT_P      (SEQ ID NO: 33) C  A  A  A  A  C  C  T  T  G  T  A  C  A  A  G  G  T  T  T  T  G
HprCH3      (SEQ ID NO: 34) C  G  A  G  A  T  G  T  C  A  T  G  A  A  A  G  A  G  A  T  G  G
HprCH3.3    (SEQ ID NO: 35) C  G  A  G  A  T  G  T  C  G  T  A  C  G  A  C  A  T  C  T  C  G
HprCH3.4    (SEQ ID NO: 36) C  C  A  T  C  T  C  T  T  G  T  A  C  A  A  G  A  G  A  T  G  G
```

FIGURE 13

```
                                    -11 -10 -9 -8 -7 -6 -5 -4 -3 -2 -1  1  2  3  4  5  6  7  8  9 10 11
C1221                               CAAAACGTCGTACGACGTTTTG
         (SEQ ID NO: 21)
10GTT_P                             CGTTACGTCGTACGACGTAACG
5CAG_P   (SEQ ID NO: 37)            CAAAACCAGGTACCTGGTTTTG
10TGG_P  (SEQ ID NO: 38)            CTGGACGTCGTACGACGTCCAG
5GAG_P   (SEQ ID NO: 39)            CAAAACGAGGTACCTCGTTTTG
         (SEQ ID NO: 40)
RAG1.10  (SEQ ID NO: 41)            TGTTCTCAGGTACCTCAGCCAG
RAG1.10.2                           TGTTCTCAGGTACCTGAGAACA
         (SEQ ID NO: 42)
RAG1.10.3                           CTGGCTGAGGTACCTCAGCCAG
         (SEQ ID NO: 43)
```

FIGURE 17

A
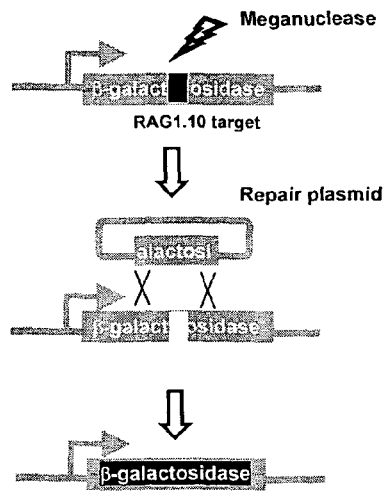
B
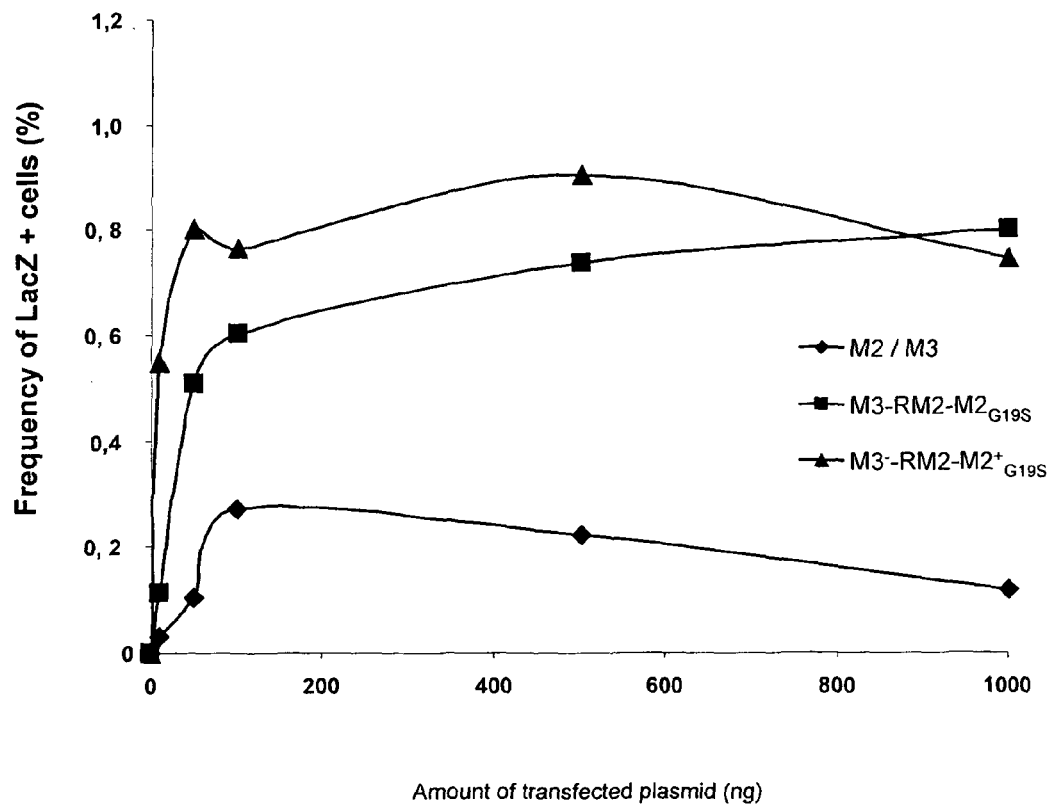
Amount of transfected plasmid (ng)
FIGURE 22

Wild-type Rag1 locus
PCR negative
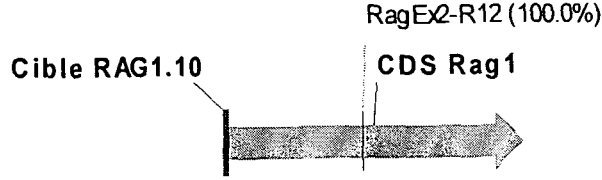
Targeted Rag1 locus
PCR amplification (2588bp)
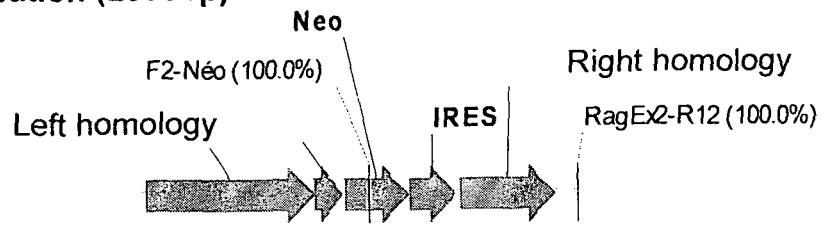
Random insertion of repair plasmid
PCR negative
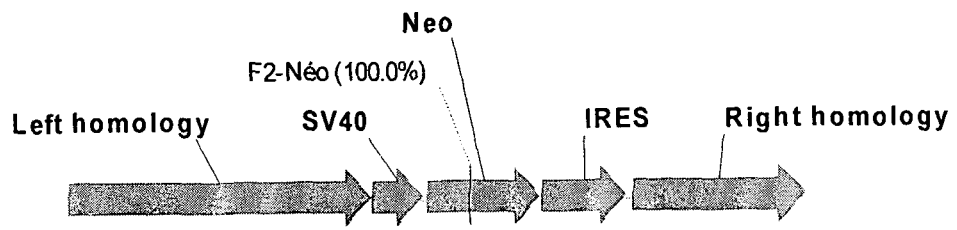
FIGURE 26

I-*CRE*I DERIVED SINGLE-CHAIN MEGANUCLEASE AND USES THEREOF

SEQUENCE LISTING

The instant application contains a Sequence Listing which has been submitted in ASCII text via EFS-Web and is hereby incorporated by reference in its entirety. Said ASCII copy is named 15047US1.txt and is 40,000 bytes in size.

The invention relates to a new I-CreI derived single-chain meganuclease, to a vector encoding said new I-CreI derived single-chain meganuclease, to a cell, an animal or a plant modified by said vector and to the use of said I-CreI derived single-chain meganuclease and derived products for genetic engineering, genome therapy and antiviral therapy.

Among the strategies to engineer a given genetic locus, the use of rare cutting DNA endonucleases such as meganucleases has emerged as a powerful tool to increase homologous gene targeting through the generation of a DNA double strand break (DSB). Meganucleases recognize large (>12 bp) sequences, and can therefore cleave their cognate site without affecting global genome integrity. Homing endonucleases, the natural meganucleases, constitute several large families of proteins encoded by mobile introns or inteins. Their target sequence is usually found in homologous alleles that lack the intron or intein, and cleavage initiates the transfer of the mobile element into the broken sequence by a mechanism of DSB-induced homologous recombination. I-SceI was the first homing endonuclease used to stimulate homologous recombination over 1000-fold at a genomic target in mammalian cells (Choulika et al., Mol. Cell. Biol., 1995, 15, 1968-1973; Cohen-Tannoudji et al., Mol. Cell. Biol., 1998, 18, 1444-1448; Donoho et al., Mol. Cell. Biol., 1998, 18, 4070-4078; Alwin et al., Mol. Ther., 2005, 12, 610-617; Porteus, M. H., Mol. Ther., 2006, 13, 438-446; Rouet et al., Mol. Cell. Biol., 1994, 14, 8096-8106). Recently, I-SceI was also used to stimulate targeted recombination in mouse liver in vivo, and recombination could be observed in up to 1% of hepatocytes (Gouble et al., J. Gene Med., 2006, 8, 616-22).

However an inherent limitation of such a methodology is that it requires the prior introduction of the natural cleavage site into the locus of interest. To circumvent this limitation, significant efforts have been made over the past years to generate endonucleases with tailored cleavage specificities. Such proteins could be used to cleave genuine chromosomal sequences and open new perspectives for genome engineering in wide range of applications. For example, meganucleases could be used to induce the correction of mutations linked with monogenic inherited diseases, and bypass the risk due to the randomly inserted transgenes used in current gene therapy approaches (Hacein-Bey-Abina et al., Science, 2003, 302, 415-419).

Fusion of Zinc-Finger Proteins (ZFPs) with the catalytic domain of the FokI, a class IIS restriction endonuclease, were used to make functional sequence-specific endonucleases (Smith et al., Nucleic Acids Res., 1999, 27, 674-681; Bibikova et al., Mol. Cell. Biol., 2001, 21, 289-297; Bibikova et al., Genetics, 2002, 161, 1169-1175; Bibikova et al., Science, 2003, 300, 764; Porteus, M. H. and D. Baltimore, Science, 2003, 300, 763-; Alwin et al., Mol. Ther., 2005, 12, 610-617; Urnov et al., Nature, 2005, 435, 646-651; Porteus, M. H., Mol. Ther., 2006, 13, 438-446). Such nucleases could recently be used for the engineering of the ILR2G gene in human cells from the lymphoid lineage (Urnov et al., Nature, 2005, 435, 646-651).

The binding specificity of Cys2-His2 type Zinc-Finger Proteins, is easy to manipulate, probably because they represent a simple (specificity driven by essentially four residues per finger), and modular system (Pabo et al., Annu. Rev. Biochem., 2001, 70, 313-340; Jamieson et al., Nat. Rev. Drug Discov., 2003, 2, 361-368). Studies from the Pabo (Rebar, E. J. and C. O. Pabo, Science, 1994, 263, 671-673; Kim, J. S. and C. O. Pabo, Proc. Natl. Acad. Sci. USA, 1998, 95, 2812-2817), Klug (Choo, Y. and A. Klug, Proc. Natl. Acad. Sci. USA, 1994, 91, 11163-11167; Isalan M. and A. Klug, Nat. Biotechnol., 2001, 19, 656-660) and Barbas (Choo, Y. and A. Klug, Proc. Natl. Acad. Sci. USA, 1994, 91, 11163-11167; Isalan M. and A. Klug, Nat. Biotechnol., 2001, 19, 656-660) laboratories resulted in a large repertoire of novel artificial ZFPs, able to bind most G/ANNG/ANNG/ANN sequences.

Nevertheless, ZFPs might have their limitations, especially for applications requiring a very high level of specificity, such as therapeutic applications. The FokI nuclease activity in fusion acts as a dimer, but it was recently shown that it could cleave DNA when only one out of the two monomers was bound to DNA, or when the two monomers were bound to two distant DNA sequences (Catto et al., Nucleic Acids Res., 2006, 34, 1711-1720). Thus, specificity might be very degenerate, as illustrated by toxicity in mammalian cells (Porteus, M. H. and D. Baltimore, Science, 2003, 300, 763) and *Drosophila* (Bibikova et al., Genetics, 2002, 161, 1169-1175; Bibikova et al., Science, 2003, 300, 764-.).

Given their exquisite specificity, homing endonucleases may represent ideal scaffolds for engineering tailored endonucleases. Several studies have shown that the DNA binding domain from LAGLIDADG proteins, the most widespread homing endonucleases (Chevalier, B. S, and Stoddard B. L., Nucleic Acids Res. 2001; 29:3757-74) could be engineered. LAGLIDADG refers to the only sequence actually conserved throughout the family and is found in one or more often two copies in the protein (Lucas et al., Nucleic Acids Res., 2001, 29:960-969). Proteins with a single motif, such as I-CreI (Protein Data Bank accession number 1 G9Y) and I-MsoI, form homodimers and cleave palindromic or pseudo-palindromic DNA sequences, whereas the larger, double motif proteins, such as I-SceI and I-DmoI are monomers and cleave non-palindromic targets. Several different LAGLIDADG proteins have been crystallized, and they exhibit a very striking conservation of the core structure that contrasts with the lack of similarity at the primary sequence level (Jurica et al., Mol. Cell., 1998; 2:469-476; Chevalier et al., Nat. Struct. Biol. 2001; 8:312-316; Chevalier et al., J. Mol. Biol., 2003, 329:253-69, Moure et al., J. Mol. Biol., 2003, 334:685-695; Moure et al., J. Mol. Biol., 2003, 334, 685-695; Moure et al., Nat. Struct. Biol., 2002, 9:764-770; Ichiyanagi et al., J. Mol. Biol., 2000, 300:889-901; Duan et al., Cell, 1997, 89:555-564; Bolduc et al., Genes Dev., 2003, 17:2875-2888; Silva et al., J. Mol. Biol., 1999, 286:1123-1136). In this core structure, two characteristic $\alpha\beta\beta\alpha\beta\beta\alpha$ folds, contributed by two monomers, or by two domains in double LAGLIDAG proteins, are facing each other with a two-fold symmetry. DNA binding depends on the four $\beta$-strands from each domain, folded into an antiparallel $\beta$-sheet, and forming a saddle on the DNA helix major groove. The catalytic core is central, with a contribution of both symmetric monomers/domains. In addition to this core structure, other domains can be found: for example, PI-SceI, an intein, has a protein splicing domain, and an additional DNA-binding domain (Moure et al., Nat. Struct. Biol., 2002, 9:764-70, Grindl et al., Nucleic Acids Res. 1998, 26:1857-1862). Each I-CreI monomer comprises a C-terminal subdomain made of three helices (alpha 4 ($\alpha_4$), alpha 5 ($\alpha_5$) and alpha 6 ($\alpha_6$)) and a loop between the $\alpha_5$ and $\alpha_6$ helices (C-terminal loop; FIG. 1), which is essential for site recognition, DNA binding and cleavage (Prieto et al., Nucleic Acids Res., 2007, 35, 3267-3271).

Several LAGLIDADG proteins, including PI-SceI (Gimble et al., J. Mol. Biol., 2003, 334:993-1008), I-CreI (Seligman et al., Nucleic Acids Res. 2002, 30:3870-3879; Sussman et al., J. Mol. Biol., 2004, 342:31-41; International PCT Applications WO 2006/097784, WO 2006/097853, WO 2007/060495 and WO 2007/049156; Arnould et al., J. Mol. Biol., 2006, 355, 443-458; Rosen et al., Nucleic Acids Res., 2006, 34, 4791-4800; Smith et al., Nucleic Acids Res., 2006, 34, e149), I-SceI (Doyon et al., J Am Chem. Soc., 2006, 128:2477-2484) and I-MsoI (Ashworth et al., Nature, 2006, 441:656-659) could be modified by rational or semi-retional mutagenesis and screening to acquire new binding or cleavage specificities.

Another strategy was the creation of new meganucleases by domain swapping between I-CreI and I-DmoI, leading to the generation of a meganuclease cleaving the hybrid sequence corresponding to the fusion of the two half parent target sequences (Epinat et al., Nucleic Acids Res., 2003, 31:2952-2962; Chevalier et al., Mol. Cell. 2002, 10:895-905; International PCT Applications WO 03/078619 and WO 2004/031346).

Recently, semi rational design assisted by high throughput screening methods allowed to derive thousands of novel proteins from I-CreI (Smith et al., Nucleic Acids Res. 2006, 34, e149; Arnould et al., J. Mol. Biol., 2006, 355:443-458; International PCT Applications WO 2006/097784, WO 2006/097853, WO 2007/060495 and WO 2007/049156). In such an approach, a limited set of protein residues are chosen after examination of protein/DNA cocrystal structure, and randomized. Coupled with high-throughput screening (HTS) techniques, this method can rapidly result in the identification of hundreds of homing endonucleases derivatives with modified specificities.

Furthermore, DNA-binding sub-domains that were independent enough to allow for a combinatorial assembly of mutations were identified (Smith et al., Nucleic Acids Res. 2006, 34, e149; International PCT Applications WO 2007/049095 and WO 2007/057781). These findings allowed for the production of a second generation of engineered I-CreI derivatives, cleaving chosen targets. This combinatorial strategy, has been illustrated by the generation of meganucleases cleaving a natural DNA target sequence located within the human RAG1 and XPC genes (Smith et al., Nucleic Acids Res., 2006, 34, e 149; Arnould et al., J. Mol. Biol., 2007, 371:49-65; International PCT Applications WO 2007/093836, WO 2007/093918 and WO 2008/010093).

The engineered meganucleases cleaving natural DNA targets from the human RAG1 or XPC genes are heterodimers, which include two separately engineered monomers, each binding one half of the target. Heterodimer formation is obtained by co-expression of the two monomers in the same cells (Smith et al., Nucleic Acids Res., 2006, 34, e149). Such co-expression of two monomers result in the formation of three molecular species: the heterodimer, which cleaves the target of interest, and the two homodimers, which can be considered as by-products (Arnould et al., J. Mol. Biol., 2006, 355, 443-458; International PCT Applications WO 2006/097854 and WO 2007/057781; Smith et al., Nucleic Acids Res., 2006, 34, e149). However, individual homodimers can sometimes be responsible for high levels of toxicity (Bibikova et al., Genetics, 2002, 161, 1169-1175; Beumer et al., Genetics, 2006, 172, 2391-2403). Thus, a limiting factor that still remains for the widespread use of the single-LAGLIDADG homing endonucleases such as I-CreI, is the fact that proteins are homodimers. Two possibilities can overcome this issue: either the making of obligatory heterodimers, by redesign of the dimerization interface, resulting in the suppression of functional homodimer formation, or the fusion of the two monomers with a protein link or linker in a single chain molecule, in order to favor intramolecular over intermolecular interactions of distincts $\alpha\beta\beta\alpha\beta\beta\alpha$ folds. This last strategy would have an additional advantage in terms of vectorization, for only one coding sequence or proteins would have to be introduced into the nucleus. It would thus alleviate the use of two different vectors, or of bicistronic ones. Note that at least in theory, the single chain molecule would not necessarily alleviate the interaction of $\alpha\beta\beta\alpha\beta\beta\alpha$ folds from distinct molecules, especially if the linker is long and flexible, but it should at least favor interactions between $\alpha\beta\beta\alpha\beta\beta\alpha$ folds from a same molecule. Furthermore, the making of single chain molecule and the redesign of the dimerization interface are not exclusive strategies and could be used jointly.

The making of a single-chain version of I-CreI (scI-CreI) has already been tested (Epinat et al., Nucleic Acids Res., 2003, 3, 2952-2962, International PCT Application WO 03/078619). In this first version, the N-terminal domain of the single-chain meganuclease (positions 1 to 93 of I-CreI amino acid sequence) consisted essentially of the $\alpha\beta\beta\alpha\beta\beta\alpha$ fold (core domain) of an I-CreI monomer whereas the C-terminal (positions 8 to 163 of I-CreI amino acid sequence) was a nearly complete I-CreI monomer. The linker (MLERIRLFNMR; SEQ ID NO: 1) was derived from the loop joining the two domains of I-DmoI.

Although the first scI-CreI was a functional meganuclease, it was less stable than I-CreI, probably due a less optimal folding as compared to its natural counterpart. The design of the first scI-CreI matched the structure of double LAGLIDADG endonucleases and therefore differed from that of I-CreI in that the N-terminal domain is shorter than the C-terminal domain and lacks the C-terminal subdomain made of three $\alpha$-helices which may be present in the C-terminal domain of some double LAGLIDADG endonucleases.

The removal of the three C-terminal helices from the first monomer might affect the folding, stability and consequently the cleavage activity of the first scI-CreI since recent works have shown the crucial role of the C-terminal subdomain of I-CreI in the protein DNA binding properties and DNA target cleavage activity (Prieto et al., Nucleic Acids Res., 2007,), 35, 3267-3271).

However, the three C-terminal helices terminate at opposite sides of the dimer structure of I-CreI, far away from the N-terminal helices comprising the LAGLIDADG motif (FIG. 1). The length of a flexible linker connecting the C-terminal residue of one domain to the N-terminal residue of the other domain (end to end fusion) would be considerable. Besides engineering such linker would be difficult due to the necessity to go across a large part of the protein surface. Therefore, it is uncertain that proper packing be obtained.

Here the inventor presents a new way to design a single chain molecule derived from the I-CreI homodimeric meganuclease. This strategy preserves the core $\alpha\beta\beta\alpha\beta\beta\alpha$ (also named as $\alpha_1\beta_1\beta_2\alpha_2\beta_3\beta_4\alpha_3$) fold as well as the C-terminal part of the two linked I-CreI units.

This design greatly decreases off-site cleavage and toxicity while enhancing efficacy. The structure and stability of this single-chain molecule are very similar to those of the heterodimeric variants and this molecule appears to be monomeric in solution. Moreover, the resulting proteins trigger highly efficient homologous gene targeting (at the percent level) at an endogenous locus in human cells (SCID gene) in living cells while safeguarding more effectively against potential genotoxicity. In all respects, this single-chain molecule performs as well as I-SceI, the monomeric homing endonuclease considered to be gold standard in terms of specificity. These properties place this new generation of meganucleases among the best molecular scissors available for genome surgery strategies and should facilitate gene correction therapy for monogenetic diseases, such as for example severe combined immunodeficiency (SCID), while potentially avoiding the deleterious effects of previous gene therapy approaches.

The subject matter of the present invention is a single-chain I-CreI meganuclease (scI-CreI) comprising two domains (N-terminal and C-terminal) joined by a peptidic linker, wherein:

(a) each domain, derived from a parent I-CreI monomer, comprises a portion of said parent I-CreI monomer which extends at least from the beginning of the first alpha helix ($\alpha_1$) to the end of the C-terminal loop of I-CreI and includes successively: the $\alpha_1\beta_1\beta_2\alpha_2\beta_3\beta_4\alpha_3$ core domain, the $\alpha_4$ and $\alpha_5$ helices and the C-terminal loop of I-CreI, and (b) the two domains are joined by a peptidic linker which allows said two domains to fold as a I-CreI dimer that is able to bind and cleave a chimeric DNA target comprising one different half of each parent homodimeric I-CreI meganuclease target sequence.

DEFINITIONS

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "meganuclease" is intended an endonuclease having a double-stranded DNA target sequence of 12 to 45 bp. Said meganuclease is either a dimeric enzyme, wherein each domain is on a monomer or a monomeric enzyme comprising the two domains on a single polypeptide. Said meganuclease may be derived from a LAGLIDADG homing endonuclease, for example from I-CreI.

by "meganuclease domain" or "domain" is intended the region which interacts with one half of the DNA target of a meganuclease and is able to associate with the other domain of the same meganuclease which interacts with the other half of the DNA target to form a functional meganuclease able to cleave said DNA target.

by "single-chain meganuclease" is intended a meganuclease comprising two LAGLIDADG homing endonuclease domains linked by a peptidic spacer. The single-chain meganuclease is able to cleave a chimeric DNA target sequence comprising one different half of the two parent meganucleases target sequences. The single-chain meganuclease is also named single-chain derivative, single-chain meganuclease, single-chain meganuclease derivative or chimeric meganuclease.

by "core domain" is intended the "LAGLIDADG homing endonuclease core domain" which is the characteristic $\alpha_1\beta_1\beta_2\alpha_2\beta_3\beta_4\alpha_3$ fold of the homing endonucleases of the LAGLIDADG family, corresponding to a sequence of about one hundred amino acid residues. Said core domain comprises four beta-strands ($\beta_1\beta_2\beta_3\beta_4$) folded in an antiparallel beta-sheet which interacts with one half of the DNA target. This core domain is able to associate with another LAGLIDADG homing endonuclease core domain which interacts with the other half of the DNA target to form a functional endonuclease able to cleave said DNA target. For example, in the case of the dimeric homing endonuclease I-CreI (163 amino acids), the core domain comprises the residues 6 to 94 of I-CreI.

by "beta-hairpin" is intended two consecutive beta-strands of the antiparallel beta-sheet of a LAGLIDADG homing endonuclease core domain ($\beta_1\beta_2$ or $\beta_3\beta_4$) which are connected by a loop or a turn.

by "subdomain" is intended the region of a LAGLIDADG homing endonuclease core domain which interacts with a distinct part of a homing endo-nuclease DNA target half-site.

by "meganuclease variant" or "variant" is intented a meganuclease obtained by replacement of at least one residue in the amino acid sequence of the wild-type meganuclease (natural meganuclease) with a different amino acid.

by "functional variant" is intended a variant which is able to cleave a DNA target sequence, preferably said target is a new target which is not cleaved by the parent meganuclease. For example, such variants have amino acid variation at positions contacting the DNA target sequence or interacting directly or indirectly with said DNA target.

by "meganuclease variant with novel specificity" is intended a variant having a pattern of cleaved targets different from that of the parent meganuclease. The terms "novel specificity", "modified specificity", "novel cleavage specificity", "novel substrate specificity" which are equivalent and used indifferently, refer to the specificity of the variant towards the nucleotides of the DNA target sequence.

by "I-CreI" is intended the wild-type I-CreI (Protein Data Bank accession number 1g9y), corresponding to the sequence SEQ ID NO: 20 in the sequence listing.

by "parent I-CreI monomer" or "I-CreI monomer" is intended the full-length wild-type I-CreI amino acid sequence SEQ ID NO: 20 (163 amino acids) or a functional variant thereof comprising amino acid substitutions in SEQ ID NO: 20. I-CreI functions as a dimer, which is made of two I-CreI monomers.

by "portion of said parent I-CreI monomer which extends at least from the beginning of the first alpha helix to the end of the C-terminal loop of I-CreI and includes successively: the $\alpha_1\beta_1\beta_2\alpha_2\beta_3\beta_4\alpha_3$ core domain, the $\alpha_4$ and $\alpha_5$ helices and the C-terminal loop" is intended the amino acid sequence corresponding to at least positions 8 to 143 of I-CreI.

by "I-CreI site" is intended a 22 to 24 bp double-stranded DNA sequence which is cleaved by I-CreI. I-CreI sites include the wild-type (natural) non-palindromic I-CreI homing site and the derived palindromic sequences such as the sequence 5'-$c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}t_{+10}g_{+11}$ also called C1221 (SEQ ID NO:21; FIG. 3).

by "DNA target", "DNA target sequence", "target sequence", "target-site", "target", "site"; "site of interest"; "recognition site", "recognition sequence", "homing recognition site", "homing site", "cleavage site" is intended a 20 to 24 bp double-stranded palindromic, partially palindromic (pseudo-palindromic) or non-palindromic polynucleotide sequence that is recognized and cleaved by a LAGLIDADG homing endonuclease such as I-CreI, or a variant, or a single-chain chimeric meganuclease derived from I-CreI. These terms refer to a distinct DNA location, preferably a genomic location, at which a double stranded break (cleavage) is to be induced by the meganuclease. The DNA target is defined by the 5' to 3' sequence of one strand of the double-stranded polynucleotide, as indicated above for C1221. Cleavage of the DNA target occurs at the nucleotide positions +2 and −2, respectively for the sense and the antisense strand. Unless otherwise indicated, the position at which cleavage of the DNA target by an I-Cre I meganuclease variant or a single-chain derivative occurs, corresponds to the cleavage site on the sense strand of the DNA target.

by "DNA target half-site", "half cleavage site" or half-site" is intended the portion of the DNA target which is bound by each LAGLIDADG homing endonuclease core domain.

by "chimeric DNA target" or "hybrid DNA target" is intended the fusion of a different half of two parent meganuclease target sequences. In addition at least one half of said target may comprise the combination of nucleotides which are bound by at least two separate subdomains (combined DNA target).

by "chimeric DNA target comprising one different half of each parent homodimeric I-CreI meganuclease target sequence" is intended the target sequence comprising the left part of the palindromic target sequence cleaved by the homodimeric meganuclease made of two identical monomers of one parent monomer and the right part of the palindromic target sequence cleaved by the homodimeric meganuclease made of two identical monomers of the other parent monomer.

by "vector" is intended a nucleic acid molecule capable of transporting another nucleic acid to which it has been linked.

by "homologous" is intended a sequence with enough identity to another one to lead to a homologous recombination between sequences, more particularly having at least 95% identity, preferably 97% identity and more preferably 99%.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

"individual" includes mammals, as well as other vertebrates (e.g., birds, fish and reptiles). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and others such as for example: cows, pigs and horses.

by "mutation" is intended the substitution, deletion, insertion of one or more nucleotides/amino acids in a polynucleotide (cDNA, gene) or a poly-peptide sequence. Said mutation can affect the coding sequence of a gene or its regulatory sequence. It may also affect the structure of the genomic sequence or the structure/stability of the encoded mRNA.

by "site-specific mutation" is intended the mutation of a specific nucleotide/codon in a nucleotidic sequence as opposed to random mutation.

The single-chain I-CreI meganuclease according to the invention is also named, scI-CreI meganuclease or sc-I-CreI.

According to the present invention, the sequence of the linker is chosen so as to allow the two domains of the sc-I-CreI to fold as a I-CreI dimer and to bind and cleave a chimeric DNA target comprising one different half of each parent homodimeric I-CreI meganuclease target sequence.

I-CreI dimer formation may be assayed by well-known assays such as sedimentation equilibrium experiments performed by analytical centrifugation, as previously described in Prieto et al., Nucleic Acids Research, 2007, 35, 3267-3271.

DNA binding may be assayed by well-known assays such as for example, electrophoretic mobility shift assays (EMSA), as previously described in Prieto et al., Nucleic Acids Research, 2007, 35, 3267-3271.

The cleavage activity of the single-chain meganuclease according to the invention may be measured by any well-known, in vitro or in vivo cleavage assay, such as those described in the International PCT Application WO 2004/067736; Epinat et al., Nucleic Acids Res., 2003, 31, 2952-2962; Chames et al., Nucleic Acids Res., 2005, 33, e178; Arnould et al., J. Mol. Biol., 2006, 355, 443-458; Arnould et al., J. Mol. Biol., Epub 10 May 2007.

For example, the cleavage activity of the single-chain meganuclease according to the present invention may be measured by a direct repeat recombination assay, in yeast or mammalian cells, using a reporter vector, by comparison with that of the corresponding heterodimeric meganuclease or of another single-chain meganuclease, derived from identical parent I-CreI monomers. The reporter vector comprises two truncated, non-functional copies of a reporter gene (direct repeats) and the genomic (non-palindromic) DNA target sequence-comprising one different half of each (palindromic or pseudo-palindromic) parent homodimeric I-CreI meganuclease target sequence, within the intervening sequence, cloned in a yeast or a mammalian expression vector. Expression of the meganuclease results in cleavage of the genomic chimeric DNA target sequence. This cleavage induces homologous recombination between the direct repeats, resulting in a functional reporter gene (LacZ, for example), whose expression can be monitored by appropriate assay. In addition, the activity of the single-chain meganuclease towards its genomic DNA target can be compared to that of I-CreI towards the I-CreI site, at the same genomic locus, using a chromosomal assay in mammalian cells (Arnould et al., J. Mol. Biol., Epub 10 May 2007). In addition the specificity of the cleavage by the single-chain meganuclease may be assayed by comparing the cleavage of the chimeric DNA target sequence with that of the two palindromic sequences cleaved by the parent I-CreI homodimeric meganucleases.

The N-terminal sequence of the two domains of the sc-I-CreI may start at position 1, 2, 3, 4, 5, 6 or 8 of I-CreI. In a preferred embodiment, the N-terminal domain starts at position 1 or 6 of I-CreI and the C-terminal domain starts at position 2 or 6 of I-CreI.

The C-terminal sequence of the two domains terminates just after the C-terminal loop, for example at position 143 or 145 of I-CreI. Alternatively, the C-terminal sequence of the domain(s) further includes at least the alpha 6 helix (positions 145 to 150 of I-CreI) and eventually additional C-terminal residues. In this case, the C-terminal sequence of the domain(s) may terminates at position 150, 151, 152, 153, 154, 155, 156, 157, 158, 159, 160, 161, 162 or 163 of I-CreI. Preferably at position 152 to 160. For example at position, 152, 156, 160 or 163. In a preferred embodiment, the N-terminal domain terminates at position 163 of I-CreI. More preferably, both domains terminate at positions 163 of I-CreI.

In another preferred embodiment of the sc-I-CreI meganuclease, the linker comprises or consists of a linear sequence of 10 to 100 consecutive amino acids, preferably 15 to 50 amino acids, more preferably 20 to 35 amino acids, even more preferably 25 to 35 amino acids. The sequence of the linker is predicted to form an helix, either an alpha-helix (prediction made with SOPMA—Self-Optimized Prediction Method with Aligment—Geourjon and Deléage, 1995) or a type II polyproline helix. An example of such polyproline helix is represented by SEQ ID NO: 15 or 16 (Table I). More preferably, the linker comprises an alpha-helix. The linker is advantageously selected from the group consisting of the sequences comprising or consisting of SEQ ID NO: 2 to 19. Preferably, it is selected from the group consisting of the sequences of SEQ ID NO: 2 to 12 and 14 to 19. More preferably, the linker is selected from the group consisting of the sequences 2, 4 to 8, 11, 16, 18 and 19. Even more preferably, the linker consists of the sequence SEQ ID NO: 2.

The single-chain I-CreI meganuclease according to the invention may be derived from wild-type I-CreI monomers or functional variants thereof. In addition, one or more residues inserted at the $NH_2$ terminus and/or COOH terminus of the parent monomers. Additional codons may be added at the 5' or 3' end of the parent monomers to introduce restrictions sites which are used for cloning into various vectors. An example of said sequence is SEQ ID NO: 23 which has an alanine (A) residue inserted after the first methionine residue and an alanine and an aspartic acid (AD) residues inserted after the C-terminal proline residue. These sequences allow having DNA coding sequences comprising the NcoI (ccatgg) and EagI (cggccg) restriction sites which are used for cloning into various vectors. For example, a tag (epitope or polyhistidine sequence) may also be introduced at the $NH_2$ terminus of the N-terminal domain and/or COOH terminus of C-terminal domain; said tag is useful for the detection and/or the purification of said sc-I-CreI meganuclease.

Preferably, the sc-I-CreI meganuclease is derived from the monomers of a heterodimeric I-CreI variant, more preferably of a variant having novel cleavage specificity as previously described (Arnould et al., J. Mol. Biol., 2006, 355, 443-458; Smith et al., Nucleic Acids Res., 2006, 34, e149; Arnould et al., J. Mol. Biol., Epub 10 May 2007; International PCT Applications WO 2006/097784, WO 2006/097853, WO 2007/049095, WO 2007/057781, WO 2007/060495, WO 2007/049156, WO 2007/093836 and WO 2007/093918)

Therefore the domains of the single-chain I-CreI meganuclease may comprise mutations at positions of I-CreI amino acid residues that contact the DNA target sequence or interact with the DNA backbone or with the nucleotide bases, directly or via a water molecule; these residues are well-known in the art (Jurica et al., Molecular Cell., 1998, 2, 469-476; Chevalier et al., J. Mol. Biol., 2003, 329, 253-269). Preferably said mutations modify the cleavage specificity of the meganuclease and result in a meganuclease with novel specificity, which is able to cleave a DNA target from a gene of interest.

More preferably, said mutations are substitutions of one or more amino acids in a first functional subdomain corresponding to that situated from positions 26 to 40 of I-CreI amino acid sequence, that alter the specificity towards the nucleotide at positions ±8 to 10 of the DNA target, and/or substitutions in a second functional subdomain corresponding to that situated from positions 44 to 77 of I-CreI amino acid sequence, that alter the specificity towards the nucleotide at positions ±3 to 5 of the DNA target, as described previously (International PCT Applications WO 2006/097784, WO 2006/097853, WO 2007/060495, WO 2007/049156, WO 2007/049095 and WO 2007/057781; Arnould et al., J. Mol. Biol., 2006, 355, 443-458; Smith et al., Nucleic Acids Res., 2006). The substitutions correspond advantageously to positions 26, 28, 30, 32, 33, 38, and/or 40, 44, 68, 70, 75 and/or 77 of I-CreI amino acid sequence. For cleaving a DNA target, wherein $n_{-4}$ is t or $n_{+4}$ is a, said I-CreI domain has advantageously a glutamine (Q) in position 44; for cleaving a DNA target, wherein $n_4$ is a or $n_{+4}$ is t, said domain has an alanine (A) or an asparagine in position 44, and for cleaving a DNA target, wherein $n_{-9}$ is g or $n_{+9}$ is c, said domain has advantageously an arginine (R) or a lysine (K) in position 38.

According to another preferred embodiment of said scI-CreI meganuclease, at least one domain has mutations at positions 26 to 40 and/or 44 to 77 of I-CreI, said scI-CreI meganuclease being able to cleave a non-palindromic DNA sequence, wherein at least the nucleotides at positions +3 to +5, +8 to +10, −10 to −8 and −5 to −3 of said DNA sequence correspond to the nucleotides at positions +3 to +5, +8 to +10, −10 to −8 and −5 to −3 of a DNA target from a gene of interest. Preferably, both domains of the scI-CreI meganuclease are mutated at positions 26 to 40 and/or 44 to 77. More preferably, both domains have different mutations at positions 26 to 40 and 44 to 77 of I-CreI.

In another preferred embodiment of said scI-CreI meganuclease, at least one domain comprises one or more mutations at positions of other amino acid residues of I-CreI that interact with the DNA target sequence. In particular, additional substitutions may be introduced at positions contacting the phosphate backbone, for example in the final C-terminal loop (positions 137 to 143; Prieto et al., Nucleic Acids Res., 2007, 35, 3262-3271). Preferably said residues are involved in binding and cleavage of said DNA cleavage site. More preferably, said residues are at positions 138, 139, 142 or 143 of I-CreI. Two residues may be mutated in one domain provided that each mutation is in a different pair of residues chosen from the pair of residues at positions 138 and 139 and the pair of residues at positions 142 and 143. The mutations which are introduced modify the interaction(s) of said amino acid(s) of the final C-terminal loop with the phosphate backbone of the I-CreI site. Preferably, the residue at position 138 or 139 is substituted by an hydrophobic amino acid to avoid the formation of hydrogen bonds with the phosphate backbone of the DNA cleavage site. For example, the residue at position 138 is substituted by an alanine or the residue at position 139 is substituted by a methionine. The residue at position 142 or 143 is advantageously substituted by a small amino acid, for example a glycine, to decrease the size of the side chains of these amino acid residues. More preferably, said substitution in the final C-terminal loop modifies the specificity of the scI-CreI meganuclease towards the nucleotide at positions ±1 to 2, ±6 to 7 and/or ±11 to 12 of the I-CreI site.

In another preferred embodiment of said scI-CreI meganuclease, at least one domain comprises one or more additional mutations that improve the binding and/or the cleavage properties, including the cleavage activity and/or specificity of the scI-CreI meganuclease towards the DNA target sequence from a gene of interest. The additional residues which are mutated may be on the entire I-CreI sequence.

According to a more preferred embodiment of said sc-I-CreI meganuclease, said additional mutation(s) impair(s) the formation of functional homodimers from the domains of the sc-I-CreI meganuclease.

Each parent monomer has at least two residues Z and Z' of the dimerisation interface which interact with residues Z' and Z, respectively of the same or another parent monomer (two pairs ZZ' of interacting residues) to form two homodimers and one heterodimer. According to the present invention, one of the two pairs of interacting residues of the dimerisation interface is swapped to obtain a first domain having two residues Z or Z' and a second domain having two residues Z' or Z, respectively. As a result, the first and the second domains each having two residues Z or two residues Z' can less easily homodimerize (inter-sc-I-CreI domains interaction) than their parent counterpart, whereas the presence of two pairs ZZ' of interacting residues at the interface of the two domains of the sc-I-CreI makes the heterodimer formation (intra-sc-I-CreI domains interaction) favourable.

Therefore the domains of the sc-I-CreI meganuclease have advantageously at least one of the following pairs of mutations, respectively for the first (N-terminal or C-terminal domain) and the second domain (C-terminal domain or N-terminal domain):

a) the substitution of the glutamic acid in position 8 with a basic amino acid, preferably an arginine (first domain) and the substitution of the lysine in position 7 with an acidic amino acid, preferably a glutamic acid (second domain); the first domain may further comprise the substitution of at least one of the lysine residues in positions 7 and 96, by an arginine.

b) the substitution of the glutamic acid in position 61 with a basic amino acid, preferably an arginine (first domain) and the substitution of the lysine in position 96 with an acidic amino acid, preferably a glutamic acid (second domain); the first domain may further comprise the substitution of at least one of the lysine residues in positions 7 and 96, by an arginine c) the substitution of the leucine in position 97 with an aromatic amino acid, preferably a phenylalanine (first domain) and the substitution of the phenylalanine in position 54 with a small amino acid, preferably a glycine (second domain); the first domain may further comprise the substitution of the phenylalanine in position 54 by a tryptophane and the second domain may further comprise the substitution of the leucine in position 58 or lysine in position 57, by a methionine, and d) the substitution of the aspartic acid in position 137 with a basic amino acid, preferably an arginine (first domain) and the substitution of the arginine in position 51 with an acidic amino acid, preferably a glutamic acid (second domain).

For example, the first domain may have the mutation D137R and the second domain, the mutation R51D.

Alternatively, the sc-I-CreI meganuclease comprises at least two pairs of mutations as defined in a), b) c) or d), above; one of the pairs of mutation is advantageously as defined in c) or d). Preferably, one domain comprises the substitution of the lysine residues at positions 7 and 96 by an acidic amino acid (D or E) and the other domain comprises the substitution of the glutamic acid residues at positions 8 and 61 by a basic amino acid (K or R). More preferably, the sc-I-CreI meganuclease comprises three pairs of mutations as defined in a), b) and c), above. The sc-I-CreI meganuclease consists advantageously of a first domain (A) having at least the mutations selected from: (i) E8R, E8K or E8H, E61R, E61K or E61H and L97F, L97W or L97Y; (ii) K7R, E8R, E61R, K96R and L97F, or (iii) K7R, E8R, F54W, E61R, K96R and L97F and a second domain (B) having at least the mutations (iv) K7E or K7D, F54G or F54A and K96D or K96E; (v) K7E, F54G, L58M and K96E, or (vi) K7E, F54G, K57M and K96E.

Another example of mutations that impair the formation of functional homodimers from the domains of the sc-I-CreI meganuclease is the G19S mutation. The G19S mutation is advantageously introduced in one of the two domains of the sc-I-CreI meganuclease, so as to obtain a single-chain meganuclease having enhanced cleavage activity and enhanced cleavage specificity. In addition, to enhance the cleavage specificity further, the other domain or both domains may carry distinct mutation(s) that impair the formation of a functional homodimer or favors the formation of the heterodimeric sc-I-CreI meganuclease, as defined above. For example, one monomer comprises the G19S mutation and the K7E and K96E or the E8K and E61R mutations and the other monomer comprises the E8K and E61R or the K7E and K96E mutations, respectively.

In another preferred embodiment of said sc-I-CreI meganuclease, said mutations are replacement of the initial amino acids with amino acids selected from the group consisting of: A, D, E, G, H, K, N, P, Q, R, S, T, Y, C, V, L and W.

The subject-matter of the present invention is also a sc-I-CreI meganuclease comprising the sequence SEQ ID NO: 95 or 97; these sc-I-CreI meganucleases cleave the RAG1 target (RAG1.10; SEQ ID NO: 41 and FIG. 16) which is present in the human RAG1 gene. This sc-I-CreI meganuclease can be used for repairing RAG1 mutations associated with a SCID syndrome or for genome engineering at the RAG1 gene loci. Since RAG1.10 is upstream of the coding sequence (FIG. 16), these sc-I-CreI meganucleases can be used for repairing any mutation in the RAG1 gene by exon knock-in, as described in the International PCT Application WO 2008/010093).

The subject-matter of the present invention is also a polynucleotide fragment encoding a single-chain meganuclease as defined above. According to a preferred embodiment of said polynucleotide, the nucleic acid sequences encoding the two I-CreI domains of said single-chain meganuclease have less than 80% nucleic sequence identity, preferably less than 70% nucleic sequence identity. This reduces the risk of recombination between the two sequences and as a result, the genetic stability of the polynucleotide construct and the derived vector is thus increased. This may be obtained by rewriting the I-CreI sequence using the codon usage and the genetic code degeneracy. For example, one of the domains is derived from the wild-type I-CreI coding sequence (SEQ ID NO: 22) and the other domain is derived from a rewritten version of the I-CreI coding sequence (SEQ ID NO: 24). Furthermore the codons of the cDNAs encoding the single-chain meganuclease are chosen to favour the expression of said proteins in the desired expression system.

The subject-matter of the present invention is also a recombinant vector for the expression of a single-chain meganuclease according to the invention. The recombinant vector comprises at least one polynucleotide fragment encoding a single-chain meganuclease, as defined above.

A vector which can be used in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

Preferred vectors include lentiviral vectors, and particularly self inactivating lentiviral vectors.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1, URA3 and LEU2 for S. cerevisiae; tetracycline, rifampicin or ampicillin resistance in E. coli.

Preferably said vectors are expression vectors, wherein the sequence(s) encoding the single-chain meganuclease of the invention is placed under control of appropriate transcriptional and translational control elements to permit production or synthesis of said meganuclease. Therefore, said polynucleotide is comprised in an expression cassette. More particularly, the vector comprises a replication origin, a promoter operatively linked to said encoding polynucleotide, a ribosome-binding site, an RNA-splicing site (when genomic DNA is used), a polyadenylation site and a transcription termination site. It also can comprise an enhancer. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

According to another advantageous embodiment of said vector, it includes a targeting construct comprising sequences sharing homologies with the region surrounding the genomic DNA cleavage site as defined above.

Alternatively, the vector coding for the single-chain meganuclease and the vector comprising the targeting construct are different vectors.

More preferably, the targeting DNA construct comprises:
a) sequences sharing homologies with the region surrounding the genomic DNA cleavage site as defined above, and
b) a sequence to be introduced flanked by sequences as in a).

Preferably, homologous sequences of at least 50 bp, preferably more than 100 bp and more preferably more than 200 bp are used. Therefore, the targeting DNA construct is preferably from 200 pb to 6000 pb, more preferably from 1000 pb to 2000 pb. Indeed, shared DNA homologies are located in regions flanking upstream and downstream the site of the break and the DNA sequence to be introduced should be located between the two arms. The sequence to be introduced is preferably a sequence which repairs a mutation in the gene of interest (gene correction or recovery of a functional gene), for the purpose of genome therapy. Alternatively, it can be any other sequence used to alter the chromosomal DNA in some specific way including a sequence used to modify a specific sequence, to attenuate or activate the gene of interest, to inactivate or delete the gene of interest or part thereof, to introduce a mutation into a site of interest or to introduce an exogenous gene or part thereof. Such chromosomal DNA alterations are used for genome engineering (animal models/human recombinant cell lines).

The invention also concerns a prokaryotic or eukaryotic host cell which is modified by a polynucleotide or a vector as defined above, preferably an expression vector.

The invention also concerns a non-human transgenic animal or a transgenic plant, characterized in that all or part of their cells are modified by a polynucleotide or a vector as defined above.

As used herein, a cell refers to a prokaryotic cell, such as a bacterial cell, or eukaryotic cell, such as an animal, plant or yeast cell.

The subject-matter of the present invention is further the use of a meganuclease, a polynucleotide, preferably included in an expression vector, a cell, a transgenic plant, a non-human transgenic mammal, as defined above, for molecular biology, for in vivo or in vitro genetic engineering, and for in vivo or in vitro genome engineering, for non-therapeutic purposes.

Molecular biology includes with no limitations, DNA restriction and DNA mapping. Genetic and genome engineering for non therapeutic purposes include for example (i) gene targeting of specific loci in cell packaging lines for protein production, (ii) gene targeting of specific loci in crop plants, for strain improvements and metabolic engineering, (iii) targeted recombination for the removal of markers in genetically modified crop plants, (iv) targeted recombination for the removal of markers in genetically modified microorganism strains (for antibiotic production for example).

According to an advantageous embodiment of said use, it is for inducing a double-strand break in a site of interest comprising a DNA target sequence, thereby inducing a DNA recombination event, a DNA loss or cell death.

According to the invention, said double-strand break is for: repairing a specific sequence, modifying a specific sequence, restoring a functional gene in place of a mutated one, attenuating or activating an endogenous gene of interest, introducing a mutation into a site of interest, introducing an exogenous gene or a part thereof, inactivating or detecting an endogenous gene or a part thereof, translocating a chromosomal arm, or leaving the DNA unrepaired and degraded.

The subject-matter of the present invention is also a method of genetic engineering, characterized in that it comprises a step of double-strand nucleic acid breaking in a site of interest located on a vector comprising a DNA target as defined hereabove, by contacting said vector with a meganuclease as defined above, thereby inducing an homologous recombination with another vector presenting homology with the sequence surrounding the cleavage site of said meganuclease.

The subject-matter of the present invention is also a method of genome engineering, characterized in that it comprises the following steps: 1) double-strand breaking a genomic locus comprising at least one DNA target of a meganuclease as defined above, by contacting said target with said meganuclease; 2) maintaining said broken genomic locus under conditions appropriate for homologous recombination with a targeting DNA construct comprising the sequence to be introduced in said locus, flanked by sequences sharing homologies with the targeted locus.

The subject-matter of the present invention is also a method of genome engineering, characterized in that it comprises the following steps: 1) double-strand breaking a genomic locus comprising at least one DNA target of a meganuclease as defined above, by contacting said cleavage site with said meganuclease; 2) maintaining said broken genomic locus under conditions appropriate for homologous recombination with chromosomal DNA sharing homologies to regions surrounding the cleavage site.

The subject-matter of the present invention is also the use of at least one meganuclease as defined above, one or two derived polynucleotide(s), preferably included in expression vector(s), as defined above, for the preparation of a medicament for preventing, improving or curing a genetic disease in an individual in need thereof, said medicament being administrated by any means to said individual.

The subject-matter of the present invention is also a method for preventing, improving or curing a genetic disease in an individual in need thereof, said method comprising the step of administering to said individual a composition comprising at least a meganuclease as defined above, by any means.

In this case, the use of the meganuclease as defined above, comprises at least the step of (a) inducing in somatic tissue(s) of the individual a double stranded cleavage at a site of interest of a gene comprising at least one recognition and cleavage site of said meganuclease, and (b) introducing into the individual a targeting DNA, wherein said targeting DNA comprises (1) DNA sharing homologies to the region surrounding the cleavage site and (2) DNA which repairs the site of interest upon recombination between the targeting DNA and the chromosomal DNA. The targeting DNA is introduced into the individual under conditions appropriate for introduction of the targeting DNA into the site of interest.

According to the present invention, said double-stranded cleavage is induced, either in toto by administration of said meganuclease to an individual, or ex vivo by introduction of said meganuclease into somatic cells removed from an individual and returned into the individual after modification.

In a preferred embodiment of said use, the meganuclease is combined with a targeting DNA construct comprising a sequence which repairs a mutation in the gene flanked by sequences sharing homologies with the regions of the gene surrounding the genomic DNA cleavage site of said meganuclease, as defined above. The sequence which repairs the mutation is either a fragment of the gene with the correct sequence or an exon knock-in construct.

For correcting a gene, cleavage of the gene occurs in the vicinity of the mutation, preferably, within 500 bp of the mutation. The targeting construct comprises a gene fragment which has at least 200 bp of homologous sequence flanking the genomic DNA cleavage site (minimal repair matrix) for repairing the cleavage, and includes the correct sequence of the gene for repairing the mutation. Consequently, the targeting construct for gene correction comprises or consists of the minimal repair matrix; it is preferably from 200 pb to 6000 pb, more preferably from 1000 pb to 2000 pb.

For restoring a functional gene, cleavage of the gene occurs upstream of a mutation. Preferably said mutation is the first known mutation in the sequence of the gene, so that all the downstream mutations of the gene can be corrected simultaneously. The targeting construct comprises the exons downstream of the genomic DNA cleavage site fused in frame (as in the cDNA) and with a polyadenylation site to stop transcription in 3'. The sequence to be introduced (exon knock-in construct) is flanked by introns or exons sequences surrounding the cleavage site, so as to allow the transcription of the engineered gene (exon knock-in gene) into a mRNA able to code for a functional protein. For example, the exon knock-in construct is flanked by sequences upstream and downstream.

The subject-matter of the present invention is also the use of at least one meganuclease as defined above, one polynucleotide, preferably included in an expression vector, as defined above for the preparation of a medicament for preventing, improving or curing a disease caused by an infectious agent that presents a DNA intermediate, in an individual in need thereof, said medicament being administrated by any means to said individual.

The subject-matter of the present invention is also a method for preventing, improving or curing a disease caused by an infectious agent that presents a DNA intermediate, in an individual in need thereof, said method comprising at least the step of administering to said individual a composition as defined above, by any means.

The subject-matter of the present invention is also the use of at least one meganuclease as defined above, one polynucleotide, preferably included in an expression vector, as defined above, in vitro, for inhibiting the propagation, inactivating or deleting an infectious agent that presents a DNA intermediate, in biological derived products or products intended for biological uses or for disinfecting an object.

The subject-matter of the present invention is also a method for decontaminating a product or a material from an infectious agent that presents a DNA intermediate, said method comprising at least the step of contacting a biological derived product, a product intended for biological use or an object, with a composition as defined above, for a time sufficient to inhibit the propagation, inactivate or delete said infectious agent.

In a particular embodiment, said infectious agent is a virus. For example said virus is an adenovirus (Ad11, Ad21), herpesvirus (HSV, VZV, EBV, CMV, herpesvirus 6, 7 or 8), hepadnavirus (HBV), papovavirus (HPV), poxvirus or retrovirus (HTLV, HIV).

The subject-matter of the present invention is also a composition characterized in that it comprises at least one meganuclease, one polynucleotide, preferably included in an expression vector, as defined above.

In a preferred embodiment of said composition, it comprises a targeting DNA construct comprising the sequence which repairs the site of interest flanked by sequences sharing homologies with the targeted locus as defined above. Preferably, said targeting DNA construct is either included in a recombinant vector or it is included in an expression vector comprising the polynucleotide encoding the meganuclease, as defined in the present invention.

The subject-matter of the present invention is also products containing at least a meganuclease, one expression vector encoding said meganuclease, and a vector including a targeting construct, as defined above, as a combined preparation for simultaneous, separate or sequential use in the prevention or the treatment of a genetic disease.

For purposes of therapy, the meganuclease and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of the targeted disease and in a genome correction of the lesion or abnormality.

In one embodiment of the uses according to the present invention, the meganuclease is substantially non-immunogenic, i.e., engenders little or no adverse immunological response. A variety of methods for ameliorating or eliminating deleterious immunological reactions of this sort can be used in accordance with the invention. In a preferred embodiment, the meganuclease is substantially free of N-formyl methionine. Another way to avoid unwanted immunological reactions is to conjugate meganucleases to polyethylene glycol ("PEG") or polypropylene glycol ("PPG") (preferably of 500 to 20,000 daltons average molecular weight (MW)). Conjugation with PEG or PPG, as described by Davis et al. (U.S. Pat. No. 4,179,337) for example, can provide non-immunogenic, physiologically active, water soluble endo-nuclease conjugates with anti-viral activity. Similar methods also using a polyethylene-polypropylene glycol copolymer are described in Saifer et al. (U.S. Pat. No. 5,006,333).

The meganuclease can be used either as a polypeptide or as a polynucleotide construct/vector encoding said polypeptide. It is introduced into cells, in vitro, ex vivo or in vivo, by any convenient means well-known to those in the art, which are appropriate for the particular cell type, alone or in association with either at least an appropriate vehicle or carrier and/or with the targeting DNA. Once in a cell, the meganuclease and if present, the vector comprising targeting DNA and/or nucleic acid encoding a meganuclease are imported or translocated by the cell from the cytoplasm to the site of action in the nucleus.

The meganuclease (polypeptide) may be advantageously associated with: liposomes, polyethyleneimine (PEI), and/or membrane translocating peptides (Bonetta, The Scientist, 2002, 16, 38; Ford et al., Gene Ther., 2001, 8, 1-4; Wadia and Dowdy, Curr. Opin. Biotechnol., 2002, 13, 52-56); in the latter case, the sequence of the meganuclease fused with the sequence of a membrane translocating peptide (fusion protein).

Vectors comprising targeting DNA and/or nucleic acid encoding a meganuclease can be introduced into a cell by a variety of methods (e.g., injection, direct uptake, projectile bombardment, liposomes, electroporation). Meganucleases can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). Optionally, it may be preferable to incorporate a nuclear localization signal into the recombinant protein to be sure that it is expressed within the nucleus.

The subject-matter of the present invention is also the use of at least one meganuclease, as defined above, as a scaffold for making other meganucleases. For example other rounds of mutagenesis and selection/screening can be performed on the single-chain meganuclease, for the purpose of making novel homing endonucleases.

The uses of the meganuclease and the methods of using said meganucleases according to the present invention include also the use of the poly-nucleotide, vector, cell, transgenic plant or non-human transgenic mammal encoding said meganuclease, as defined above.

According to another advantageous embodiment of the uses and methods according to the present invention, said meganuclease, polynucleotide, vector, cell, transgenic plant or non-human transgenic mammal are associated with a targeting DNA construct as defined above. Preferably, said vector encoding the meganuclease, comprises the targeting DNA construct, as defined above.

Methods for making I-CreI variants having novel cleavage specificity have been described previously (Epinat et al., Nucleic Acids Res., 2003, 31, 2952-2962; Chames et al., Nucleic Acids Res., 2005, 33, e178, and Arnould et al., J. Mol. Biol., 2006, 355, 443-458; Smith et al., Nucleic Acids Res., 2006, 34, e149; Arnould et al., J. Mol. Biol., Epub 10 May 2007; International PCT Applications WO 2004/067736, WO 2006/097784, WO 2006/097853, WO 2007/049095, WO 2007/057781, WO 2007/060495, WO 2007/049156, WO 2007/093836, WO 2007/093918, WO2008/010009, WO2008/010093, WO2008/059317, WO2008/059382, WO2008/093152, WO2008/093249, WO2008/02198, WO2008/02199, WO2008/02274, WO2008/149176, WO2008/152523, WO2008/152524 and WO2009/001159). The single-chain meganuclease of the invention may be derived from I-CreI or functional variants thereof by using well-known recombinant DNA and genetic engineering techniques. For example, a sequence comprising the linker coding sequence in frame with, either the 3' end of the N-terminal domain coding sequence or the 5' end of the C-terminal domain coding sequence is amplified from a DNA template, by polymerase chain reaction with specific primers. The PCR fragment is then cloned in a vector comprising the sequence encoding the other domain by using appropriate restriction sites. The single-chain meganuclease as defined in the present invention is produced by expressing the polypeptide as defined above; preferably said polypeptide is expressed in a host cell or a transgenic animal/plant modified by one expression vector, under conditions suitable for the expression of the polypeptide, and the single-chain meganuclease derivative is recovered from the host cell culture or from the transgenic animal/plant.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In addition to the preceding features, the invention further comprises other features which will emerge from the description which follows, which refers to examples illustrating the single-chain I-CreI meganuclease of the present invention and its uses according to the invention, as well as to the appended drawings in which:

FIG. 1 is a Cα ribbon representation of I-CreI.

FIG. 2 is a schematic representation of the human XPC gene (GenBank accession number NC_000003). The XPC exons are boxed. The XPC4.1 (or C1: SEQ ID NO: 26) sequence (position 20438) is situated in Exon 9.

FIG. 3 represents 22 bp DNA targets cleaved by I-CreI or some of its derived variants (SEQ ID NO: 21, 27 to 29, 26, 30 and 31 respectively). C1221 is the I-CreI target. 10GAG_P, 10GTA_P and 5TCT_P are palindromic targets, which differ from C1221 by the boxed motifs. C1 is the XPC target; C3 and C4 are palindromic targets, which are derived respectively from the left and the right part of C1. As shown in the Figure, the boxed motifs from 10GAG_P, 10GTA_P and 5TCT_P are found in the C1 target.

FIG. 4 illustrates the C1 target cleavage by heterodimeric combinatorial mutants. The figure displays secondary screening of combinations of C3 and C4 cutters with the C1 target. The H33 mutant is among seven C3 cutters, X2 is among eight C4 cutters and the cleavage of the C1 target by the X2/H33 heterodimer is circled in black.

Figure 7:
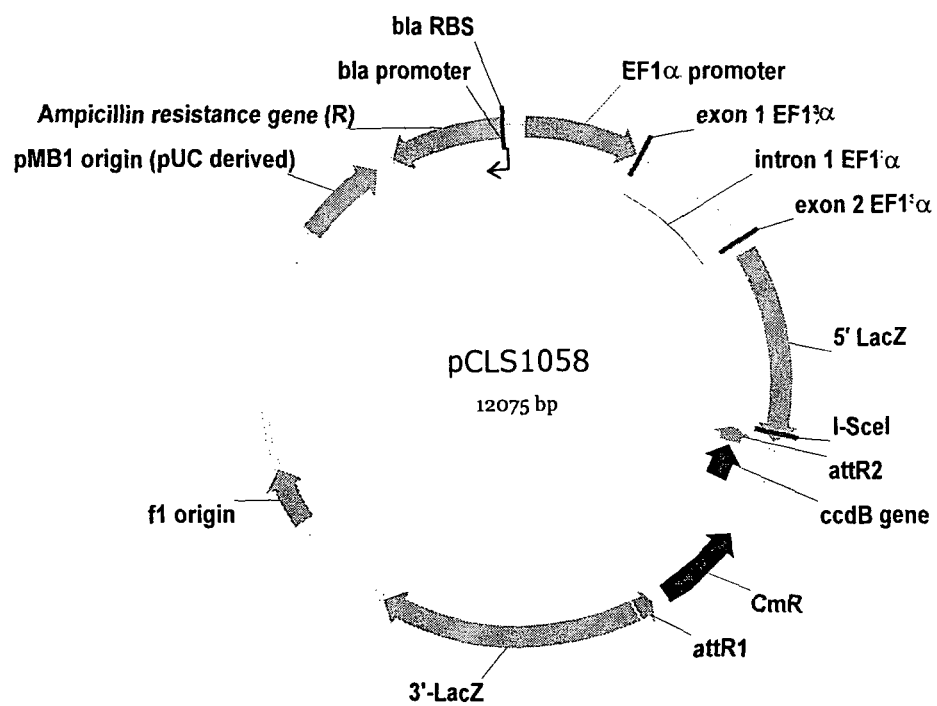
Figure 8:
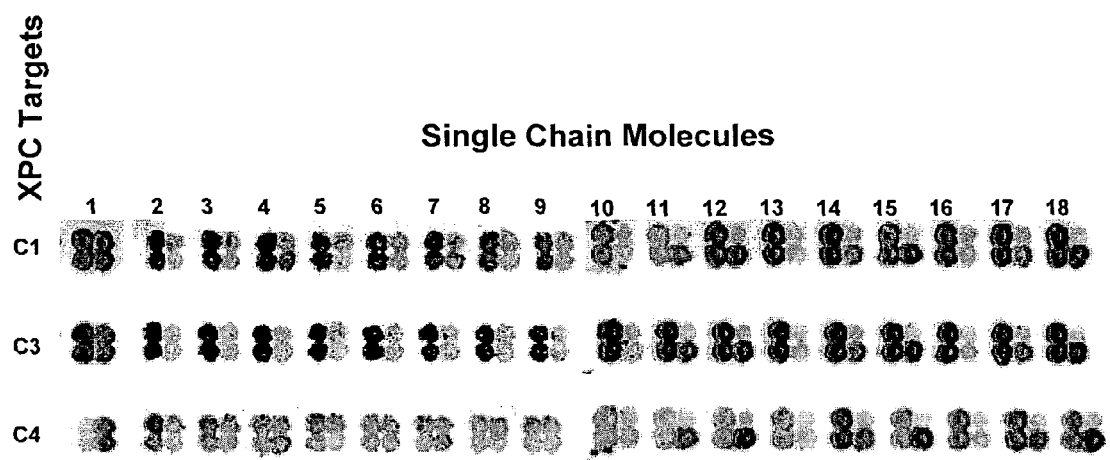

FIG. 7 represents the pCLS1058 reporter vector map. The reporter vector is marked with blasticidine and ampicilline resistance genes. The LacZ tandem repeats share 800 bp of homology, and are separated by 1.3 kb of DNA. They are surrounded by EF1-alpha promoter and terminator sequences. Target sites are cloned using the Gateway protocol (INVITROGEN), resulting in the replacement of the CmR and ccdB genes with the chosen target site FIG. 8 illustrates the yeast screening of the eighteen single chain constructs against the three XPC targets C1, C3 and C4. Each single chain molecule is referred by its number described in Table I. For each four dots yeast cluster, the two left dots are the result of the experiment, while the two right dots are various internal controls to assess the experiment quality and validity.

Figure 9:
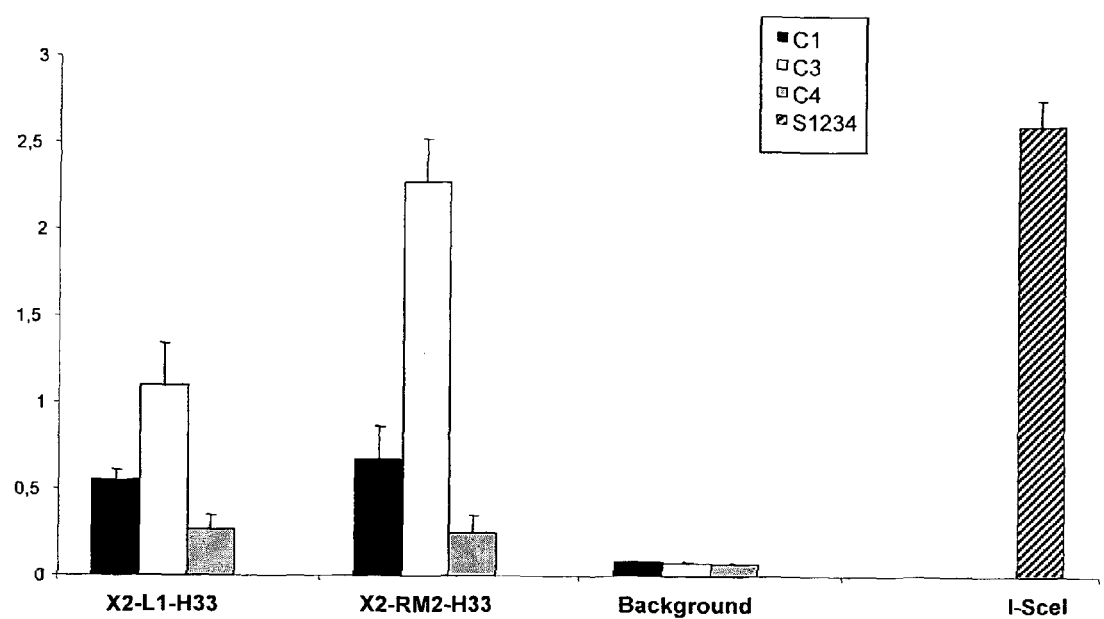

FIG. 9 illustrates the cleavage of the C1, C3 and C4 XPC targets by the two X2-L1-H33 and X2-RM2-H33 single chain constructs in an extrachromosomal assay in CHO cells. Background corresponds to the transfection of the cells with an empty expression vector. Cleavage of the S1234 I-SceI target by I-SceI in the same experiment is shown as a positive control.

Figure 10:
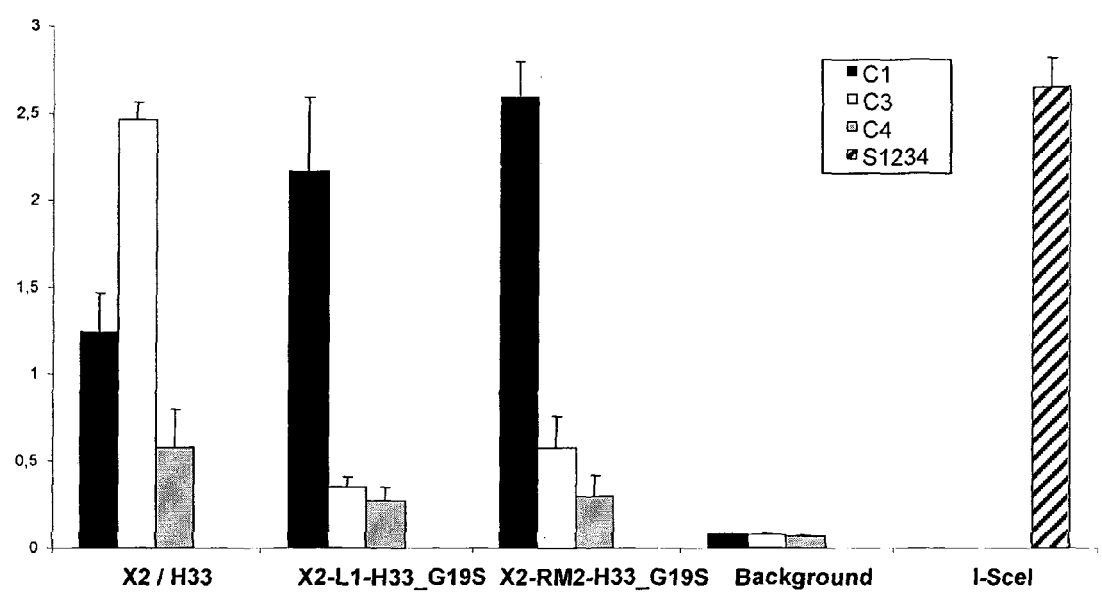

FIG. 10 illustrates the cleavage of the C1, C3 and C4 XPC targets by the X2/H33 heterodimer and the two X2-L1-H33$_{G19S}$ and X2-RM2-H33$_{G19S}$ single chain constructs in an extrachromosomal assay in CHO cells. Background corresponds to the transfection of the cells with an empty expression vector. Cleavage of the S1234 I-SceI target by I-SceI in the same experiment is shown as a positive control.

Figure 11:
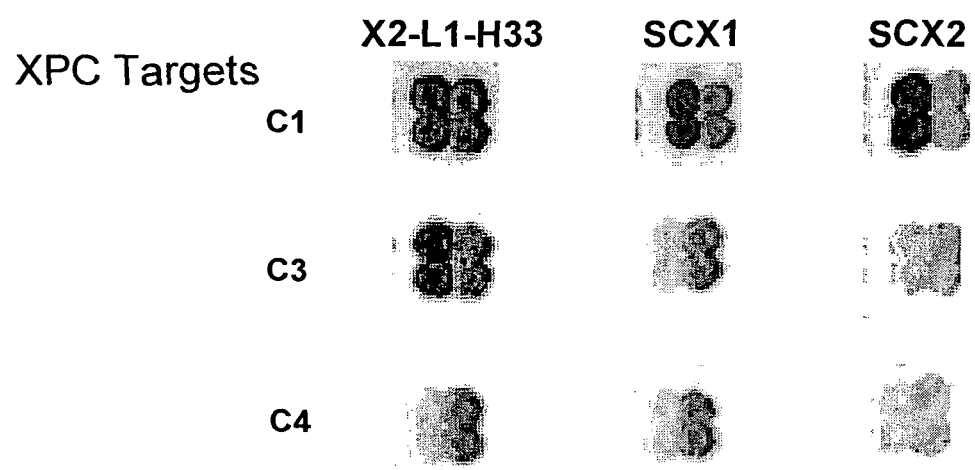

FIG. 11 illustrates the yeast screening of three XPC single chain molecules X2-L1-H33, SCX1 and SCX2 against the three XPC targets (C1, C3 and C4). SCX1 is the X2(K7E)-L1-H33(E8K,G19S) molecule and SCX2 stands for the X2(E8K)-L1-H33(K7E,G19S) molecule. For each four dots yeast cluster, the two left dots are the result of the experiment, while the two right dots are various internal controls to assess the experiment quality and validity.

Figure 12:
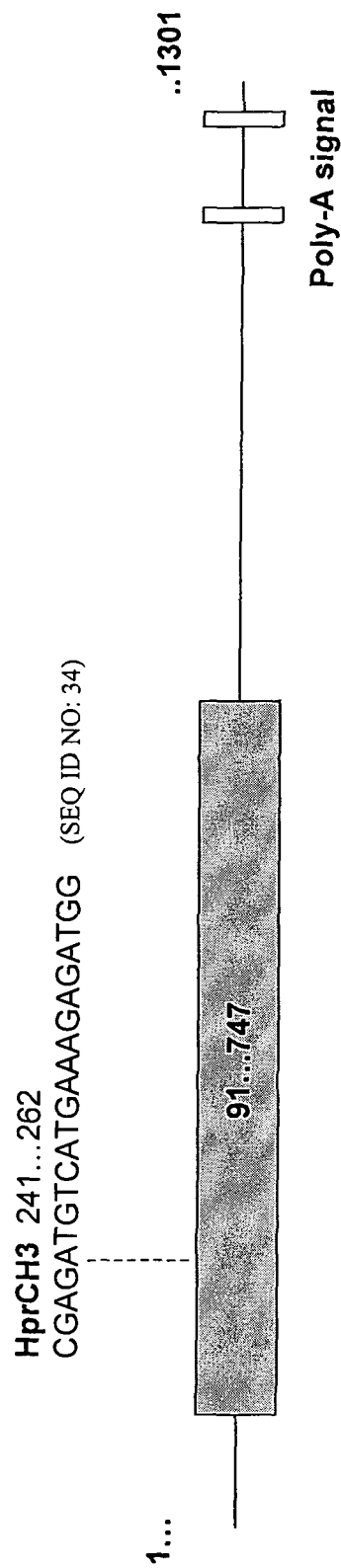

FIG. 12 is a schematic representation of the *Cricetulus griseus* Hypoxanthine-Guanine Phosphoribosyl Transferase (HPRT) mRNA (GenBank accession number J00060.1). The ORF is indicated as a grey box. The HprCH3 target site is indicated with its sequence (SEQ ID NO: 34) and position.

FIG. 13 represents 22 bp DNA targets cleaved by I-CreI or some of its derived variants (SEQ ID NO: 21, 27 and 32 to 36, respectively). C1221 is the I-CreI target. 10GAG_P, 10CAT_P and 5CTT_P are palindromic targets, which differ from C1221 by the boxed motifs. HprCH3 is the HPRT target, HprCH3.3 and HprCH3.4 are palindromic targets, which are derived respectively from the left and the right part of HprCH3. As shown in the Figure, the boxed motifs from 10GAG_P, 10CAT_P and 5CTT_P are found in the HprCH3 target.

Figure 14:
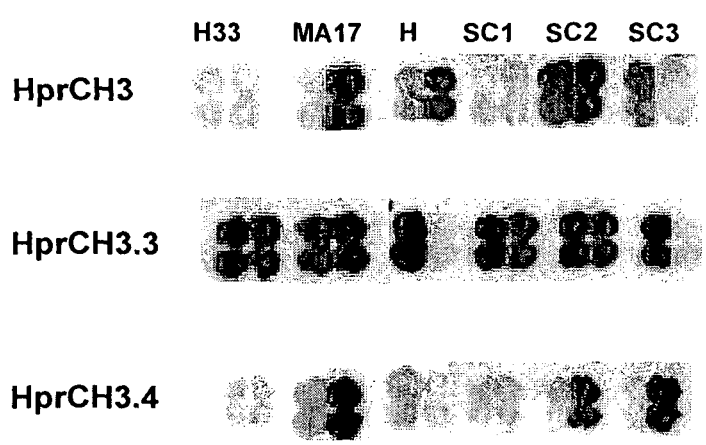

FIG. 14 illustrates the yeast screening of the MA17 and H33 homodimer, of the HPRT heterodimer and of three HPRT single chain molecules against the three HPRT targets HprCH3, HprCH3.3 and HprCH3.4. H is the MA17/H33 heterodimer. Since it results from co-expression of MA17 and H33, there are actually three molecular species in the yeast: the two MA17 and H33 homodimers, together with the MA17/H33 heterodimer. Homodimer formation accounts for cleavage of the HprCH3.3 and HprCH3.4 targets. SC1 to SC3 are MA17-L1-H33, MA17-L1-H33$_{G19S}$ and MA17-RM2-H33, respectively. For each four dots yeast cluster, the two left dots are the result of the experiment, while the two right dots are various internal controls to assess the experiment quality and validity.

Figure 15:
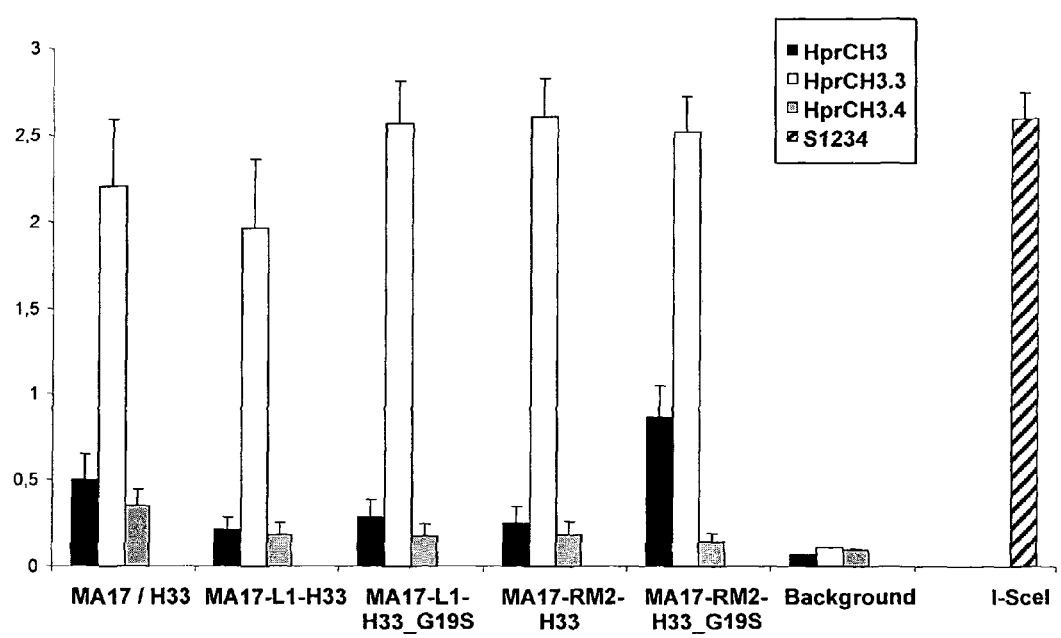

FIG. 15 illustrates the cleavage of the HprCH3, HprCH3.3 and HprCH3.4 HPRT targets by the MA17/H33 heterodimer and the four HPRT single chain constructs (MA17-L1-H33, MA17-L1-H33$_{G19S}$, MA17-RM2-H33 and MA17-RM2-H33$_{G19S}$) in an extrachromosomal assay in CHO cells. Background corresponds to the transfection of the cells with an empty expression vector. Cleavage of the S1234 I-SceI target by I-SceI in the same experiment is shown as a positive control.

Figure 16:
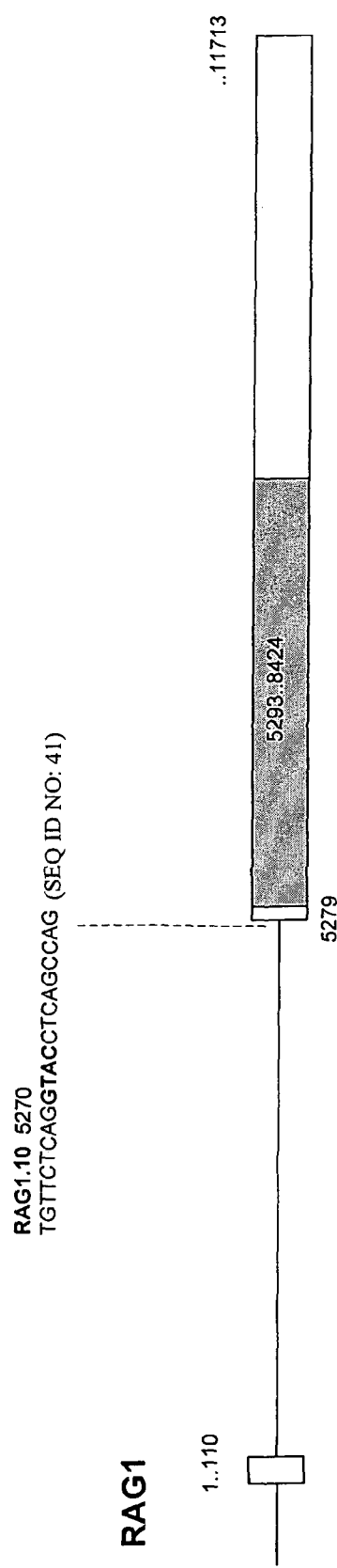

FIG. 16 is a schematic representation of the human RAG1 gene (GenBank accession number NC_000011). Exonic sequences are boxed, and the Exon-Intron junctions are indicated. ORF is indicated as a grey box. The RAG1.10 sequence is indicated with its sequence (SEQ ID NO: 41) and position.

FIG. 17 represents 22 bp DNA targets cleaved by I-CreI or some of its derived variants (SEQ ID NO: 21 and 37 to 43, respectively). C1221 is the I-CreI target. 10GTT_P, 5CAG_P, 10TGG_P and 5GAG_P are palindromic targets, which differ from C1221 by the boxed motifs. RAG1.10 is the RAG1 target, RAG1.10.2 and RAG1.10.3 are palindromic targets, which are derived from the left and the right part of RAG1.10, respectively. As shown in the Figure, the boxed motifs from 10GTT_P, 5CAG_P, 10TGG_P and 5GAG_P are found in the RAG1.10 target.

Figure 18:
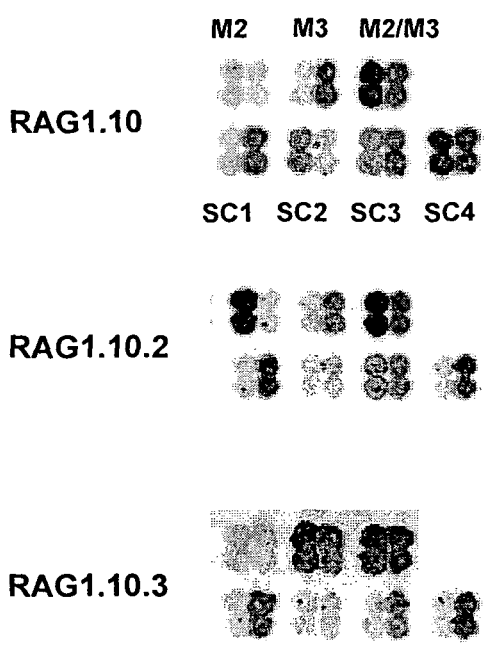

FIG. 18 illustrates the yeast screening of the four RAG1 single chain molecules against the three RAG1 targets RAG1.10, RAG1.10.2 and RAG1.10.3. SC1 to SC4 represent M2-L1-M3, M2$_{G19S}$-L1-H33, M2-RM2-M3 and M2$_{G19S}$-RM2-M3, respectively. Activity of the M2 and M3 I-CreI mutants and the M2/M3 heterodimer against the three RAG1 targets is also shown. For each four dots yeast cluster, the two left dots are the result of the experiment, while the two right dots are various internal controls to assess the experiment quality and validity.

Figure 19:
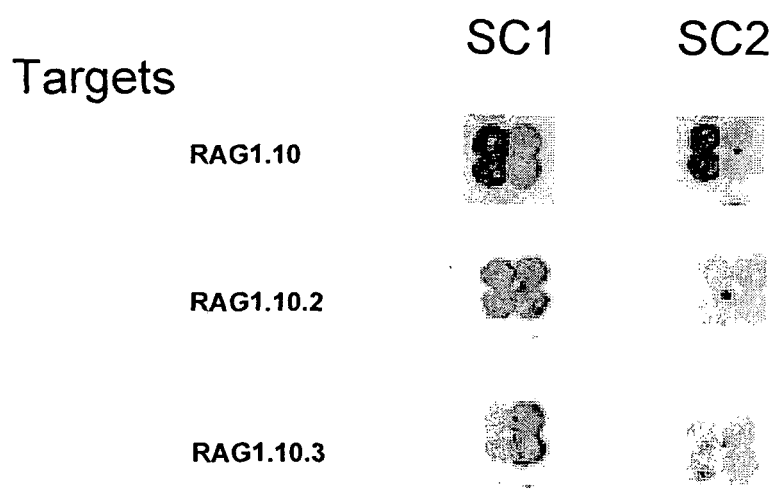

FIG. 19 illustrates the yeast screening of two single chain molecules SC1 and SC2 against the three RAG1.10 targets. SC1 is the M3-RM2-M2 molecule and SC2 stands for the M3(K7E K96E)-RM2-M2(E8K E61R) molecule. For each 4 dots yeast cluster, the two left dots are the result of the experiment, while the two right dots are various internal controls to assess the experiment quality and validity.

Figure 20:
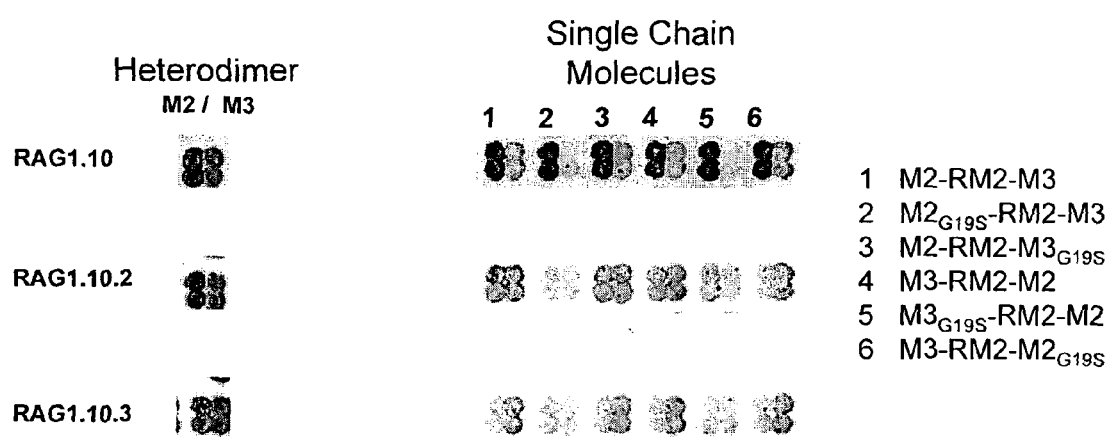

FIG. 20 illustrates the yeast screen of six RAG1 single chain molecules against the three RAG1 targets RAG1.10, RAG1.10.2 and RAG1.10.3. Activity of the M2/M3 heterodimer against the three RAG1 targets is also shown. For each 4 dots yeast cluster, the two left dots are the result of the experiment, while the two right dots are various internal controls to assess the experiment quality and validity.

Figure 21:
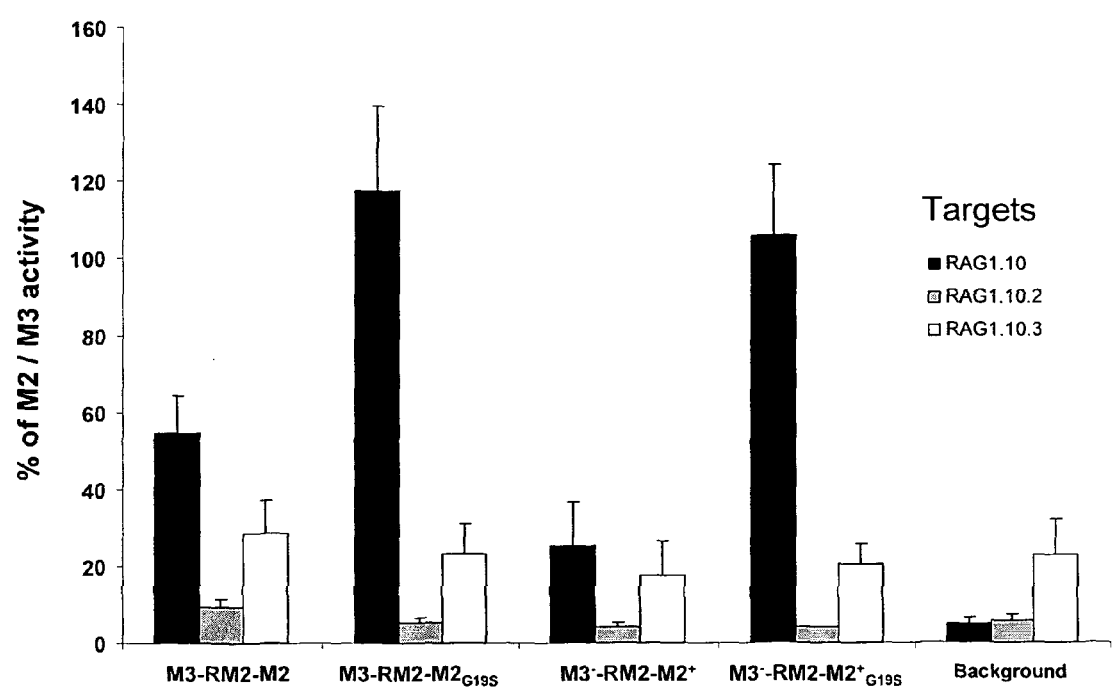

FIG. 21 illustrates the cleavage of the RAG1.10, RAG1.10.2 and RAG1.10.3 targets by four single chain constructs in an extrachromosomal assay in CHO cells. Background corresponds to the transfection of the cells with an empty expression vector. Results are expressed in percentage of the activity of the M2/M3 heterodimer against the same three targets.

FIG. 22 illustrates: A. Principle of the chromosomal assay in CHO cells. B. Gene correction activity of the M2/M3 heterodimer and the two single chain molecules M3-RM2-M2$_{G19S}$ and M3$^-$-RM2-M2$^+_{G19S}$. The frequency of LacZ positive cells is represented in function of the amount of transfected expression plasmid.

Figure 23:
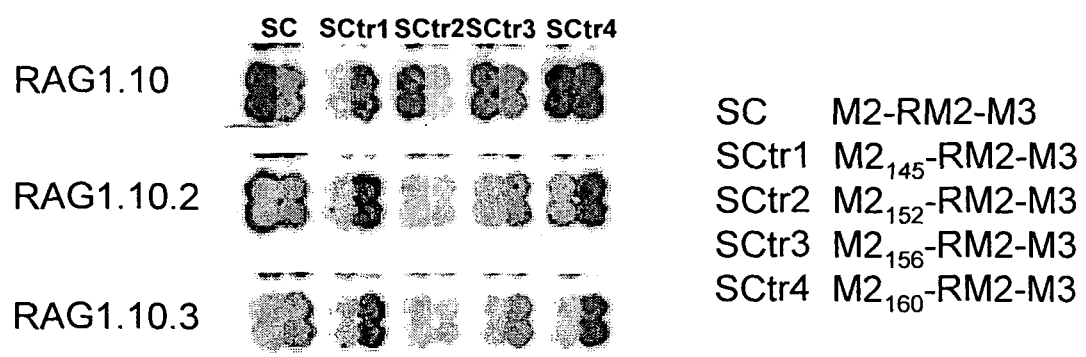

FIG. 23 illustrates the activity of five single chain molecules against the three RAG1.10, RAG1.10.2 and RAG1.10.3 targets. In each yeast cluster, the two left dots are a single chain molecule, while the two right dots are experiment internal controls.

Figure 24:
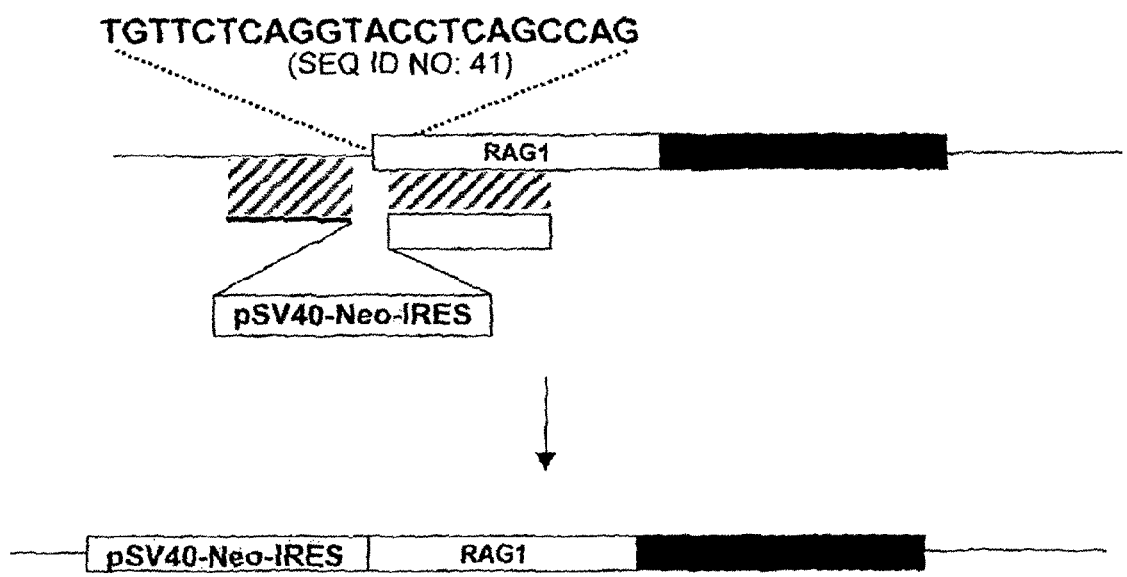

FIG. 24 is a diagram of the gene targeting strategy used at the endogenous RAG1 locus. The RAG1 target sequence (RAG1.10: SEQ ID NO: 41) is located just upstream of exon 2 coding for the Rag1 protein. Exon 2 is boxed, with the open reading frame in white. Cleavage of the native RAG1 gene by the meganuclease yields a substrate for homologous recombination, which may use the repair matrix containing 1.7 kb of exogenous DNA flanked by homology arms as a repair matrix.

Figure 25:
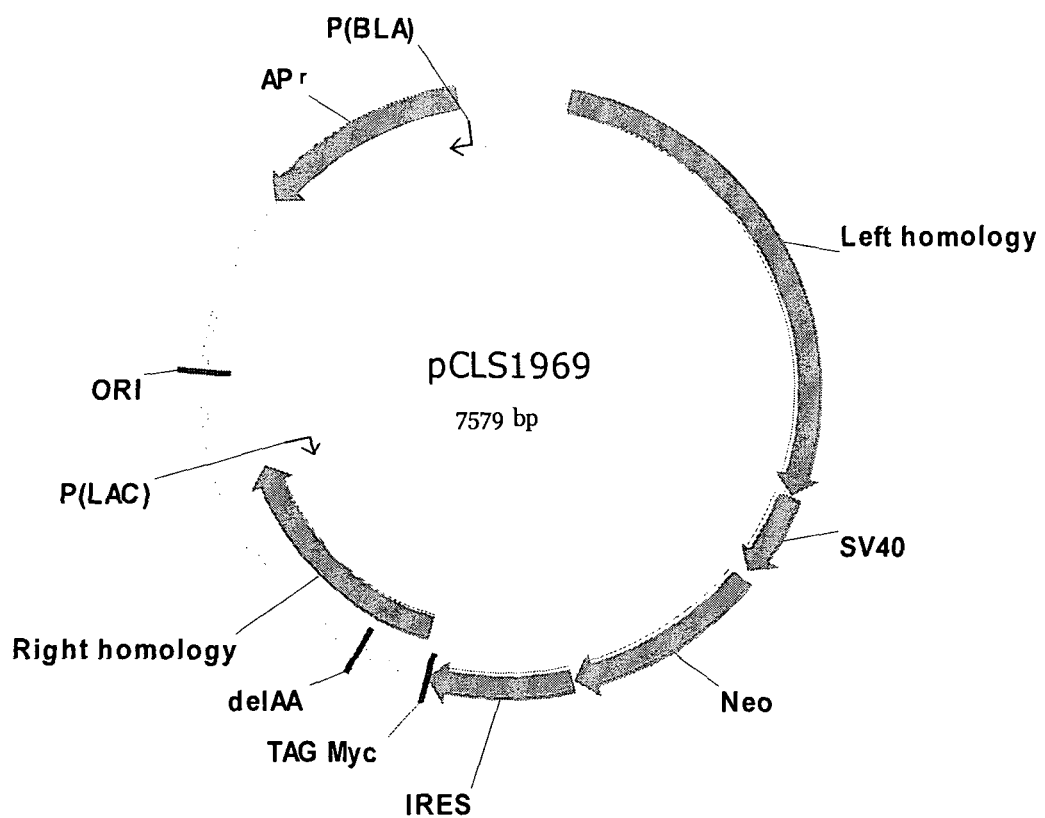

FIG. 25 represents pCLS1969 vector map.

FIG. 26 illustrates the PCR analysis of gene targeting events. Clones wild type for the RAG1 locus and clones having a random insertion of the donor repair plasmid will not result in PCR amplification. Clones having a gene targeting event at the RAG1 locus result in a 2588 bp PCR product.

Figure 27:
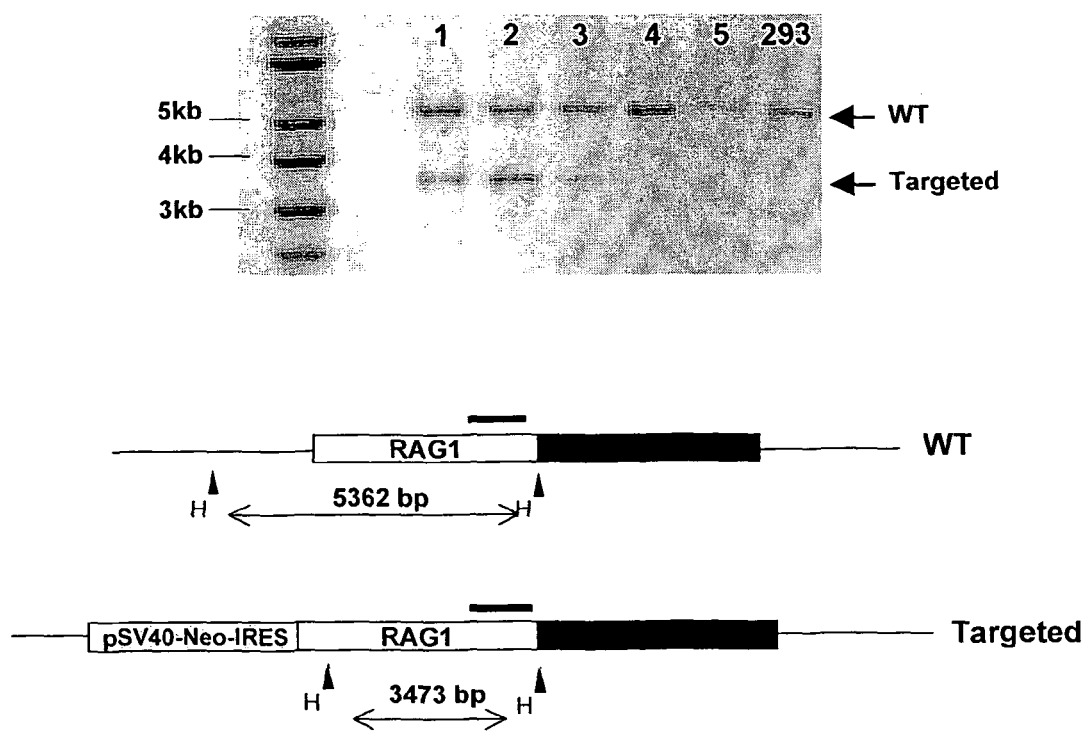

FIG. 27 illustrates the Southern blot analysis of cell clones. Genomic DNA preparations were digested with HindIII and Southern blotting was performed with a fragment of the RAG1 gene lying outside the right homology arm. The locus maps indicate the restriction pattern of the wild-type locus (5.3 kb) and the targeted locus (3.4 kb). The probe is indicated by a solid black box. Five clones (1-5) samples derived from single transfected cells are analyzed, together with DNA from non transfected cells (293). In three samples, one of the alleles has been targeted. H, HindIII site.

Figure 28:
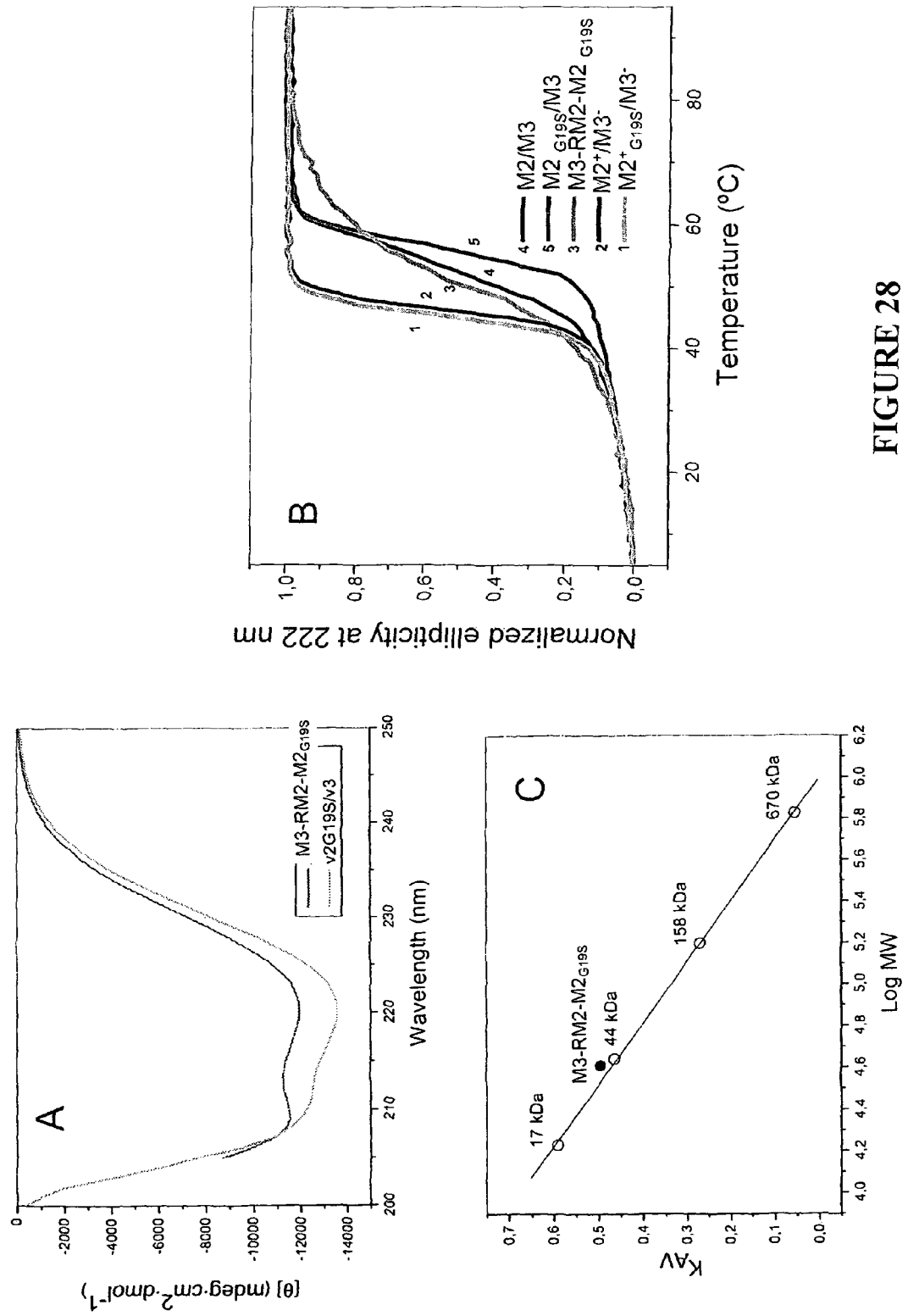

FIG. 28 illustrates the biophysical analysis of the heterodimers and the single chain molecule. A; Circular dichroism spectrum of the single-chain meganuclease and the corresponding heterodimeric protein. B; Thermal denaturation of all the heterodimers and the single-chain variant. C; Calibration graph of partition coefficient (KAV) versus the logarithm of the molecular mass of four protein standards (open circles) for an analytical Superdex-200 10-300GL column. The value of the single-chain meganuclease is indicated with a filled circle (measured MW=34 kDa, theoretical MW=41 kDa).

Figure 29:
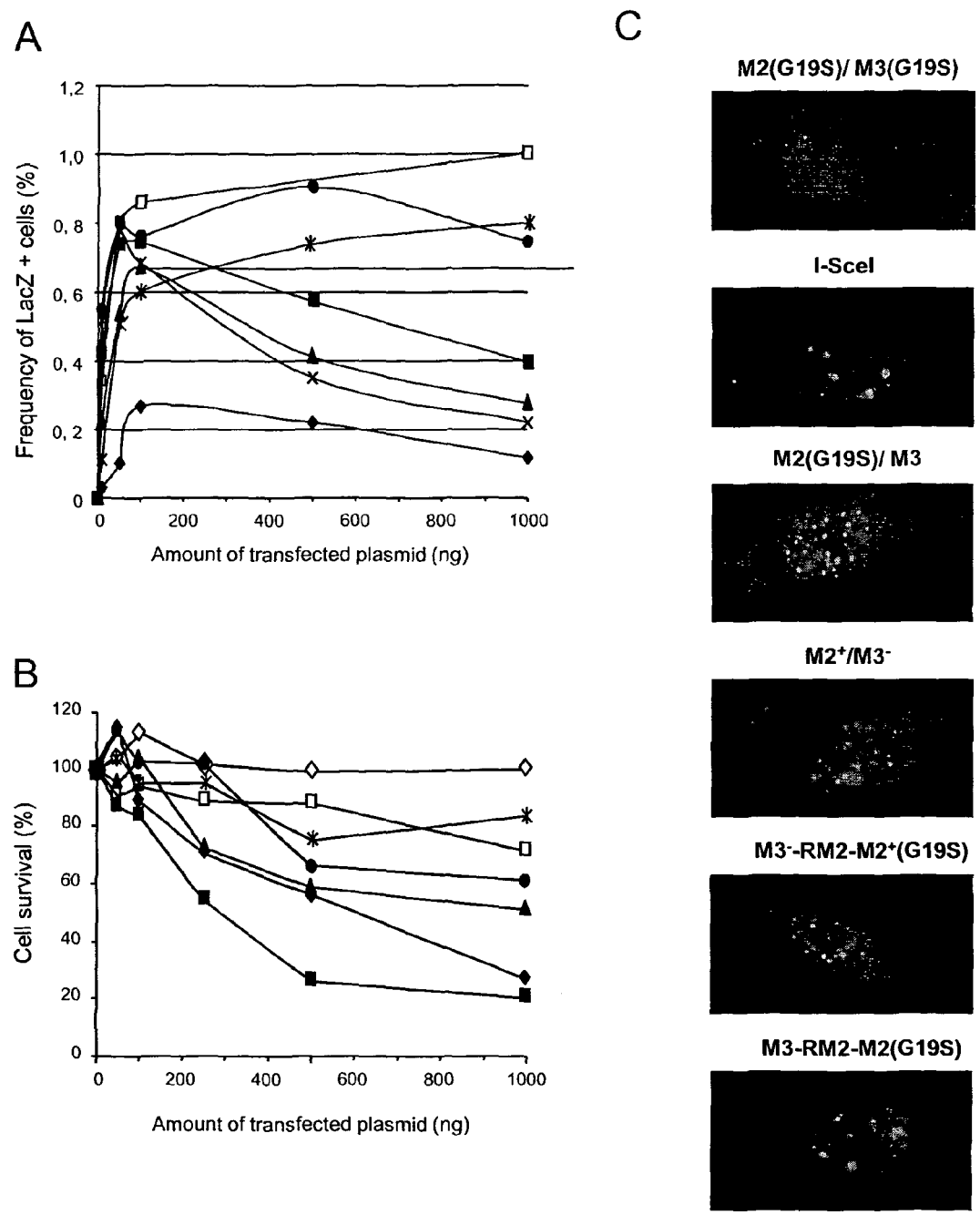

FIG. 29 illustrates toxicity study. A. Dose response study. CHO cell lines were transfected with various amounts of expression vector for various meganucleases and a fixed quantity of the repair plasmid. ♦, M2/M3 heterodimer; ■, M2$_{G19S}$/M3 heterodimer; ▲, M2$^+$/M3$^-$ heterodimer; X, M2$^+_{G19S}$/M3$^-$; ✱, , M3-RM2-M2$_{G19S}$; ●, M2$^+_{G19S}$-RM2-M3$^-$; □, I-SceI. B. Toxicity of the engineered meganucleases, as monitored by a cell survival assay. Various amounts of meganuclease expression vector and a constant amount of plasmid encoding GFP were used to cotransfect CHO-K1 cells. Cell survival is expressed as the percentage of cells expressing GFP six days after transfection, as described in the Materials and Methods. The totally inactive M2$_{G19S}$/M3$_{G19S}$ heterodimer is shown as a control for non toxicity (◇). C. DNA damage was also visualized by the formation of γH2AX foci at DNA double-strand breaks. Representative images of cells treated with 10 times the active dose of meganuclease.

EXAMPLE 1

Figure 1:
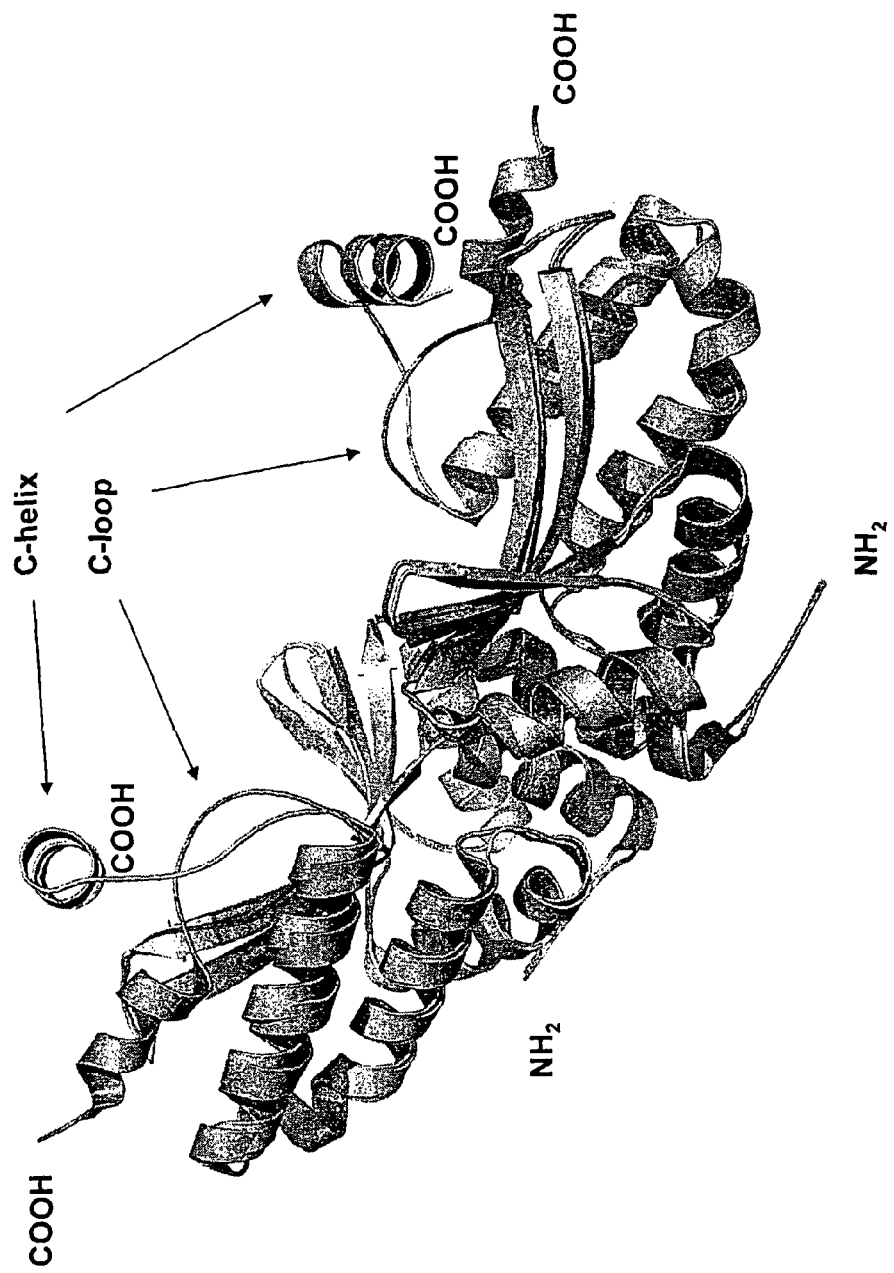
Figure 2:
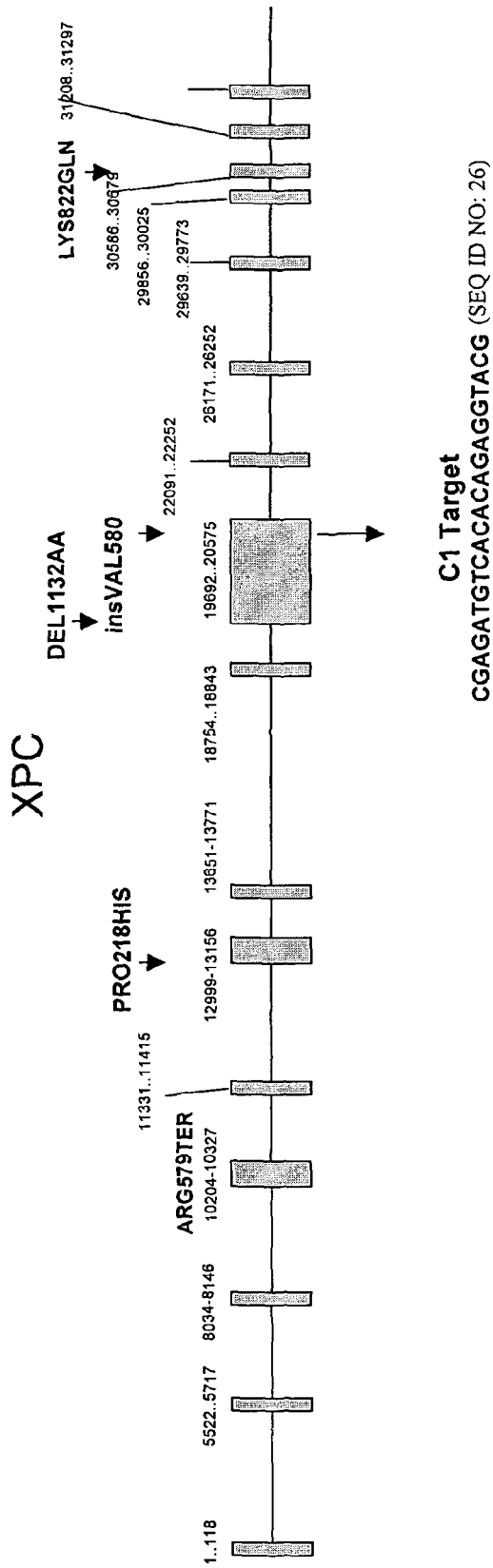
Figure 4:
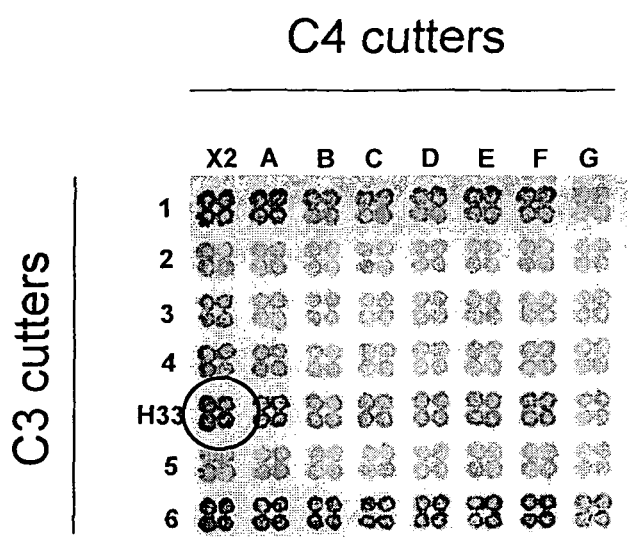

The Making of a Single Chain I-CreI Derived Meganuclease Cleaving the Human XPC Gene Xeroderma Pigmentosum (XP) is a rare autosomal recessive genetic disease characterized by a hypersensitivity to exposure to ultraviolet (UV) rays and a high predisposition for developing skin cancers. The human XPC gene involved in Xeroderma Pigmentosum was scanned for potential target sequences. A potential 22 bp DNA target that was called C1 (cgagatgtcacacagaggtacg; SEQ ID NO: 26), was localized at the end of the XPC ninth exon (FIG. 2). The engineering of I-CreI derived mutants able to cleave the C1 target has been described previously (Arnould et al., J. Mol. Biol., Epub 10 May 2007; International PCT Application WO 2007/093836 and WO 2007/093918). Briefly, the C1 sequence was divided into two palindromic half-targets called C3 and C4 (FIG. 3). As the C3 target is identical to the 10GAG_P target but with a single difference at position ±6, I-CreI derived mutants able to cleave the 10GAG_P target were screened against the C3 target. The mutant H33 bearing the single mutation Y33H (substitution at position 33 of a tyrosine by a histidine residue) in comparison to the I-CreI wild-type sequence, was isolated as a strong C3 cutter. The C4 target is a combination of the 10GTA_P and 5TCT_P targets. I-CreI mutants able to cleave the 10GTA_P and I-CreI mutants able to cleave the 5TCT_P target were combined and screened against the C4 DNA target, as described previously (Smith et al., Nucleic Acids Research, 2006, 34, e149; International PCT Applications WO 2007/049095 and WO 2007/057781). The I-CreI mutant called X2 was isolated as a strong C4 cutter. The X2 mutant bears the following mutations in comparison with the I-CreI wild type sequence: Y33H, Q38A, S40Q, Q44K, R68Q, R70S and D75N. The last step consisted in the yeast co-expression of the H33 and X2 I-CreI mutants, as described previously (International PCT Application WO 2006/097854 and Arnould et al., J. Mol. Biol., 2006, 355, 443-458), which resulted in the strong cleavage of the XPC C1 DNA target (FIG. 4).

The X2/H33 XPC heterodimer obtained by coexpression of the two mutants cleaves the C1 target but also the C3 and C4 targets, because of the presence of the two homodimers. To avoid these side effects, a new way for designing a single chain molecule composed of the two I-CreI derived mutants X2 and H33 was conceived. For that purpose, a full length X2 N-terminal mutant was maintained in the single chain design, and several constructs of the type X2-L-H33, where L is a protein linker, were engineered. In this nomenclature, X2 will be referred as the N-terminal mutant and H33 as the C-terminal mutant. Another important issue was the sequence identity of the two mutants in the single chain molecule. In fact, the two I-CreI mutants X2 and H33 have almost the same nucleic sequence, which raises the problem of the stability of such a construct with the risk of a recombination event between the two almost identical sequences. To avoid or at least reduce this possibility, another I-CreI version, called I-CreI CLS, was used to code for the H33 mutant. The nucleic sequence of I-CreI CLS (SEQ ID NO: 24) has been rewritten from the I-CreI wild type sequence (I-CreI wt; SEQ ID NO: 22) using the codon usage and the genetic code degeneracy. It means that I-CreI CLS shares 73% nucleic sequence identity with I-CreI wt and has three single amino acid mutations (T42A, E110W and Q111R), which do not alter I-CreI activity. The Y33H was then introduced in the I-CreI CLS version (SEQ ID NO: 25). Activity of the H33 CLS mutant was checked against the C3 target and was shown to be as strong as for the H33 mutant in the I-CreI wt version.

Using the H33 CLS mutant, 18 single chain versions of the type X2-L-H33 were built, where Lisa linker, different for each of the 18 versions. The G19S mutation was also introduced in the C-terminal H33 mutant for two single chain molecules. Activity of these different single chain constructs against the C1 XPC target and its two derivatives C3 and C4 was then monitored in yeast and, for some of them, in CHO cells using an extrachromosomal assay.

1) Material and Methods a) Introduction of the Y33H Mutation into the I-CreI CLS Version Two overlapping PCR reactions were performed using two sets of primers: Gal10F (5'-gcaactttagtgctgacacatacagg-3'; SEQ ID NO: 44) and H33Revp60 (5'-ctggtgtttgaacttgtgagat-tgatttggttt-3'; SEQ ID NO: 45) for the first fragment and H33Forp60 (5'-aaaccaaatcaatctcacaagttcaaacaccag-3'; SEQ ID NO: 46) and Gal10R (5'-acaaccttgattggagacttgacc-3'; SEQ ID NO: 47) for the second fragment. Approximately 25 ng of each PCR fragment and 75 ng of vector DNA pCLS0542 (FIG. 5) linearized by digestion with NcoI and EagI were used to transform the yeast *Saccharomyces cerevisiae* strain FYC2-6A (MATα, trp1Δ63, leu2Δ1, his3Δ200) using a high efficiency LiAc transformation protocol (Gietz, R. D. and Woods R. A., Methods Enzymol., 2002, 350, 87-96). An intact coding sequence containing the Y33H mutation is generated by in vivo homologous recombination in yeast.

b) Sequencing of Mutants

To recover the mutant expressing plasmids, yeast DNA was extracted using standard protocols and used to transform *E. coli*. Sequencing of mutant ORF was then performed on the plasmids by MILLEGEN SA.

c) Cloning of the Eighteen XPC Single Chain Molecules

Eighteen independent PCR reactions were performed on the H33 mutant in the I-CreI CLS version. Each PCR reaction uses the same reverse primer CreCterR60 (5'-tagacgagctc-ctaaggagaggacttttcttctcag-3'; SEQ ID NO: 48) and a specific forward primer. The eighteen forward primers that were used are:

L1EagI:
(SEQ ID NO: 49)
5'-tatcggccggtggcggaggatctggcggcggtggatccggtgg
tggaggctccggaggaggtggctctaacaaagagttcctgctgtat
cttgctgga-3'

YPP:
(SEQ ID NO: 50)
5'-tatcggccggtaaatcttccgattccaagggtattgatctgac
taatgttactctgcctgataccctacttattccaaagctgcctct
gatgctattcctccagctaacaaagagttcctgctgtatcttgctg
gattt-3'

AOL:
(SEQ ID NO: 51)
5'-tatcggccggtctggagtatcaggctccttactcttccctcc
aggtcctccttgttgctccggttcctctggctcctctgctggttgt
tctaacaaagagttcctgctgtatcttgctggattt-3'

CXT:
(SEQ ID NO: 52)
5'-tatcggccggtctgtcctatcattattctaatggtggctcccc
tacttctgatggtccagctctgggtggcatttctgatggtggcgct
actaacaaagagttcctgctgtatcttgctggattt-3'

BQY:
(SEQ ID NO: 53)
5'-tatcggccggtgattcctctgtttctaattccgagcacattgc
tcctctgtctctgccttcctctcctccatctgttggttctaacaaa
gagttcctgctgtatcttgctggattt-3'

VSG:
(SEQ ID NO: 54)
5'-tatcggccggtgcttctcagggttgtaaacctctggctctgcc
tgagctgcttactgaggattcttataatactgataacaaagagttc
ctgctgtatcttgctggattt-3'

BYM:
(SEQ ID NO: 55)
5'-tatcggccggtaatcctattcctggtctggatgagctgggtgt
tggcaactctgatgctgccgctcctggcactaacaaagagttcctg
ctgtatcttgctggattt-3'

MCJ:
(SEQ ID NO: 56)
5'-tatcggccggtgctcctactgagtgttctccttccgctctgac
ccagcctccatccgcttctggttccctgaacaaagagttcctgctg
tatcttgctggattt-3'

GSmid:
(SEQ ID NO: 57)
5'-tatcggccggtggaggcggttctggaggcggtggctctggtgg
aggcggttccggtggaggcggatctggtggaggcggttctaacaaa
gagttcctgctgtatcttgctggattt-3'

GSshort:
(SEQ ID NO: 58)
5'-tatcggccggtggaggcggttctggaggcggtggctctggtgg
aggcggttccaacaaagagttcctgctgtatcttgctggattt-3'

GSxshort:
(SEQ ID NO: 59)
5'-tatcggccggtggaggcggttctggaggcggtggctctaacaa
agagttcctgctgtatcttgctggattt-3

PPR:
(SEQ ID NO: 60)
5'-tatcggccggtcaggttacttctgctgccggtcctgctactgt
tccatctggtaacaaagagttcctgctgtatcttgctggattt-3'

SBA1:
(SEQ ID NO: 61)
5'-tatcggccggtggatctcctctgaagccttctgccccaaagat
tcctataggtggctccaacaaagagttcctgctgtatcttgctgga
ttt-3'

SBA2:
(SEQ ID NO: 62)
5'-tatcggccggtggatctcctctgaagccttctgccccaaagat
tcctataggtggctccccactgaaaccttccgcacctaaaatccca
attggtggctctaacaaagagttcctgctgtatcttgctggatt
t-3'

LP1:
(SEQ ID NO: 63)
5'-tatcggccggtggatctcctctgtctaaaccaattccaggcgg
ttccaacaaagagttcctgctgtatcttgctggattt-3'

LP2:
(SEQ ID NO: 64)
5'-tatcggccggtggatctcctctgtctaaaccaattccaggcgg
ttccccactgtcaaagccaatccctggcggttctaacaaagagttc
ctgctgtatcttgctggattt-3'

-continued

RM1:
(SEQ ID NO: 65)
5'-tatcggccggtggatctgataagtataatcaggctctgtctga
gcgtcgcgcctacgttgtcgccaataacctggtttccggtggaggc
ggttccaacaaagagttcctgctgtatcttgctggattt-3'

RM2:
(SEQ ID NO: 66)
5'-tatcggccggtggatctgataagtataatcaggctctgtctaa
atacaaccaagcactgtccaagtacaatcaggccctgtctggtgga
ggcggttccaacaaagagttcctgctgtatcttgctggattt-3'.

All PCR fragments were purified and digested by EagI and SacI and each PCR fragment was ligated into the yeast expression vector for the X2 mutant also digested with EagI and SacI. After sequencing of the clones, all single chain molecules in the yeast expression vector were obtained.

d) Introduction of the G19S Mutation into the C-Terminal H33 Mutant of the Two Single Chain Molecules X2-L1-H33 and X2-RM2-H33

Figure 5:
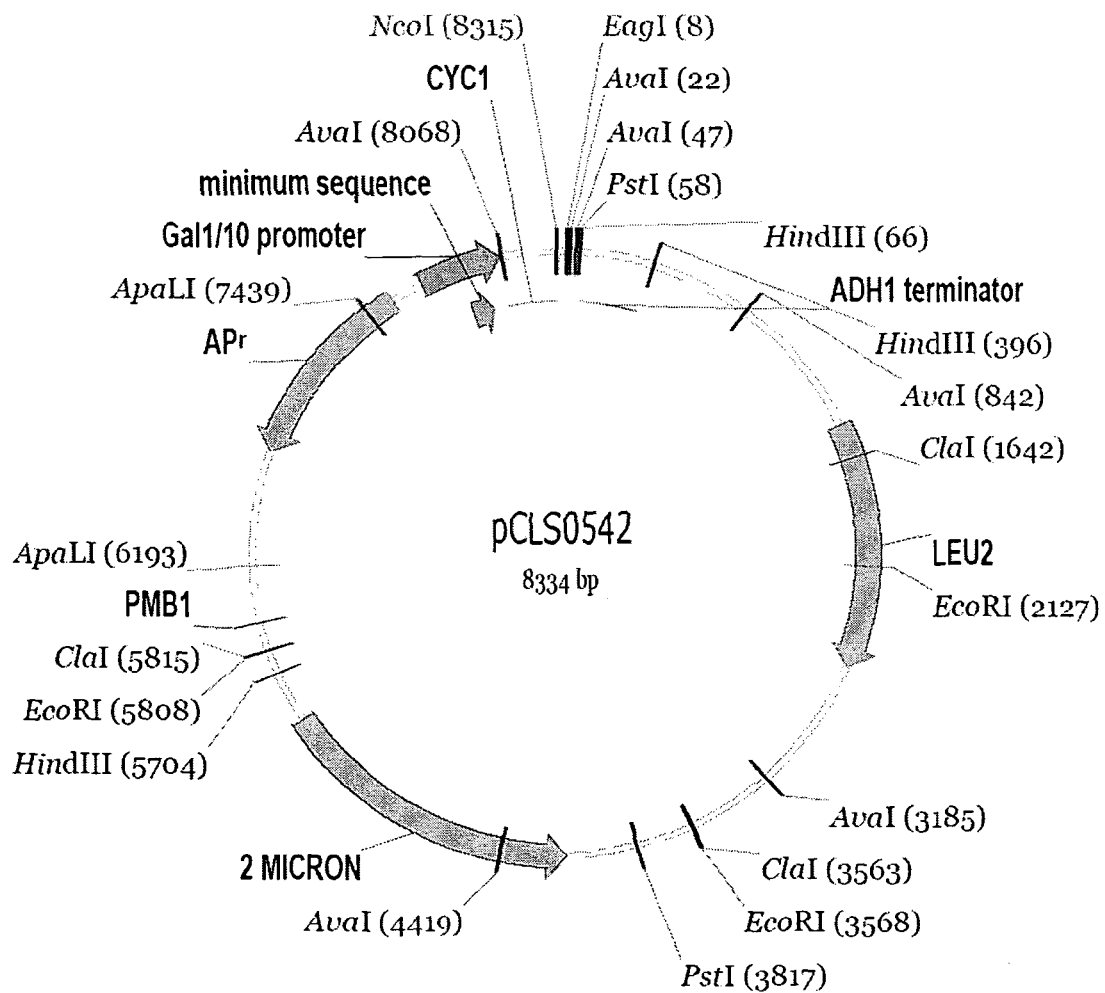
FIG. 5 represents the pCLS0542 meganuclease expression vector map. pCLS0542 is a 2 micron-based replicative vector marked with a LEU2 auxotrophic gene, and an inducible Gal10 promoter for driving the expression of the meganuclease.

Two overlapping PCR reactions were performed using two sets of primers: Gal10F (5'-gcaactttagtgctgacacatacagg-3': SEQ ID NO: 44) and G19SRev (5' gcaatgatggagccatcagaatc-cacaaatccagc-3': SEQ ID NO: 67) for the first fragment and G19SFor60 (5'-gctggatttgtggattctgatggctccatcattgc-3': SEQ ID NO: 68) and Gal10R (5'-acaaccttgattggagacttgacc-3': SEQ ID NO: 47) for the second fragment. Approximately 25 ng of each PCR fragment and 75 ng of vector DNA (pCLS0542; FIG. 5) linearized by digestion with NcoI and EagI were used to transform the yeast Saccharomyces cerevisiae strain FYC2-6A (MATα, trp1Δ63, leu2Δ1, his3Δ200) using a high efficiency LiAc transformation protocol (Gietz R. D. and Woods R. A., Methods Enzymol., 2002, 350, 87-96). An intact coding sequence containing the G19S mutation is generated by in vivo homologous recombination in yeast.

e) Introduction of the K7E, E8K and G19S Mutations in the XPC X2-L1-H33 Single Chain Molecule First, the G19S mutation was introduced in the X2-L1-H33 molecule. Two overlapping PCR reactions were performed on the single chain molecule cloned in the pCLS0542 yeast expression vector. The first PCR reaction uses the primers: Gal10F (5'-gcaactttagtgctgacacatacagg-3'; SEQ ID NO: 44) and G19SRev60 (5'-gcaatgatggagccatcagaatccacaaatccagc-3'; SEQ ID NO: 67) and the second PCR reaction, the primers G19SFor60 (5'-gctggatttgtggattctgatggctccatcattgc-3; SEQ ID NO: 68) and Gal10R (5'-acaaccttgattggagacttgacc-3'; SEQ ID NO: 47). Approximately 25 ng of each PCR fragment and 75 ng of vector DNA (pCLS0542; FIG. 5) linearized by digestion with NcoI and EagI were used to transform the yeast Saccharomyces cerevisiae strain FYC2-6A (MATα, trp1Δ63, leu2Δ1, his3Δ200) using a high efficiency LiAc transformation protocol (Gietz R. D. and Woods R. A., Methods Enzymol., 2002, 350, 87-96). An intact coding sequence containing the G19S mutation was generated by in vivo homologous recombination in yeast.

In a second step, the K7E and E8K mutations were introduced in the X2-L2-H33(G19S) molecule by performing three overlapping mutations. For the SCX1 molecule, the 3 PCR reactions use three primers set, which are respectively: Gal10F and K7ERev (5'-gtacagcaggaactcttcgttatatttggtattgg-3'), K7EFor (5'-aataccaaatataacgaagagttcctgctgtacc-3'; SEQ ID NO: 69) and E8KRevSC (5'-aagatacagcaggaactttttgtta-gagccacc-3'; SEQ ID NO: 70), E8KForSc (5'-ggtggctctaa-caaaaagttcctgctgtatctt-3'; SEQ ID NO: 71) and Gal10R. For the SCX2 molecule, the 3 PCR reactions use three primers set, which are respectively: Gal10F and E8KRev (5'-caggta-cagcaggaactttttgttatatttgg-3'; SEQ ID NO: 72), ESKFor (5'-accaaatataacaaaaagttcctgctgtacctgg-3'; SEQ ID NO: 73) and K7ERevSC (5'-aagatacagcaggaactcttcgttagagccacc-3'; SEQ ID NO: 74), K7EFor Sc (5'-ggtggctctaacgaagagttcctgctg-tatctt-3'; SEQ ID NO: 75) and Gal10R. For both constructs, approximately 25 ng of each PCR fragment and 75 ng of vector DNA (pCLS0542; FIG. 5) linearized by digestion with NcoI and EagI were used to transform the yeast Saccharomyces cerevisiae strain FYC2-6A (MATα, trp1Δ63, leu2Δ1, his3Δ200) using a high efficiency LiAc transformation protocol (Gietz R D and Woods R A Transformation of yeast by lithium acetate/single-stranded carrier DNA/polyethylene glycol method. Methods Enzymol. 2002; 350:87-96). An intact coding sequence for the SCX1 or SCX2 constructs was generated by in vivo homologous recombination in yeast.

f) Mating of Meganuclease Expressing Clones and Screening in Yeast

Screening was performed as described previously (International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458). Mating was performed using a colony gridder (QpixII, Genetix). Mutants were gridded on nylon filters covering YPD plates, using a low gridding density (about 4 spots/cm2). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

g) Cloning of the XPC Single Chain Constructs into a Mammalian Expression Vector Each mutant ORF was amplified by PCR using the primers CCM2For (5'-aagcagagctctctggctaacta-gagaacccactgcttactggcttatcgaccatggccaatacc aaatataacaaa-gagttcc-3': SEQ ID NO: 76) and CCMRev60 (5'-ctgctctagac-taaggagaggacttttttacttctcag-3': SEQ ID NO: 77). The PCR fragment was digested by the restriction enzymes SacI and XbaI, and was then ligated into the vector pCLS1088 (FIG. 6) digested also by SacI and XbaI. Resulting clones were verified by sequencing (MILLEGEN).

h) Cloning of the C1, C3 and C4 Targets in a Vector for Extrachromosomal Assay in CHO Cells The target of interest was cloned as follow: oligonucleotide corresponding to the target sequence flanked by gateway cloning sequence was ordered from PROLIGO. Double-stranded target DNA, generated by PCR amplification of the single stranded oligonucleotide, was cloned using the Gateway protocol (INVITROGEn) into CHO reporter vector (pCLS1058, FIG. 7).

i) Extrachromosomal Assay in CHO Cells

CHO cells were transfected with Polyfect transfection reagent according to the supplier's (QIAGEN) protocol. 72 hours after transfection, culture medium was removed and 150 μl of lysis/revelation buffer added for β-galactosidase liquid assay (1 liter of buffer contained 100 ml of lysis buffer (Tris-HCl 10 mM pH7.5, NaCl 150 mM, Triton X100 0.1%, BSA 0.1 mg/ml, protease inhibitors), 10 ml of Mg 100× buffer (MgCl$_2$ 100 mM, β-mercaptoethanol 35%), 110 ml ONPG 8 mg/ml and 780 ml of sodium phosphate 0.1M pH7.5). After incubation at 37° C., OD was measured at 420 nm. The entire process was performed on an automated Velocity11 BioCel platform.

2) Results a) Cleavage Activity of the 18 XPC Single-Chain Meganucleases Against the Three XPC Targets Table I shows the different linkers that have been used to build the different single chain molecules. For each single chain molecule, the linker begins after the last residue (P163) of the N-terminal X2 mutant and after the linker, the N-terminal H33 mutant begins at residue N6.

TABLE I

Linkers

| Number | Linker Name | Size (aa) | SEQ ID NO: | Primary Sequence |
|---|---|---|---|---|
| 1 | L1 | 22 | 3 | -AA(GGGGS)$_4$- |
| 2 | YPP | 35 | 4 | -AAGKSSDSKGIDLTNVTLPDTPTYSKAASDAIPPA- |
| 3 | AOL | 31 | 5 | -AAGLEYPQAPYSSPPGPPCCSGSSGSSAGCS- |
| 4 | CXT | 30 | 6 | -AAGLSYHYSNGGSPTSDGPALGGISDGGAT- |
| 5 | BQY | 27 | 7 | -AAGDSSVSNSEHIAPLSLPSSPPSVGS- |
| 6 | VSG | 25 | 8 | -AAGASQGCKPLALPELLTEDSYNTD- |
| 7 | BYM | 24 | 9 | -AAGNPIPGLDELGVGNSDAAAPGT- |
| 8 | MCJ | 23 | 10 | -AAGAPTECSPSALTQPPSASGSL- |
| 9 | GSmid | 27 | 11 | -AA(GGGGS)$_5$- |
| 10 | Gsshort | 17 | 12 | -AA(GGGGS)$_3$- |
| 11 | GSxshort | 12 | 13 | -AA(GGGGS)$_2$- |
| 12 | PPR | 17 | 14 | -AAGQVTSAAGPATVPSG- |
| 13 | SBA1 | 19 | 15 | -AAGGSPLKPSAPKIPIGGS- |
| 14 | SBA2 | 33 | 16 | -AAGGSPLKPSAPKIPIGGSPLKPSAPKIPIGGS- |
| 15 | LP1 | 15 | 17 | -AAGGSPLSKPIPGGS- |
| 16 | LP2 | 25 | 18 | -AAGGSPLSKPIPGGSPLSKPIPGGS- |
| 17 | RM1 | 31 | 19 | -AAGGSDKYNQALSERRAYWANNLVSGGGGS- |
| 18 | RM2 | 32 | 2 | -AAGGSDKYNQALSKYNQALSKYNQALSGGGGS- |

The cleavage activity of the 18XPC single chain molecules was monitored against the three XPC targets C1, C3 and C4, using the yeast screening assay previously described (International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458). As shown in FIG. 8, all the single chain constructs cleave the C1 target, but also strongly the C3 target while activity toward the C4 target is also detectable. The two single chain molecules X2-L1-H33 and X2-RM2-H33 were cloned into a mammalian expression vector and their activity toward the three XPC targets was checked in CHO cells using an extrachromosomal assay (FIG. 9). This assay confirmed the yeast cleavage profile (FIG. 9). Furthermore, X2-RM2-H33 is more active toward the C1 target than X2-L1-H33 in CHO cells. C4 cleavage is barely detectable in CHO cells. No cleavage of C3 was observed with X2, and similarly, H33 does not cleave C4 (data not shown). Thus, the strong cleavage of the C3 target with single chain molecules suggests that the linker does not abolish the formation of intermolecular species, resulting from interaction between the dimerization interfaces of the H33 units from two distinct molecules. The formation of pseudo H33 homodimers would then be responsible for C3 cleavage.

b) Effect of the G19S Mutation Alone on the Specificity of Cleavage of the XPC Single-Chain Meganuclease In order to test this hypothesis, the G19S mutation (was introduced in the H33 C-terminal mutant of the two single chain molecules. The G19S mutation (mutation of residue 19 from I-CreI, according to pdb 1G9Y numeration) has been shown before to abolish the formation of functional homodimers while enhancing the activity of the heterodimers displaying a G19S monomer (International PCT Application WO 2008/010093). The two single chain molecules that were obtained (X2-L1-H33$_{G19S}$ and X2-RM2-H33$_{G19S}$), were then profiled against the three XPC targets using the extrachromosomal assay in CHO cells. FIG. 10 shows that the G19S mutation does not only increases the activity toward the C1 target but also greatly reduces the activity toward the C3 target. The profile cleavage of the X2/H33 heterodimer against the three XPC targets is also shown on FIG. 10, for comparison.

These results confirm the hypothesis of intermolecular species formation, resulting from the interaction of two H33 units. Similarly, interaction between two X2 units probably account for weak cleavage of the C4 target (FIGS. 8 and 9). Thus, although the introduction of a linker between the X2 and H33 monomers might favour intramolecular interactions (resulting in reduced cleavage of C4 for example), it does not abolish intermolecular interactions.

Nevertheless, the engineered XPC single chain molecule X2-RM2-H33$_{G19S}$ cleaves more strongly the C1 XPC target than the X2/H33 heterodimer and has much reduced cleavage activities toward the two palindromic C3 and C4 targets than the same heterodimer. The single chain molecule X2-RM2-H33$_{G19S}$ displays a much better specificity than the X2/H33 heterodimer and has an activity level comparable to that of I-SceI, the gold standard in the field of homologous recombination induced by DNA double strand break.

c) Effect of the Combination of the G19S Mutation with Another Mutation that Impairs the Formation of a Functional Homodimer on the Specificity of Cleavage of the XPC Single-Chain Meganuclease FIG. 11 shows the activity of the three single chain molecules X2-L1-H33, SCX1 and SCX2 against the three XPC targets in a yeast screening assay. The initial single chain molecule has a strong cleavage activity against the C1 and C3 target but introduction of the K7E/E8K and G19S mutations to generate the SCX1 and SCX2 molecules promotes an increased cleavage activity toward the C1 target and a complete abolition of the cleavage activity toward the C3 target. Thus, the mutations K7E/E8K and G19S can be successfully introduced in a single chain molecule to improve its specificity without affecting its cleavage activity toward the DNA target of interest.

EXAMPLE 2

The Making of a Single Chain I-CreI Derived Meganuclease Cleaving the *Cricetulus griseus* HPRT Gene The Hypoxanthine-Guanine Phosphorybosyl Transferase (HPRT) gene from *Cricetulus griseus* was scanned for a potential target site. A 22 bp sequence called HprCH3 (cgagatgtcatgaaagagatgg: SEQ ID NO: 34) was identified in the gene ORF (FIG. 12). Two derived palindromic targets HprCH3.3 and HprCH3.4 were derived from the HprCH3 target (FIG. 13). As the HprCH3.3 target is identical to the C3 target described above in Example 1, the H33 I-CreI mutant is able to cleave strongly HprCH3.3 (C3). The HprCH3.4 target is a combination of the 10CAT_P and 5CTT_P targets. I-CreI mutants able to cleave the 10CAT_P target were obtained as previously described in Smith et al., Nucleic Acids Research, 2006, 34, e149; International PCT Applications WO 2007/049156 and WO 2007/060495 and I-CreI mutants able to cleave the 5CTT_P target were obtained as previously described in Arnould et al., J. Mol. Biol., 2006; 355, 443-458; International PCT Applications WO 2006/097784 and WO 2006/097853. The mutants were combined as previously described in Smith et al., Nucleic Acids Research, 2006, 34, e 149; International PCT Applications WO 2007/049095 and WO 2007/057781 and then screened against the HprCH3.4 DNA target. The I-CreI mutant called MA17 was isolated as a HprCH3.4 cutter. However, it was found to cleave also the HprCH3.3 target, due to a relaxed specificity (see FIG. 14). The MA17 mutant bears the following mutations in comparison with the I-CreI wild type sequence: S32T, Y33H, Q44R, R68Y, R70S, S72T, D75N and I77N. The last step consisted in the yeast co-expression of the H33 and MA17 I-CreI mutants, as described previously (International PCT Application WO 2006/097854 and Arnould et al., J. Mol. Biol., 2006, 355, 443-458), which resulted in the cleavage of the HprCH3 DNA target.

Two HPRT single chain constructs were engineered following the same scheme as in example 1. The two L1 and RM2 linkers (see Table I of Example 1) were used, resulting in the production of the MA17-L1-H33 and MA17-RM2-H33 single chain molecules. In a second step, the G19S mutation was introduced in the C-terminal H33 mutant, resulting in a two other single chain meganuclease, MA17-L1-H33$_{G19S}$ and MA17-RM2-H33$_{G19S}$. The activity of these different constructs was then monitored in yeast and in CHO cells against the HprCH3 target and its two derivatives HprCH3.3 and HprCH3.4 targets.

1) Material and Methods
See example 1
2) Results

The activity of three single chain molecules (MA17-L1-H33, MA17-L1-H33$_{G19S}$ and MA17-RM2-H33) against the three HPRT targets HprCH3, HprCH3.3 and HprCH3.4 was monitored using the previously described yeast assay (International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458). As shown in FIG. 14, MA17-L1-H33 does not cleave the HprCH3 target, which is cleaved by the two other single chain molecules. Thus, the RM2 linker seems to be better adapted to the way we have engineered the single chain constructs, as already observed in example 1. These results also confirm that the presence of the G19S mutation enhances the heterodimeric activity. All three single chain molecules cleave very strongly the HprCH3.3 (identical to the C3 target from example 1), but do not cleave the HprCH3.4, in contrast with the MA17/H33 heterodimer. In this case, cleavage of HprCH3.3 (C3) is not necessarily due to the formation of intermolecular species: since the MA17 and H33 mutants both cleave the HprCH3.3 target as homodimers, a MA17/H33 heterodimer or a MA17-RM2-H33 single chain monomer could in principle cleave HprCH3.3. This hypothesis is confirmed by the persistent cleavage of HprCH3.3 by MA17-L1-H33$_{G19S}$ and MA17-RM2-H33$_{G19S}$. Next, four single chain molecules (MA17-L1-H33, MA17-L1-H33$_{G19S}$, MA17-RM2-H33 and MA17-RM2-H33$_{G19S}$) were cloned into a mammalian expression vector tested in CHO cells using for cleavage of the three HPRT targets (FIG. 15). The MA17-RM2-H33$_{G19S}$ single chain molecule displayed the strongest activity. Again strong cleavage of HprCH3.3 (C3) was observed, while cleavage of HprCH3.4 was low or absent.

EXAMPLE 3

The Making of a Single Chain I-CreI Derived Meganuclease Cleaving the Human RAG1 Gene RAG1 is a gene involved in the V(D)J recombination process, which is an essential step in the maturation of immunoglobulins and T lymphocytes receptors (TCRs). Mutations in the RAG1 gene result in defect in lymphocytes T maturation, always associated with a functional defect in lymphocytes B, which leads to a Severe Immune Combined Deficiency (SCID). A 22 bp DNA sequence located at the junction between the intron and the second exon of the human RAG1, called RAG1.10 (SEQ ID NO: 41; FIG. 16) had been identified as a potential cleavable sequence by our meganucleases (Smith et al., Nucleic Acids Research, 2006, 34, e149 International PCT Application WO 2008/010093). The RAG1.10 sequence was derived into two palindromic RAG1.10.2 and RAG1.10.3 sequences (FIG. 17). RAG1.10.2 target is a combination of the 10GTT_P and 5CAG_P targets and RAG1.10.3 target is a combination of the 10TGG_P and 5GAG_P targets. Strong cutters for both RAG1.10.2 and RAG1.10.3 targets were obtained by combining I-CreI mutants able to cleave the 10GTT_P and 5CAG_P targets from one side, and the 10TGG_P and 5GAG_P targets from the other side, as described previously in Smith et al., Nucleic Acids Research, 2006, 34, e149; International PCT Applications WO 2007/049095, WO 2007/057781, WO 2007/049156, WO 2007/060495, WO 2006/097784 and WO 2006/097853; Arnould et al., J. Mol. Biol., 2006; 355, 443-458). Coexpression of the cutters as described previously (International PCT Application WO 2006/097854 and Arnould et al., J. Mol. Biol., 2006, 355, 443-458) leads then to a strong cleavage of the RAG1.10 target. The M2/M3 RAG1.10 heterodimer gives the strongest cleavage in yeast (International PCT Application WO 2008/010093). M2 is a RAG1.10.2 cutter and bears the following mutations in comparison with the I-CreI wild type sequence: N30R, Y33N, Q44A, R68Y, R70S and I77R. M3 is a RAG1.10.3 cutter and bears the following mutations in comparison with the I-CreI wild type sequence: K28N, Y33S, Q38R, S40R, Q44Y, R70S, D75Q and I77V.

Following the same experimental scheme as in Examples 1 and 2, three single chain constructs were engineered using the two linkers L1 and RM2 (see Table I of Example 1), resulting in the production of the three single chain molecules: M2-L1-M3, M2-RM2-M3 and M3-RM2-M2. In a second step, the G19S mutation was introduced in the N-terminal M2 mutant from the M2-L1-M3 and M2-RM2-M3 single chain molecules, resulting in two additional constructs. In addition, mutations K7E, K96E were introduced into the M3 mutant and mutations E8K, E61R into the M2 mutant of M3-RM2-M2 to create the single chain molecule: M3(K7E K96E)-RM2-M2(E8K E61R) that is called further SC_OH The six single chain constructs were then tested in yeast for cleavage of the RAG1.10 target and of its two RAG1.10.2 and RAG1.10.3 derivatives.

1) Material and Methods

See example 1, except for mutations of I-CreI CLS (T42A, E110W and Q111R) which were reverted.

Cloning of the SC_OH Single Chain Molecule

A PCR reaction was performed on the M2 mutant carrying the K7E and K96E mutations cloned in the pCLS0542 yeast expression vector. The PCR reaction uses the reverse primer CreCterSacI (5'-tagacgagctcctacggggaggatttcttcttctcgct-3'; SEQ ID NO: 78) and the forward primer. RM2 (5'-tatcggccggtggatctgataagtataatcag-gactgtctaaatacaaccaagcactgtccaagtacaatc aggccctgtctggtg-gaggcggttccaacaaagagttcctgctgtatcttgctggattt 3'; SEQ ID NO: 66).

The PCR fragment was purified and digested by EagI and SacI and ligated into the yeast expression vector for the M3 mutant carrying the mutations E8K and E61R also digested with EagI and SacI. After sequencing of the clones, a SC_OH single chain molecule was obtained 2) Results The activity of the four RAG1 single chain molecules (M2-L1-M3, M2$_{G19S}$-L1-M3, M2-RM2-M3 and M2$_{G19S}$-RM2-M3) was monitored against the three RAG1 targets RAG1.10, RAG1.10.2 and RAG1.10.3 (FIG. 18) using the previously described yeast assay (International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458). As observed previously in examples 1 and 2, the RM2 linker seems to be better adapted to the way the single chain constructs were engineered: cleavage of the RAG1.10 target was observed with the M2-RM2-M3 molecule, but not with M2-L1-M3. In addition, M2-RM2-M3 was found to cleave also RAG1.10.2. Since M3 does not cleave RAG1.10.2 (FIG. 18), these results suggest that intermolecular interactions can still result in contact between two M2 units, that would form a homodimeric or pseudo-homodimeric species responsible for cleavage of the palindromic RAG1.10.2 target.

Introduction of the G19S mutation in the M2 mutant improved the activity of both molecule, since M2$_{G19S}$-L1-M3 cleaves the RAG1.10 target, and M2$_{G19S}$-RM2-M3 is more active than M2-L1-M3. In addition, the G19S mutation, which has been shown previously to impair formation of functional homodimers (see example 1 of the present Application and International PCT Application WO 2008/010093), abolishes RAG1.10.2 cleavage. This result is consistent with the hypothesis that interaction between M2 units from distinct M2-RM2-M3 single chain molecules is still possible. However, the single chain structure might favour intramolecular interactions in some extent, for in contrast with M3, the M2-RM2-M3 molecule does not cleave RAG1.10.3 In conclusion, the M2$_{G19S}$-RM2-M3 RAG1 single chain molecule cleaves the RAG1.10 target at a saturating level in yeast, comparable to that observed with the M2/M3 heterodimer, and does not show any cleavage of the two derived palindromic targets RAG1.10.2 and RAG1.10.3.

The yeast screen of the two single chain molecules M3-RM2-M2 and SC_OH against the three RAG1.10 targets depicted in FIG. 19 shows that introduction of the K7E/E8K and E61R/K96E allows for the abolition of the homodimeric activity against the RAG1.10.2 target without reducing the single chain cleavage activity for the RAG1.10 target. It is therefore possible to introduce these mutations in a single chain molecule to improve its specificity without affecting its activity toward the DNA target of interest.

EXAMPLE 4

Making of RAG1 Single Chain Molecules with Different Positions for the Two Mutants Composing the Single Chain Molecules and Different Localization of the G19S Mutation To evaluate the impact of the localization of each mutant and of the G19S mutation on the single chain molecule activity, six constructs (M2-RM2-M3, M2$_{G19S}$-RM2-M3, M2-RM2-M3$_{G19S}$, M3-RM2-M2, M3$_{G19S}$-RM2-M2, M3-RM2-M2$_{G19S}$) were tested for cleavage against the three RAG1.10, RAG1.10.2 and RAG1.10.3 targets using our yeast screening assay.

1) Material and Methods

See example 1

2) Results

As shown in FIG. 20 all six single chain molecules (M2-RM2-M3, M2$_{G19S}$-RM2-M3, M2-RM2-M3$_{G19S}$, M3-RM2-M2, M3$_{G19S}$-RM2-M2, M3-RM2-M2$_{G19S}$) are highly active on the RAG1.10 target, activity equivalent to the initial M2/M3 heterodimer activity on the same target. The relative position (N-ter or C-ter) of the monomer M2 or M3 in the Single Chain does not influence the overall activity of the molecule. For example, the M2-RM2-M3 protein shows the same cleavage pattern as the M3-RM2-M2 molecule, cleaving with the same intensity the RAG1.10 and RAG1.10.2 targets but not the RAG1.10.3 target (RR target).

For some constructs, the RAG1.10.2 palindromic target is cleavable suggesting that inter-molecular interactions can occur and create active nuclease. However, this residual activity is abolished by the introduction of the G19S mutation. The comparison of the activity profile of molecules 2 and 3 in FIG. 20 (M2G19S-RM2-M3 and M2-RM2-M3G19S) shows that the G19S mutation localization does not influence activity on the RAG1.10 target but abolishes a residual homodimer activity, when the mutant (here mutant M2) responsible for this activity carries the G19S mutation.

EXAMPLE 5

Importance of the G19S Mutation in a Single Chain Molecule as Shown by Extrachromosomal Assay in CHO Cells In terms of RAG1.10 cleavage activity, the six single chain molecule presented above as well as the SC_OH single chain molecule depicted in example 3 seem to be equivalent in the yeast screening assay. But they all cleave this target at saturating levels. Therefore, activity of two single chain molecules with or without the G19S mutation against the three RAG1.10, RAG1.10.2 and RAG1.10.3 targets was evaluated in CHO cells using an extrachromosomal SSA assay described in example 1. The four single chain molecules chosen for this assay were: M3-RM2-M2, M3-RM2-M2$_{G19S}$, M3$^-$-RM2-M2$^+$ and M3$^-$-RM2-M2$^+_{G19S}$. M3$^-$ indicates the M3 mutant carrying the K7E and K96E mutations and M2$^+$ represents the M2 mutant carrying the E8K and E61R mutations.
1) Material and Methods
Cloning of M3$^-$-RM2-M2$^+$ and M3$^-$-RM2-M2$^+_{G19S}$ Molecules into a Mammalian Expression Vector
The methodology is exactly the same as the one described in example 1 but the CCM2For primer was replaced by the CCM2ForE8K primer (5'-AAGCAGAGCTCTCTG-GCTAACTAGAGAACCCACTGCTTACTGGCTTATCG ACCATGGCCAATACCAAATATAACAAAAAGTTCC-3': SEQ ID NO: 93).
2) Results
FIG. 21 shows the extrachromosomal SSA activity in CHO cells for the four single chain molecules M3-RM2-M2, M3-RM2-M2$_{G19S}$, M3$^-$-RM2-M2$^+$ and M3$^-$-RM2-M2$^+_{G19S}$, against the three RAG1.10, RAG1.10.2 and RAG1.10.3. Activity against the three targets is represented as a percentage of the activity of the initial M2/M3 heterodimer against these same three targets. The four single chain proteins have homodimer activities (against the RAG1.10.2 and RAG1.10.3 targets) equivalent to the background level. FIG. 21 shows also that the G19S mutation is essential to the single chain molecule activity as only the two single chain proteins carrying the G19S mutation present a RAG1.10 target cleavage activity equivalent or even greater than the M2/M3 heterodimer activity

EXAMPLE 6

RAG1 Single Chain Molecules Induce High Levels of Gene Targeting in CHO-K1 Cells To further assess the cleavage activity of the two single chain molecules M3-RM2-M2$_{G19S}$ (SEQ ID NO: 95 encoded by the nucleotide sequence SEQ ID NO: 94) and M3$^-$-RM2-M2$^+_{G19S}$ (SEQ ID NO: 97 encoded by the nucleotide sequence SEQ ID NO: 96), a chromosomal reporter system in CHO cells was used (FIG. 22). In this system a single-copy LacZ gene driven by the CMV promoter is interrupted by the RAG1.10 sequence and is thus non-functional. The transfection of the cell line with plasmids coding for RAG1 single chain meganucleases and a LacZ repair plasmid allows the restoration of a functional LacZ gene by homologous recombination. It has previously been shown that double-strand breaks can induce homologous recombination; therefore the frequency with which the LacZ gene is repaired is indicative of the cleavage efficiency of the genomic RAG1.10 target site.
1) Material and Methods
Chromosomal Assay in CHO-K1 Cells
CHO-K1 cell lines harbouring the reporter system were seeded at a density of $2 \times 10^5$ cells per 10 cm dish in complete medium (Kaighn's modified F-12 medium (F12-K), supplemented with 2 mM L-glutamine, penicillin (100 UI/ml), streptomycin (100 µg/ml), amphotericin B (Fongizone) (0.25 µg/ml) (INVITROGEN-LIFE SCIENCE) and 10% FBS (SIGMA-ALDRICH CHIMIE). The next day, cells were transfected with Polyfect transfection reagent (QIAGEN). Briefly, 2 µg of lacz repair matrix vector was co-transfected with various amounts of meganucleases expression vectors. After 72 hours of incubation at 37° C., cells were fixed in 0.5% glutaraldehyde at 4° C. for 10 min, washed twice in 100 mM phosphate buffer with 0.02% NP40 and stained with the following staining buffer (10 mM Phosphate buffer, 1 mM MgCl$_2$, 33 mM K hexacyanoferrate (III), 33 mM K hexacyanoferrate (II), 0.1% (v/v) X-Gal). After, an overnight incubation at 37° C., plates were examined under a light microscope and the number of LacZ positive cell clones counted. The frequency of LacZ repair is expressed as the number of LacZ+ foci divided by the number of transfected cells ($5 \times 10^5$) and corrected by the transfection efficiency.
2) Results
FIG. 22 shows that the two single chain molecules M3-RM2-M2$_{G19S}$ and M3$^-$-RM2-M2$^+_{G19S}$ can induce high level of gene targeting in CHO cells. They even increase the gene correction frequency by a 3.5 fold factor in comparison with the initial M2/M3 heterodimer.

EXAMPLE 7

Making of a RAG1 Single Chain Molecule with Different N- and C-Terminal Endings for Both Subunits Using the M2-RM2-M3 RAG1 single chain molecule, new single chain constructs with different N- and C-terminal endings for both subunits were engineered. These new constructs could allow to pinpoint the best possible position of the linker joining the two I-CreI derived mutants. The N-terminal of I-CreI consists in a 6 residues loop followed by the LAGL-IDADG α-helix starting at residue K7. In the I-CreI structure (PDB code 1G9Y), the last 10 C-terminal residues are not visible because probably disordered. In the structure, the C-terminus ends at residue D153 with the helix α6 covering residues 145 to 150. So several single chain constructs were made where the N-terminus of the M2 or M3 mutant begins with the residue M1, N2 or N6 and C-terminus ends at different positions, respectively S145, L152, S156 and K160. Activity of these different RAG1 single chain constructs was monitored using the previously described yeast screening assay (see example 1).
1) Material and Methods
a) Cloning of Truncated Versions of the M2 Mutant in the Yeast Expression Vector
Cloning of the RAG1 M2-RM2-M3 single chain requires first to get the M2 mutant cloned in the yeast expression vector (pCLS0542) (see Material and Methods of Example 3). To clone truncated versions of the M2 mutant, several PCR reactions were performed with different primers couples:

CreNter6/CreCter, CreNter/CreCter160, CreNter/CreCter156, CreNter/CreCter152, CreNter/CreCter145. Sequences of the different primers are listed in the table H below. The different PCR fragments were then digested with the restriction enzymes NcoI and EagI, and ligated into the pCLS0542 vector also digested with NcoI and EagI. The clones were then sequenced. The truncated versions of the M2 mutant are respectively: M2 (6-163), M2 (1-160), M2 (1-156), M2 (1-152) and M2 (1-145), where the numbers indicate the I-CreI residues contained in the M2 mutant coding sequence.

b) Cloning of a RAG1 Single Chain Molecule with Different Endings for Both Subunits Different PCR reactions were performed on the M3 mutant in the I-CreI CLS version. Each PCR reaction uses one forward primer and one reverse primer. There are two possible forward primers (RM2 and RM2N2) and five possible reverse primers (CreCterR60, Cre160R60, Cre156R60, Cre152R60 and Cre145R60). The forward primers allow to obtain a M3 coding sequence beginning at residue N6 or N2 and the reverse primers allow to obtain a M3 coding sequence ending respectively at residues P163, K160, S156, L152 and S145. The different PCR fragments were purified and digested by EagI and SacI and each PCR fragment was ligated into the yeast expression vector for one of the M2 mutants described above also digested with EagI and SacI. After sequencing of the clones, all possible single chain molecules in the yeast expression vector were obtained.

TABLE II

Primers sequences

| Primer Name | Sequence (SEQ ID NO: 79 to 92) |
|---|---|
| CreNter | 5'-acaggccatggccaataccaaatataacaaag-3' |
| CreNter6 | 5'-acaggccatggccaacaaagagttcctgctgtacctg-3' |
| CreCter | 5'-gattgacggccgccggggaggatttcttctt-3' |
| CreCter160 | 5'-gattgacggccgctttcttcttctcgctcaggctgtc-3' |
| CreCter156 | 5'-gattgacggccgcgctcaggctgtccaggacagcacg-3' |
| CreCter152 | 5'-gattgacggccgccaggacagcacgaacggtttcaga-3' |
| CreCter145 | 5'-gattgacggccgcagaagtggttttacgcgtcttaga-3' |
| RM2 | 5'-tatcggccggtggatctgataagtataatcaggctctgtctaaatacaaccaagcactgtccaagtacaatcaggccctgtctggtggaggcggttccaacaaagagttcctgctgtatcttgctggattt-3' |
| RM2N2 | 5'-tatcggccggtggatctgataagtataatcaggctctgtctaaatacaaccaagcactgtccaagtacaatcaggccctgtctggtggaggcggttccaacaccaagtacaacaaagagttcctgctgtat-3' |
| CreCterR60 | 5'-tagacgagctcctaaggagaggacttttcttctcag-3' |
| Cre160R60 | 5'-tagacgagctcctactttttcttctcagagaggtcatc-3' |
| Cre156R60 | 5'-tagacgagctcctaagagaggtcatccagaactgccct-3' |

TABLE II-continued

Primers sequences

| Primer Name | Sequence (SEQ ID NO: 79 to 92) |
|---|---|
| Cre152R60 | 5'-tagacgagctcctacagaactgccctcacagtctcaga-3' |
| Cre145R60 | 5'-tagacgagctcctaagaggtggttttctggtcttgga-3' |

2) Results

Starting from the RAG1 M2-RM2-M3 single chain molecule, four new single chain molecules were built where the N-Terminal M2 mutant was truncated at its C-terminus. These proteins are called SCtr1, SCtr2, SCtr3 and SCtr4 and correspond to single chain molecules, where the M2 mutant sequence ends respectively at residue 145, 152, 156 and 160. These four molecules as well as the initial M2-RM2-M3 single chain were tested for cleavage toward the three RAG1.10, RAG1.10.2 and RAG1.10.3 targets using our yeast screening assay. FIG. 23 shows that SCtr1 is inactive against the three targets and that the three other truncated versions of the single chain cleave the RAG1.10 target and slightly the RAG1.10.2 target. This result suggests that residues 145 to 152 of the M2 mutant that form the helix α6 are necessary to the single chain activity.

EXAMPLE 8

Gene Targeting at the Endogenous Rag1 Locus in Human Cells

To further validate the cleavage activity of engineered single-chain Rag1 meganucleases, their ability to stimulate homologous recombination at the endogenous human RAG1 locus was evaluated (FIG. 24). Cells were transfected with mammalian expression plasmids for one of two single chain molecules M3-RM2-M2$_{G19S}$ (SEQ ID NO: 95) and M3$^-$-RM2-M2$^+_{G19S}$ (SEQ ID NO: 97) and the donor repair plasmid pCLS1969 (FIG. 25) containing 1.7 kb of exogenous DNA sequence flanked by two sequences, 2 kb and 1.2 kb in length, homologous to the human RAG1 locus. Cleavage of the native RAG1 gene by the meganuclease yields a substrate for homologous recombination, which may use the donor repair plasmid containing 1.7 kb of exogenous DNA flanked by homology arms as a repair matrix. Thus, the frequency with which targeted integration occurs at the RAG1 locus is indicative of the cleavage efficiency of the genomic RAG1.10 target site.

1) Materials and Methods a) Meganuclease Expression Plasmids

Figure 6:
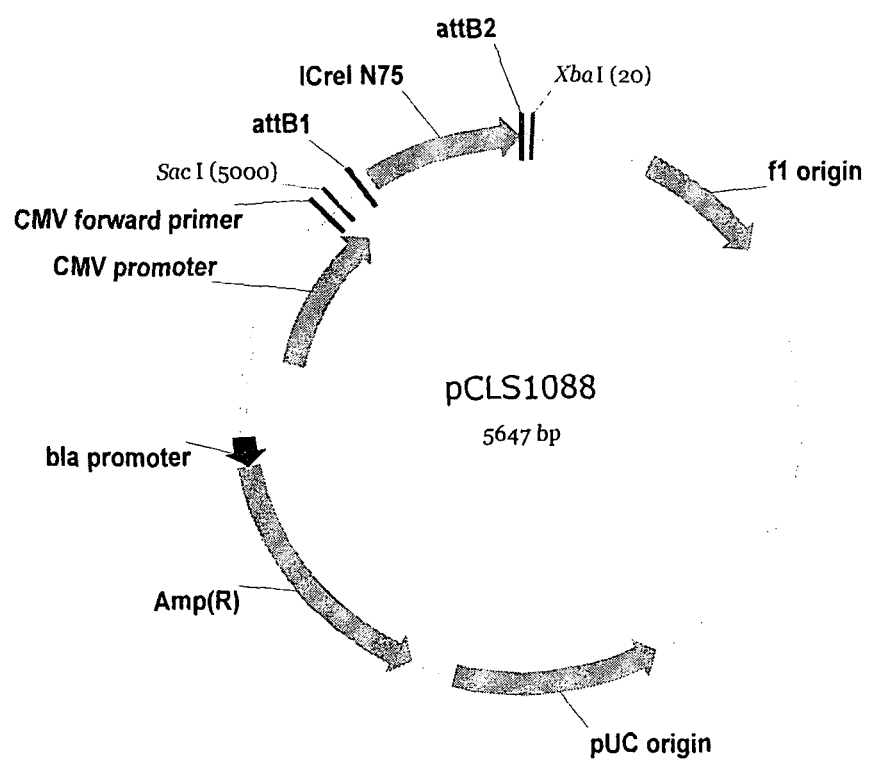
FIG. 6 represents the map of pCLS1088, a plasmid for expression of meganucleases in mammalian cells.

The Rag1 meganucleases used in this example are M3-RM2-M2$_{G19S}$ (SEQ ID NO: 95) and M3$^-$-RM2-M2$^+_{G19S}$ (SEQ ID NO: 97) cloned in a mammalian expression vector, pCLS1088 (FIG. 6).

b) Donor Repair Plasmid

The donor plasmid for gene targeting experiments contains a PCR generated 2075 bp fragment of the RAG1 locus (position 36549341 to 36551416 on chromosome 11, NC_000011.8) as the left homology arm and a 1174 bp fragment of the RAG1 locus (position 36551436 to 36552610 on chromosome 11, NC_000011.8) as the right homology arm. An exogenous 1.8 kb DNA fragment containing an SV40 promoter, neomycin resistance gene and an IRES sequence was inserted in between the two homology arms using EcoRI and BamHI sites that were introduced during the PCR amplification of the RAG1 locus. The resulting plasmid is pCLS1969 (FIG. 25).

c) Rag1 Gene Targeting Experiments

Human embryonic kidney 293H cells (Invitrogen) were plated at a density of $1 \times 10^6$ cells per 10 cm dish in complete medium (DMEM supplemented with 2 mM L-glutamine, penicillin (100 UI/ml), streptomycin (100 µg/ml), amphotericin B (Fongizone) (0.25 µg/ml) (Invitrogen-Life Science) and 10% FBS). The next day, cells were transfected with Lipofectamine 2000 transfection reagent (Invitrogen) according to the supplier's protocol. Briefly, 2 µg of the donor plasmid was co-transfected with 3 µg of single-chain meganuclease expression vectors. After 72 hours of incubation at 37° C., cells were trypsinized and plated in complete medium at 10 cells per well in a 96-well plate or at 200 cells in a 10 cm plate. Individual clones were subsequently picked from the 10 cm plate using a ClonePix robot (Genetix). Genomic DNA extraction was performed with the ZR-96 genomic DNA kit (Zymo research) according to the supplier's protocol.

d) PCR Analysis of Gene Targeting Events

The frequency of gene targeting was determined by PCR on genomic DNA using the primers F2-neo:5'-AGGATCTC-CTGTCATCTCAC-3' (SEQ ID NO: 98) and RagEx2-R12: 5'-CTTTCACAGTCCTGTACATCTTGT-3' (SEQ ID NO: 99) that result in a 2588 bp gene targeting specific PCR product (FIG. 26). The F2 primer is a forward primer located in the neomycin coding sequence. The R12 primer is a reverse primer located in the human RAG1 gene outside of the right homology arm of the donor repair plasmid.

e) Southern Blot Analysis

Southern blot analysis was performed with genomic DNA digested with HindIII and hybridized with an 830 bp RAG1 specific probe that is 3' of the right homology arm of the donor repair plasmid.

2) Results

Human embryonic kidney 293H cells were co-transfected with 2 vectors: a plasmid expressing one of the two single-chain Rag1 meganucleases and the donor repair plasmid pCLS1969 (FIG. 25). As a control for spontaneous recombination, 293H cells were also transfected with the donor repair plasmid alone. The cells were then plated at 10 cells per well in a 96-well microplate or plated in 10 cm dishes and individual clones subsequently picked. Genomic DNA derived from these cells was analyzed for gene targeting by PCR as described in Material and Methods. Results are presented in Table III. In the absence of meganuclease (repair plasmid alone), no PCR positive signal was detected among the 2,560 cells analyzed in pools of 10 cells or the 94 individual clones examined. In contrast, in the presence of the M3-RM2-M2$_{G19S}$ meganuclease, 11 positives were detected among the 2,560 cells analyzed in pools of 10 cells indicating a frequency of recombination of 0.4%. Among the 94 individual clones examined, none were positive. In the presence of M3$^-$-RM2-M2$^+_{G19S}$, 34 positive clones (1.4%) were detected among 2560 cells (in pools of 10) analyzed, and among the 94 individual clones analyzed, 4 were positive (4.3%). Southern blot analysis of these 4 individual clones indicates that three are consistent with a gene targeting event at the Rag 1 locus (FIG. 27). These results demonstrate that the two single chain molecules M3-RM2-M2$_{G19S}$ and M3$^-$-RM2-M2$^+_{G19S}$ are capable of inducing high levels of gene targeting at the endogenous Rag1 locus.

TABLE III

Frequency of gene targeting events at the Rag1 locus in human 293H cells

| Meganuclease | Cells per well | PCR+ events | Gene targeting frequency |
|---|---|---|---|
| M3-RM2-M2$_{G19S}$ | 10 | 11/2510 | 0.4% |
| M3-RM2-M2$_{G19S}$ | 1 | 0/94 | NA |
| M3$^-$-RM2-M2$^+_{G19S}$ | 10 | 34/2430 | 1.4% |
| M3$^-$-RM2-M2$^+_{G19S}$ | 1 | 4/94 | 4.3% |
| None | 10 | 0/2560 | NA |
| None | 1 | 0/94 | NA |

NA: not applicable

EXAMPLE 9

The I-CreI Derived Single Chain Meganuclease is Stable

1) Material and Methods a) Protein Expression and Purification

In order to coexpress the heterodimeric I-CreI derivatives each of the monomers ORF were cloned into CDFDuet-1 vector (NOVAGEN) with a 6×His tag or a Strep tag at the C-terminus and purification of the double tagged heterodimers was performed as described previously (P. Redondo et al., Nature, 2008, 456, 107-1). The single-chain M3-RM2-M2$_{G19S}$ protein sequences (example 4) with a His6 tag at the C-terminus was cloned in a pET24d(+) vector and expressed in E. coli Rosetta(DE3)pLysS cells (NOVAGEN) grown in LB plus kanamycin and chloramphenicol. Induction with IPTG for 5 h at 37° C. or for 15 h at 20° C. yielded high expression levels, however, after sonication in lysis buffer containing 50 mM sodium phosphate pH 8.0, 300 mM NaCl, 5% glycerol and protease inhibitors (Complete EDTA-free tablets, ROCHE) and ultracentrifugation at 20,000 g for 1 hour, the protein was found exclusively in the insoluble fraction as detected by a western blot with an anti-His antibody. Thus the protein was purified under denaturing conditions by first solubilizing it in lysis buffer plus 8 M urea. After clarification by ultracentrifugation (2 h at 40,000 g) the sample was applied onto a column packed with Q-Sepharose XL resin (GE Healthcare) equilibrated in the same buffer. This purification step separated all the nucleic acids (retained in the column) from the protein and improved the performance of the subsequent purification steps. The protein is recovered from the flowthrough by means of a Co$_{2+}$-loaded HiTrap Chelating HP 5 ml column (GE Healthcare) equilibrated in the lysis buffer plus 8 M urea. After sample loading and column washing the protein is eluted with the same buffer plus 0.5 M imidazol. Protein-rich fractions (determined by SDS-PAGE) were collected and refolded by a 20 fold dilution (drop by drop) into 20 mM sodium phosphate pH 6.0 300 mM NaCl at 4° C. (final protein concentration of 0.13 mg/ml). The refolded protein was loaded onto a 5 ml HiTrap heparin column equilibrated in the same buffer and eluted with a gradient to 1 M NaCl. The fractions with pure protein were pooled, concentrated up to 1.4 mg/ml (35.6 nM, determined by absorbance at 280 nm) and were either used immediately or flash frozen in liquid nitrogen and stored at −80° C.

b) Biochemical and Biophysical Characterization of Proteins

Circular dichroism (CD) measurements were performed on a Jasco J-810 spectropolarimeter using a 0.2 cm path length quartz cuvette adm 10-4 µM protein solutions in phosphate saline buffers. Equilibrium unfolding was induced increasing temperature at a rate of 1° C./min (using a programmable Peltier thermoelectric). Analytical gel filtration chromatography was performed at room temperature with an ÄKTA FPLC system (GE) using a Superdex 200 10/300GL column in 20 mM sodium phosphate buffer pH 6.0 1 M NaCl. A sample of 100 µL of SC-v3v2G19S constructs at a concentration of 0.3 mg/ml was injected and eluted at a flow rate of 0.2 ml/min. The column was calibrated with blue dextran (excluded volume) and molecular weight markers from 17 to 670 kDa (BioRad).

2) Results

The protein identity was confirmed by mass spectrometry which showed that the initial methionine was absent in the purified polypeptide chain. The purified proteins were found to be folded with a similar structure as the wild type by circular dichroism and NMR and to be dimeric in solution by analytical ultracentrifugation and gel filtration. The structure and stability of the single-chain molecule were very similar to those of the heterodimeric variants and this molecule appeared to be monomeric in solution (FIG. 28).

EXAMPLE 10

The I-CreI Derived Single Chain Meganuclease is not Toxic

1) Material and Methods
a) Cell Survival Assay

CHO-K1 cell line was seeded at a density of $2 \times 10^5$ cells per 10 cm dish. The next day, various quantity of meganuclease expression vectors and a constant amount of plasmid coding for GFP were co-transfected into CHO-K1 cells in 10 cm plate. GPF expression was monitored at days 1 and 6 post-transfection by flow cytometry (Guava EasyCyte, Guava technologies). Cell survival corrected by the transfection efficiency measured at day 1 was calculated as a ratio of [(meganuclease transfected cell expressing GFP at day 6)/(meganuclease transfected cell expressing GFP at day 1)]/[(control transfected cell expressing GFP at day 6)/(control transfected cell expressing GFP at day 1).

b) γH2AX Immunocytochemistry

For γH2AX immunocytochemistry, CHO-K1 cells were transfected by Polyfect reagent (Qiagen) with a 4 µg of DNA mixture containing different amounts of plasmid encoding a HA-tagged meganuclease and completed to 4 µg with empty vector as a stuffer. 48 h after transfection, cells were fixed with 2% of paraformaldehyde for 30 minutes and permeabilized with 0.5% Triton for 5 nm at RT. After wash, cells were incubated with PBS/triton 0.3% buffer containing 10% normal goat serum (NGS) and 3% BSA for 1 hour to block nonspecific staining. Cells were then incubated one hour at RT with anti-γH2AX (Upstate: 1/10000) and anti-HA (Santa Cruz: 1/100) antibodies diluted in PBS/triton 0.3% with 3% BSA and 10% NGS followed by 1 hour incubation with secondary antibody Alexa Fluor 488 goat antimouse (Invitrogen-Molecular probes: 1/1000) and Alexa Fluor 546 goat anti-rabbit diluted in PBS/triton 0.3%, 3% BSA, and 10% NGS. After incubation with 1 µg/ml 4,6-diamino-2-phenyindole (DAPI; Sigma), coverslips were mounted and the γH2AX foci were visualized in transfected (HA positive) cells by fluorescent microscopy.

2) Results

Toxicity is a major issue for DSB-induced recombination technology, particularly for therapeutic applications, for which the activity/toxicity ratio is of major concern. The toxicity of the RAG1 meganucleases (examples 4 and 5) was evaluated in a cell survival assay, as previously described (M. L. Maeder et al., Mol. Cell., 2003, 31, 2952-). The link between efficacy and toxicity was investigated by adapting this assay for use with the CHO-K1 cells used for the activity dose response assay. At the active dose (the dose at which the meganucleases displayed their maximum level of activity FIG. 29A), toxicity was barely detectable, regardless of the meganuclease used (FIG. 29B). However, the M2/M3 heterodimer displayed significant toxicity at high doses, which was partly alleviated by the obligatory heterodimer design. The single-chain design also represented an improvement, as the best version reproduced the pattern obtained with I-SceI. The toxicity of sequence-specific endonucleases is usually attributed to off-site cleavage, which can result in mutations, deletions, translocations and other gross genomic alterations (M. H. Porteus, D. Carroll, Nat. Biotechnol., 2005, 23, 967-). The off-site cleavage, was evaluated by monitoring the formation of phosphorylated H2AX histone (γ-H2AX) foci. γ-H2AX focus formation is one of the first responses of the cell to DNA double-strand breaks (DSBs) and provides a convenient means of monitoring DSBs in living cells (E. P. Rogakou et al., J. Biol. Chem., 1998, 273, 5858). CHO-K1 cells were transfected with two doses of meganuclease expression vectors (active dose and 10-fold excess). The M2(G19S)/M3(G19S) heterodimer was used as a control for non toxicity, as this molecule was completely inactive in the assays. At the active dose, no signal above background was observed, regardless of the meganuclease variant used, consistent with published results (P. Redondo et al., Nature, 2008, 456, 107-. In accordance with previous data, the M2(G19S)/M3 heterodimer, when used at ten times the active dose, induced significant levels of focus formation, as illustrated in FIG. 29C, whereas use of either the obligatory heterodimer or the single-chain design minimized off-site cleavage. Ultimately, the signals obtained with the single-chain molecule M3⁻RM2-M2$^+_{G19S}$ were similar to those obtained with the I-SceI meganuclease.

The invention claimed is:

1. A single-chain I-CreI meganuclease comprising two domains in the orientation N-terminal toward C-terminal joined by a peptidic linker, wherein:
   (a) each domain, derived from a parent I-CreI monomer, comprises a portion of said parent I-CreI monomer said portion extending at least from the beginning of the first alpha helix ($\alpha_1$) to the end of the C-terminal loop of I-CreI and including successively: the $\alpha_1\beta_1\beta_2\alpha_2\beta_3\beta_4\alpha_3$ core domain, the $\alpha_4$ and $\alpha_5$ helices and the C-terminal loop of I-CreI, and
   (b) the two domains are joined by a peptidic linker which allows said two domains to fold as a I-CreI dimer that is able to bind and cleave a chimeric DNA target comprising one different half of each parent homodimeric I-CreI meganuclease target sequence, wherein said peptidic linker is selected from the group consisting of the sequences SEQ ID NO: 2 to 12 and 14 to 19.

2. The single-chain I-CreI meganuclease according to claim 1, wherein
   (i) the N-terminal domain starts at position 1, 2, 3, 4, 5, or 6 of I-CreI (SEQ ID NO:20) and/or the C-terminal domain starts at position 2, 3, 4, 5, or 6 of I-CreI (SEQ ID NO:20); and
   (ii) the N-terminal and/or C-terminal domain(s) terminate(s) at position 145 of I-CreI (SEQ ID NO:20); or
   (iii) the N-terminal and/or C-terminal domain(s) further include(s) at least the $\alpha_6$ helix of I-CreI (SEQ ID NO:20); or
   (iv) the N-terminal and/or C-terminal domain(s) terminate(s) at position 152, 156, 160 or 163 of I-CreI (SEQ ID NO:20).

3. The single-chain I-CreI meganuclease according to claim 1, wherein each domain comprises mutations at positions 26 to 40 and/or 44 to 77 of I-CreI (SEQ ID NO:20), said single-chain I-CreI meganuclease being able to cleave a non-palindromic DNA target sequence.

4. The single-chain I-CreI meganuclease according to claim 1, wherein at least one domain comprises a mutation at positions 137 to 143 of I-CreI (SEQ ID NO:20) that modifies the specificity of the single-chain I-CreI meganuclease towards the I-CreI site of SEQ ID NO:21.

5. The single-chain I-CreI meganuclease according to claim 1, which comprises one or more mutations that impair the formation of functional homodimers from the two domains.

6. The single-chain I-CreI meganuclease according to claim 5, wherein each domain comprises at least one mutation, selected from the group consisting of:
   K7E or K7D and E8K or E8R; F54G or F54A and L97F or L97W; K96D or K96E and E61R or E611K; R51D or R51E and D137R or D137K of SEQ ID NO: 20, respectively for the first and the second domain.

7. The single-chain I-CreI meganuclease according to claim 6, wherein one domain comprises the substitution of the lysine residues at positions 7 and 96 of SEQ ID NO: 20 by an acidic amino acid and the other domain comprises the substitution of the glutamic acid residues at positions 8 and 61 of SEQ ID NO: 20 by a basic amino acid.

8. The single chain I-CreI meganuclease according to claim 1 wherein one domain comprises the G19S mutation of SEQ ID NO: 20.

9. The single-chain I-CreI meganuclease according to claim 1, which comprises the sequence SEQ ID NO: 95 or 97.

10. A pharmaceutical composition comprising at least one single-chain I-CreI meganuclease of claim 1.

* * * * *

SEQUENCE LISTING

```
<160> NUMBER OF SEQ ID NOS: 99

<210> SEQ ID NO 1
<211> LENGTH: 11
<212> TYPE: PRT
<213> ORGANISM: artificial sequence
<220> FEATURE:
<223> OTHER INFORMATION: I-DmoI loop

<400> SEQUENCE: 1

Met Leu Glu Arg Ile Arg Leu Phe Asn Met Arg
1               5                   10
```

```
<210> SEQ ID NO 2
<211> LENGTH: 32
<212> TYPE: PRT
<213> ORGANISM: artificial sequence
<220> FEATURE:
<223> OTHER INFORMATION: RM2 peptide linker

<400> SEQUENCE: 2

Ala Ala Gly Gly Ser Asp Lys Tyr Asn Gln Ala Leu Ser Lys Tyr Asn
1               5                   10                  15

Gln Ala Leu Ser Lys Tyr Asn Gln Ala Leu Ser Gly Gly Gly Gly Ser
                20                  25                  30

<210> SEQ ID NO 3
<211> LENGTH: 22
<212> TYPE: PRT
<213> ORGANISM: artificial sequence
<220> FEATURE:
<223> OTHER INFORMATION: L1 peptide linker

<400> SEQUENCE: 3

Ala Ala Gly Gly Gly Gly Ser Gly Gly Gly Gly Ser Gly Gly Gly Gly
1               5                   10                  15

Ser Gly Gly Gly Gly Ser
                20

<210> SEQ ID NO 4
<211> LENGTH: 35
<212> TYPE: PRT
<213> ORGANISM: artificial sequence
<220> FEATURE:
<223> OTHER INFORMATION: YPP peptide linker

<400> SEQUENCE: 4

Ala Ala Gly Lys Ser Ser Asp Ser Lys Gly Ile Asp Leu Thr Asn Val
1               5                   10                  15

Thr Leu Pro Asp Thr Pro Thr Tyr Ser Lys Ala Ala Ser Asp Ala Ile
                20                  25                  30

Pro Pro Ala
        35

<210> SEQ ID NO 5
<211> LENGTH: 31
<212> TYPE: PRT
<213> ORGANISM: artificial sequence
<220> FEATURE:
<223> OTHER INFORMATION: AOL peptide linker

<400> SEQUENCE: 5

Ala Ala Gly Leu Glu Tyr Pro Gln Ala Pro Tyr Ser Ser Pro Pro Gly
1               5                   10                  15

Pro Pro Cys Cys Ser Gly Ser Ser Gly Ser Ala Gly Cys Ser
                20                  25                  30

<210> SEQ ID NO 6
<211> LENGTH: 30
<212> TYPE: PRT
<213> ORGANISM: artificial sequence
<220> FEATURE:
<223> OTHER INFORMATION: CXT peptide linker

<400> SEQUENCE: 6

Ala Ala Gly Leu Ser Tyr His Tyr Ser Asn Gly Gly Ser Pro Thr Ser
```

```
                1               5                  10                  15
Asp Gly Pro Ala Leu Gly Gly Ile Ser Asp Gly Gly Ala Thr
            20                  25                  30

<210> SEQ ID NO 7
<211> LENGTH: 27
<212> TYPE: PRT
<213> ORGANISM: artificial sequence
<220> FEATURE:
<223> OTHER INFORMATION: BQY peptide linker

<400> SEQUENCE: 7

Ala Ala Gly Asp Ser Ser Val Ser Asn Ser Glu His Ile Ala Pro Leu
1               5                   10                  15

Ser Leu Pro Ser Ser Pro Pro Ser Val Gly Ser
            20                  25

<210> SEQ ID NO 8
<211> LENGTH: 25
<212> TYPE: PRT
<213> ORGANISM: artificial sequence
<220> FEATURE:
<223> OTHER INFORMATION: VSG peptide linker

<400> SEQUENCE: 8

Ala Ala Gly Ala Ser Gln Gly Cys Lys Pro Leu Ala Leu Pro Glu Leu
1               5                   10                  15

Leu Thr Glu Asp Ser Tyr Asn Thr Asp
            20                  25

<210> SEQ ID NO 9
<211> LENGTH: 24
<212> TYPE: PRT
<213> ORGANISM: artificial sequence
<220> FEATURE:
<223> OTHER INFORMATION: BYM peptide linker

<400> SEQUENCE: 9

Ala Ala Gly Asn Pro Ile Pro Gly Leu Asp Glu Leu Gly Val Gly Asn
1               5                   10                  15

Ser Asp Ala Ala Ala Pro Gly Thr
            20

<210> SEQ ID NO 10
<211> LENGTH: 23
<212> TYPE: PRT
<213> ORGANISM: artificial sequence
<220> FEATURE:
<223> OTHER INFORMATION: MCJ peptide linker

<400> SEQUENCE: 10

Ala Ala Gly Ala Pro Thr Glu Cys Ser Pro Ser Ala Leu Thr Gln Pro
1               5                   10                  15

Pro Ser Ala Ser Gly Ser Leu
            20

<210> SEQ ID NO 11
<211> LENGTH: 27
<212> TYPE: PRT
<213> ORGANISM: artificial sequence
<220> FEATURE:
<223> OTHER INFORMATION: GSmid peptide linker

<400> SEQUENCE: 11
```

```
Ala Ala Gly Gly Gly Gly Ser Gly Gly Gly Ser Gly Gly Gly Gly
1               5                  10                 15

Ser Gly Gly Gly Gly Ser Gly Gly Gly Ser
            20                  25
```

<210> SEQ ID NO 12
<211> LENGTH: 17
<212> TYPE: PRT
<213> ORGANISM: artificial sequence
<220> FEATURE:
<223> OTHER INFORMATION: Gsshort peptide linker

<400> SEQUENCE: 12

```
Ala Ala Gly Gly Gly Gly Ser Gly Gly Gly Gly Ser Gly Gly Gly
1               5                  10                 15

Ser
```

<210> SEQ ID NO 13
<211> LENGTH: 12
<212> TYPE: PRT
<213> ORGANISM: artificial sequence
<220> FEATURE:
<223> OTHER INFORMATION: GSxshort peptide linker

<400> SEQUENCE: 13

```
Ala Ala Gly Gly Gly Gly Ser Gly Gly Gly Gly Ser
1               5                  10
```

<210> SEQ ID NO 14
<211> LENGTH: 17
<212> TYPE: PRT
<213> ORGANISM: artificial sequence
<220> FEATURE:
<223> OTHER INFORMATION: PPR peptide linker

<400> SEQUENCE: 14

```
Ala Ala Gly Gln Val Thr Ser Ala Ala Gly Pro Ala Thr Val Pro Ser
1               5                  10                 15

Gly
```

<210> SEQ ID NO 15
<211> LENGTH: 19
<212> TYPE: PRT
<213> ORGANISM: artificial sequence
<220> FEATURE:
<223> OTHER INFORMATION: SBA1 peptide linker

<400> SEQUENCE: 15

```
Ala Ala Gly Gly Ser Pro Leu Lys Pro Ser Ala Pro Lys Ile Pro Ile
1               5                  10                 15

Gly Gly Ser
```

<210> SEQ ID NO 16
<211> LENGTH: 33
<212> TYPE: PRT
<213> ORGANISM: artificial sequence
<220> FEATURE:
<223> OTHER INFORMATION: SBA2 peptide linker

<400> SEQUENCE: 16

```
Ala Ala Gly Gly Ser Pro Leu Lys Pro Ser Ala Pro Lys Ile Pro Ile
1               5                  10                 15

Gly Gly Ser Pro Leu Lys Pro Ser Ala Pro Lys Ile Pro Ile Gly Gly
            20                  25                 30
```

Ser

<210> SEQ ID NO 17
<211> LENGTH: 15
<212> TYPE: PRT
<213> ORGANISM: artificial sequence
<220> FEATURE:
<223> OTHER INFORMATION: LP1 peptide linker

<400> SEQUENCE: 17

Ala Ala Gly Gly Ser Pro Leu Ser Lys Pro Ile Pro Gly Gly Ser
1               5                   10                  15

<210> SEQ ID NO 18
<211> LENGTH: 25
<212> TYPE: PRT
<213> ORGANISM: artificial sequence
<220> FEATURE:
<223> OTHER INFORMATION: LP2 peptide linker

<400> SEQUENCE: 18

Ala Ala Gly Gly Ser Pro Leu Ser Lys Pro Ile Pro Gly Gly Ser Pro
1               5                   10                  15

Leu Ser Lys Pro Ile Pro Gly Gly Ser
            20                  25

<210> SEQ ID NO 19
<211> LENGTH: 31
<212> TYPE: PRT
<213> ORGANISM: artificial sequence
<220> FEATURE:
<223> OTHER INFORMATION: RM1 peptide linker

<400> SEQUENCE: 19

Ala Ala Gly Gly Ser Asp Lys Tyr Asn Gln Ala Leu Ser Glu Arg Arg
1               5                   10                  15

Ala Tyr Val Val Ala Asn Asn Leu Val Ser Gly Gly Gly Ser
            20                  25                  30

<210> SEQ ID NO 20
<211> LENGTH: 163
<212> TYPE: PRT
<213> ORGANISM: Chlamydomonas reinhardtii

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 21
<211> LENGTH: 22
<212> TYPE: DNA
<213> ORGANISM: artificial sequence
<220> FEATURE:
<223> OTHER INFORMATION: C1221 target

<400> SEQUENCE: 21
caaaacgtcg tacgacgttt tg                                          22

<210> SEQ ID NO 22
<211> LENGTH: 492
<212> TYPE: DNA
<213> ORGANISM: artificial sequence
<220> FEATURE:
<223> OTHER INFORMATION: I-CreI wt coding sequence
<220> FEATURE:
<221> NAME/KEY: CDS
<222> LOCATION: (1)..(492)

<400> SEQUENCE: 22 atg aat acc aaa tat aac aaa gag ttc ctg ctg tac ctg gcc ggc ttt    48
Met Asn Thr Lys Tyr Asn Lys Glu Phe Leu Leu Tyr Leu Ala Gly Phe
1               5                   10                  15 gtg gac ggt gac ggt agc atc atc gct cag att aaa cca aac cag tct    96
Val Asp Gly Asp Gly Ser Ile Ile Ala Gln Ile Lys Pro Asn Gln Ser
                20                  25                  30 tat aag ttt aaa cat cag cta agc ttg acc ttt cag gtg act caa aag   144
Tyr Lys Phe Lys His Gln Leu Ser Leu Thr Phe Gln Val Thr Gln Lys
            35                  40                  45 acc cag cgc cgt tgg ttt ctg gac aaa cta gtg gat gaa att ggc gtt   192
Thr Gln Arg Arg Trp Phe Leu Asp Lys Leu Val Asp Glu Ile Gly Val
        50                  55                  60 ggt tac gta cgt gat cgc gga tcc gtt tcc aac tac atc tta agc gaa   240
Gly Tyr Val Arg Asp Arg Gly Ser Val Ser Asn Tyr Ile Leu Ser Glu
65                  70                  75                  80 atc aag ccg ctg cac aac ttc ctg act caa ctg cag ccg ttt ctg aaa   288
Ile Lys Pro Leu His Asn Phe Leu Thr Gln Leu Gln Pro Phe Leu Lys
                85                  90                  95 ctg aaa cag aaa cag gca aac ctg gtt ctg aaa att atc gaa cag ctg   336
Leu Lys Gln Lys Gln Ala Asn Leu Val Leu Lys Ile Ile Glu Gln Leu
            100                 105                 110 ccg tct gca aaa gaa tcc ccg gac aaa ttc ctg gaa gtt tgt acc tgg   384
Pro Ser Ala Lys Glu Ser Pro Asp Lys Phe Leu Glu Val Cys Thr Trp
        115                 120                 125 gtg gat cag att gca gct ctg aac gat tct aag acg cgt aaa acc act   432
Val Asp Gln Ile Ala Ala Leu Asn Asp Ser Lys Thr Arg Lys Thr Thr
    130                 135                 140 tct gaa acc gtt cgt gct gtg ctg gac agc ctg agc gag aag aag aaa   480
Ser Glu Thr Val Arg Ala Val Leu Asp Ser Leu Ser Glu Lys Lys Lys
145                 150                 155                 160 tcc tcc ccg tag                                                   492
Ser Ser Pro

<210> SEQ ID NO 23
```

-continued

```
<211> LENGTH: 163
<212> TYPE: PRT
<213> ORGANISM: artificial sequence
<220> FEATURE:
<223> OTHER INFORMATION: Synthetic Construct

<400> SEQUENCE: 23

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asn Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 24
<211> LENGTH: 492
<212> TYPE: DNA
<213> ORGANISM: artificial sequence
<220> FEATURE:
<223> OTHER INFORMATION: I-CreI CLS
<220> FEATURE:
<221> NAME/KEY: CDS
<222> LOCATION: (1)..(492)

<400> SEQUENCE: 24 atg aac acc aag tac aac aaa gag ttc ctg ctg tat ctt gct gga ttt    48
Met Asn Thr Lys Tyr Asn Lys Glu Phe Leu Leu Tyr Leu Ala Gly Phe
1               5                   10                  15 gtg gat ggt gat ggc tcc atc att gct cag ata aaa cca aat caa tct    96
Val Asp Gly Asp Gly Ser Ile Ile Ala Gln Ile Lys Pro Asn Gln Ser
            20                  25                  30 tac aag ttc aaa cac cag ctc tcc ttg gcc ttt caa gtc act cag aag   144
Tyr Lys Phe Lys His Gln Leu Ser Leu Ala Phe Gln Val Thr Gln Lys
        35                  40                  45 aca caa aga agg tgg ttc ttg gac aaa ttg gtt gat gag att ggt gtg   192
Thr Gln Arg Arg Trp Phe Leu Asp Lys Leu Val Asp Glu Ile Gly Val
    50                  55                  60 ggc tat gtc aga gac aga ggc tct gtg tca gac tac atc ctg tct gaa   240
Gly Tyr Val Arg Asp Arg Gly Ser Val Ser Asp Tyr Ile Leu Ser Glu
65                  70                  75                  80 att aag cct ctt cat aac ttt ctc acc caa ctg caa ccc ttc ttg aag   288
Ile Lys Pro Leu His Asn Phe Leu Thr Gln Leu Gln Pro Phe Leu Lys
                85                  90                  95 ctc aaa cag aag caa gca aat ctg gtt ttg aaa atc atc tgg aga ctg   336
Leu Lys Gln Lys Gln Ala Asn Leu Val Leu Lys Ile Ile Trp Arg Leu
```

| | | | | | | | | | | | | | | |
|---|---|---|---|---|---|---|---|---|---|---|---|---|---|---|
| | | | | 100 | | | | 105 | | | | 110 | | |
| cca | tct | gcc | aag | gag | tcc | cct | gac | aag | ttt | ctt | gaa | gtg | tgt | act | tgg | 384 |
| Pro | Ser | Ala | Lys | Glu | Ser | Pro | Asp | Lys | Phe | Leu | Glu | Val | Cys | Thr | Trp |
| | | 115 | | | | | 120 | | | | | 125 | | |

```
           100                 105                 110
cca tct gcc aag gag tcc cct gac aag ttt ctt gaa gtg tgt act tgg      384
Pro Ser Ala Lys Glu Ser Pro Asp Lys Phe Leu Glu Val Cys Thr Trp
        115                 120                 125 gtg gat cag att gct gcc ttg aat gac tcc aag acc aga aaa acc acc      432
Val Asp Gln Ile Ala Ala Leu Asn Asp Ser Lys Thr Arg Lys Thr Thr
130                 135                 140 tct gag act gtg agg gca gtt ctg gat agc ctc tct gag aag aaa aag      480
Ser Glu Thr Val Arg Ala Val Leu Asp Ser Leu Ser Glu Lys Lys Lys
145                 150                 155                 160 tcc tct cct tag                                                      492
Ser Ser Pro <210> SEQ ID NO 25
<211> LENGTH: 163
<212> TYPE: PRT
<213> ORGANISM: artificial sequence
<220> FEATURE:
<223> OTHER INFORMATION: Synthetic Construct

<400> SEQUENCE: 25

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 26
<211> LENGTH: 22
<212> TYPE: DNA
<213> ORGANISM: artificial sequence
<220> FEATURE:
<223> OTHER INFORMATION: XPC4.1 target

<400> SEQUENCE: 26
cgagatgtca cacagaggta cg                                              22

<210> SEQ ID NO 27
<211> LENGTH: 22
<212> TYPE: DNA
<213> ORGANISM: artificial sequence
<220> FEATURE:
<223> OTHER INFORMATION: 10GAG_P target
```

```
<400> SEQUENCE: 27
cgagacgtcg tacgacgtct cg                                        22

<210> SEQ ID NO 28
<211> LENGTH: 22
<212> TYPE: DNA
<213> ORGANISM: artificial sequence
<220> FEATURE:
<223> OTHER INFORMATION: 10GTA_P target

<400> SEQUENCE: 28
cgtaacgtcg tacgacgtta cg                                        22

<210> SEQ ID NO 29
<211> LENGTH: 22
<212> TYPE: DNA
<213> ORGANISM: artificial sequence
<220> FEATURE:
<223> OTHER INFORMATION: 5TCT_P target

<400> SEQUENCE: 29
caaaactctg tacagagttt tg                                        22

<210> SEQ ID NO 30
<211> LENGTH: 22
<212> TYPE: DNA
<213> ORGANISM: artificial sequence
<220> FEATURE:
<223> OTHER INFORMATION: C3 target

<400> SEQUENCE: 30
cgagatgtcg tacgacatct cg                                        22

<210> SEQ ID NO 31
<211> LENGTH: 22
<212> TYPE: DNA
<213> ORGANISM: artificial sequence
<220> FEATURE:
<223> OTHER INFORMATION: C4 target

<400> SEQUENCE: 31
cgtacctctg tacagaggta cg                                        22

<210> SEQ ID NO 32
<211> LENGTH: 22
<212> TYPE: DNA
<213> ORGANISM: artificial sequence
<220> FEATURE:
<223> OTHER INFORMATION: 10CAT_P target

<400> SEQUENCE: 32
ccatacgtcg tacgacgtat gg                                        22

<210> SEQ ID NO 33
<211> LENGTH: 22
<212> TYPE: DNA
<213> ORGANISM: artificial sequence
<220> FEATURE:
<223> OTHER INFORMATION: 5CTT_P target

<400> SEQUENCE: 33
caaaaccttg tacaaggttt tg                                        22

<210> SEQ ID NO 34
<211> LENGTH: 22
```

```
<212> TYPE: DNA
<213> ORGANISM: artificial sequence
<220> FEATURE:
<223> OTHER INFORMATION: HprCH3 target

<400> SEQUENCE: 34
cgagatgtca tgaaagagat gg                                              22

<210> SEQ ID NO 35
<211> LENGTH: 22
<212> TYPE: DNA
<213> ORGANISM: artificial sequence
<220> FEATURE:
<223> OTHER INFORMATION: HprCH3.3 target

<400> SEQUENCE: 35
cgagatgtcg tacgacatct cg                                              22

<210> SEQ ID NO 36
<211> LENGTH: 22
<212> TYPE: DNA
<213> ORGANISM: artificial sequence
<220> FEATURE:
<223> OTHER INFORMATION: HprCH3.4 target

<400> SEQUENCE: 36
ccatctcttg tacaagagat gg                                              22

<210> SEQ ID NO 37
<211> LENGTH: 22
<212> TYPE: DNA
<213> ORGANISM: artificial sequence
<220> FEATURE:
<223> OTHER INFORMATION: 10GTT_P target

<400> SEQUENCE: 37
cgttacgtcg tacgacgtaa cg                                              22

<210> SEQ ID NO 38
<211> LENGTH: 22
<212> TYPE: DNA
<213> ORGANISM: artificial sequence
<220> FEATURE:
<223> OTHER INFORMATION: 5CAG_P target

<400> SEQUENCE: 38
caaaaccagg tacctggttt tg                                              22

<210> SEQ ID NO 39
<211> LENGTH: 22
<212> TYPE: DNA
<213> ORGANISM: artificial sequence
<220> FEATURE:
<223> OTHER INFORMATION: 10TGG_P target

<400> SEQUENCE: 39
ctggacgtcg tacgacgtcc ag                                              22

<210> SEQ ID NO 40
<211> LENGTH: 22
<212> TYPE: DNA
<213> ORGANISM: artificial sequence
<220> FEATURE:
<223> OTHER INFORMATION: 5GAG_P target

<400> SEQUENCE: 40
```

```
caaaacgagg tacctcgttt tg                                            22

<210> SEQ ID NO 41
<211> LENGTH: 22
<212> TYPE: DNA
<213> ORGANISM: artificial sequence
<220> FEATURE:
<223> OTHER INFORMATION: RAG1.10 target

<400> SEQUENCE: 41
tgttctcagg tacctcagcc ag                                            22

<210> SEQ ID NO 42
<211> LENGTH: 22
<212> TYPE: DNA
<213> ORGANISM: artificial sequence
<220> FEATURE:
<223> OTHER INFORMATION: RAG1.10.2 target

<400> SEQUENCE: 42
tgttctcagg tacctgagaa ca                                            22

<210> SEQ ID NO 43
<211> LENGTH: 22
<212> TYPE: DNA
<213> ORGANISM: artificial sequence
<220> FEATURE:
<223> OTHER INFORMATION: RAG1.10.3 target

<400> SEQUENCE: 43
ctggctgagg tacctcagcc ag                                            22

<210> SEQ ID NO 44
<211> LENGTH: 26
<212> TYPE: DNA
<213> ORGANISM: artificial sequence
<220> FEATURE:
<223> OTHER INFORMATION: primer

<400> SEQUENCE: 44
gcaactttag tgctgacaca tacagg                                        26

<210> SEQ ID NO 45
<211> LENGTH: 33
<212> TYPE: DNA
<213> ORGANISM: artificial sequence
<220> FEATURE:
<223> OTHER INFORMATION: primer

<400> SEQUENCE: 45
ctggtgtttg aacttgtgag attgatttgg ttt                                33

<210> SEQ ID NO 46
<211> LENGTH: 33
<212> TYPE: DNA
<213> ORGANISM: artificial sequence
<220> FEATURE:
<223> OTHER INFORMATION: primer

<400> SEQUENCE: 46
aaaccaaatc aatctcacaa gttcaaacac cag                                33

<210> SEQ ID NO 47
<211> LENGTH: 24
<212> TYPE: DNA
<213> ORGANISM: artificial sequence
```

```
<220> FEATURE:
<223> OTHER INFORMATION: primer

<400> SEQUENCE: 47
acaaccttga ttggagactt gacc                                              24

<210> SEQ ID NO 48
<211> LENGTH: 37
<212> TYPE: DNA
<213> ORGANISM: artificial sequence
<220> FEATURE:
<223> OTHER INFORMATION: primer

<400> SEQUENCE: 48
tagacgagct cctaaggaga ggactttttc ttctcag                                37

<210> SEQ ID NO 49
<211> LENGTH: 98
<212> TYPE: DNA
<213> ORGANISM: artificial sequence
<220> FEATURE:
<223> OTHER INFORMATION: primer

<400> SEQUENCE: 49
tatcggccgg tggcggagga tctggcggcg gtggatccgg tggtggaggc tccggaggag       60
gtggctctaa caaagagttc ctgctgtatc ttgctgga                               98

<210> SEQ ID NO 50
<211> LENGTH: 140
<212> TYPE: DNA
<213> ORGANISM: artificial sequence
<220> FEATURE:
<223> OTHER INFORMATION: primer

<400> SEQUENCE: 50
tatcggccgg taaatcttcc gattccaagg gtattgatct gactaatgtt actctgcctg       60 ataccctac ttattccaaa gctgcctctg atgctattcc tccagctaac aaagagttcc       120
tgctgtatct tgctggattt                                                   140

<210> SEQ ID NO 51
<211> LENGTH: 125
<212> TYPE: DNA
<213> ORGANISM: artificial sequence
<220> FEATURE:
<223> OTHER INFORMATION: primer

<400> SEQUENCE: 51
tatcggccgg tctggagtat caggctcctt actcttcccc tccaggtcct ccttgttgct       60
ccggttcctc tggctcctct gctggttgtt ctaacaaaga gttcctgctg tatcttgctg       120
gattt                                                                   125

<210> SEQ ID NO 52
<211> LENGTH: 125
<212> TYPE: DNA
<213> ORGANISM: artificial sequence
<220> FEATURE:
<223> OTHER INFORMATION: primer

<400> SEQUENCE: 52
tatcggccgg tctgtcctat cattattcta atggtggctc ccctacttct gatggtccag       60
ctctgggtgg catttctgat ggtggcgcta ctaacaaaga gttcctgctg tatcttgctg       120
``` gattt                                                              125

<210> SEQ ID NO 53
<211> LENGTH: 116
<212> TYPE: DNA
<213> ORGANISM: artificial sequence
<220> FEATURE:
<223> OTHER INFORMATION: primer

<400> SEQUENCE: 53
tatcggccgg tgattcctct gtttctaatt ccgagcacat tgctcctctg tctctgcctt      60
cctctcctcc atctgttggt tctaacaaag agttcctgct gtatcttgct ggattt         116

<210> SEQ ID NO 54
<211> LENGTH: 110
<212> TYPE: DNA
<213> ORGANISM: artificial sequence
<220> FEATURE:
<223> OTHER INFORMATION: primer

<400> SEQUENCE: 54
tatcggccgg tgcttctcag ggttgtaaac ctctggctct gcctgagctg cttactgagg      60
attcttataa tactgataac aaagagttcc tgctgtatct tgctggattt                110

<210> SEQ ID NO 55
<211> LENGTH: 107
<212> TYPE: DNA
<213> ORGANISM: artificial sequence
<220> FEATURE:
<223> OTHER INFORMATION: primer

<400> SEQUENCE: 55
tatcggccgg taatcctatt cctggtctgg atgagctggg tgttggcaac tctgatgctg      60
ccgctcctgg cactaacaaa gagttcctgc tgtatcttgc tggattt                   107

<210> SEQ ID NO 56
<211> LENGTH: 104
<212> TYPE: DNA
<213> ORGANISM: artificial sequence
<220> FEATURE:
<223> OTHER INFORMATION: primer

<400> SEQUENCE: 56
tatcggccgg tgctcctact gagtgttctc cttccgctct gacccagcct ccatccgctt      60
ctggttccct gaacaaagag ttcctgctgt atcttgctgg attt                      104

<210> SEQ ID NO 57
<211> LENGTH: 116
<212> TYPE: DNA
<213> ORGANISM: artificial sequence
<220> FEATURE:
<223> OTHER INFORMATION: primer

<400> SEQUENCE: 57
tatcggccgg tggaggcggt tctggaggcg gtggctctgg tggaggcggt tccggtggag      60
gcggatctgg tggaggcggt tctaacaaag agttcctgct gtatcttgct ggattt         116

<210> SEQ ID NO 58
<211> LENGTH: 86
<212> TYPE: DNA
<213> ORGANISM: artificial sequence
<220> FEATURE:
<223> OTHER INFORMATION: primer

<400> SEQUENCE: 58
tatcggccgg tggaggcggt tctggaggcg gtggctctgg tggaggcggt tccaacaaag    60
agttcctgct gtatcttgct ggattt                                        86

<210> SEQ ID NO 59
<211> LENGTH: 71
<212> TYPE: DNA
<213> ORGANISM: artificial sequence
<220> FEATURE:
<223> OTHER INFORMATION: primer

<400> SEQUENCE: 59
tatcggccgg tggaggcggt tctggaggcg gtggctctaa caaagagttc ctgctgtatc    60
ttgctggatt t                                                        71

<210> SEQ ID NO 60
<211> LENGTH: 86
<212> TYPE: DNA
<213> ORGANISM: artificial sequence
<220> FEATURE:
<223> OTHER INFORMATION: primer

<400> SEQUENCE: 60
tatcggccgg tcaggttact tctgctgccg gtcctgctac tgttccatct ggtaacaaag    60
agttcctgct gtatcttgct ggattt                                        86

<210> SEQ ID NO 61
<211> LENGTH: 92
<212> TYPE: DNA
<213> ORGANISM: artificial sequence
<220> FEATURE:
<223> OTHER INFORMATION: primer

<400> SEQUENCE: 61
tatcggccgg tggatctcct ctgaagcctt ctgccccaaa gattcctata ggtggctcca    60
acaaagagtt cctgctgtat cttgctggat tt                                 92

<210> SEQ ID NO 62
<211> LENGTH: 134
<212> TYPE: DNA
<213> ORGANISM: artificial sequence
<220> FEATURE:
<223> OTHER INFORMATION: primer

<400> SEQUENCE: 62
tatcggccgg tggatctcct ctgaagcctt ctgccccaaa gattcctata ggtggctccc    60
cactgaaacc ttccgcacct aaaatcccaa ttggtggctc taacaaagag ttcctgctgt   120
atcttgctgg attt                                                    134

<210> SEQ ID NO 63
<211> LENGTH: 80
<212> TYPE: DNA
<213> ORGANISM: artificial sequence
<220> FEATURE:
<223> OTHER INFORMATION: primer

<400> SEQUENCE: 63
tatcggccgg tggatctcct ctgtctaaac caattccagg cggttccaac aaagagttcc    60
tgctgtatct tgctggattt                                               80

```
<210> SEQ ID NO 64
<211> LENGTH: 110
<212> TYPE: DNA
<213> ORGANISM: artificial sequence
<220> FEATURE:
<223> OTHER INFORMATION: primer

<400> SEQUENCE: 64
tatcggccgg tggatctcct ctgtctaaac caattccagg cggttcccca ctgtcaaagc      60
caatccctgg cggttctaac aaagagttcc tgctgtatct tgctggattt                110

<210> SEQ ID NO 65
<211> LENGTH: 128
<212> TYPE: DNA
<213> ORGANISM: artificial sequence
<220> FEATURE:
<223> OTHER INFORMATION: primer

<400> SEQUENCE: 65
tatcggccgg tggatctgat aagtataatc aggctctgtc tgagcgtcgc gcctacgttg      60
tcgccaataa cctggtttcc ggtggaggcg gttccaacaa agagttcctg ctgtatcttg     120
ctggattt                                                             128

<210> SEQ ID NO 66
<211> LENGTH: 131
<212> TYPE: DNA
<213> ORGANISM: artificial sequence
<220> FEATURE:
<223> OTHER INFORMATION: primer

<400> SEQUENCE: 66
tatcggccgg tggatctgat aagtataatc aggctctgtc taaatacaac caagcactgt      60
ccaagtacaa tcaggccctg tctggtggag gcggttccaa caaagagttc ctgctgtatc     120
ttgctggatt t                                                         131

<210> SEQ ID NO 67
<211> LENGTH: 35
<212> TYPE: DNA
<213> ORGANISM: artificial sequence
<220> FEATURE:
<223> OTHER INFORMATION: primer

<400> SEQUENCE: 67
gcaatgatgg agccatcaga atccacaaat ccagc                                35

<210> SEQ ID NO 68
<211> LENGTH: 35
<212> TYPE: DNA
<213> ORGANISM: artificial sequence
<220> FEATURE:
<223> OTHER INFORMATION: primer

<400> SEQUENCE: 68
gctggatttg tggattctga tggctccatc attgc                                35

<210> SEQ ID NO 69
<211> LENGTH: 34
<212> TYPE: DNA
<213> ORGANISM: artificial sequence
<220> FEATURE:
<223> OTHER INFORMATION: primer

<400> SEQUENCE: 69
```
aataccaaat ataacgaaga gttcctgctg tacc           34

<210> SEQ ID NO 70
<211> LENGTH: 33
<212> TYPE: DNA
<213> ORGANISM: artificial sequence
<220> FEATURE:
<223> OTHER INFORMATION: primer

<400> SEQUENCE: 70
aagatacagc aggaactttt tgttagagcc acc            33

<210> SEQ ID NO 71
<211> LENGTH: 33
<212> TYPE: DNA
<213> ORGANISM: artificial sequence
<220> FEATURE:
<223> OTHER INFORMATION: primer

<400> SEQUENCE: 71
ggtggctcta acaaaaagtt cctgctgtat ctt            33

<210> SEQ ID NO 72
<211> LENGTH: 32
<212> TYPE: DNA
<213> ORGANISM: artificial sequence
<220> FEATURE:
<223> OTHER INFORMATION: primer

<400> SEQUENCE: 72
caggtacagc aggaactttt tgttatattt gg             32

<210> SEQ ID NO 73
<211> LENGTH: 34
<212> TYPE: DNA
<213> ORGANISM: artificial sequence
<220> FEATURE:
<223> OTHER INFORMATION: primer

<400> SEQUENCE: 73
accaaatata acaaaaagtt cctgctgtac ctgg           34

<210> SEQ ID NO 74
<211> LENGTH: 33
<212> TYPE: DNA
<213> ORGANISM: artificial sequence
<220> FEATURE:
<223> OTHER INFORMATION: primer

<400> SEQUENCE: 74
aagatacagc aggaactctt cgttagagcc acc            33

<210> SEQ ID NO 75
<211> LENGTH: 33
<212> TYPE: DNA
<213> ORGANISM: artificial sequence
<220> FEATURE:
<223> OTHER INFORMATION: primer

<400> SEQUENCE: 75
ggtggctcta acgaagagtt cctgctgtat ctt            33

<210> SEQ ID NO 76
<211> LENGTH: 84
<212> TYPE: DNA

<213> ORGANISM: artificial sequence
<220> FEATURE:
<223> OTHER INFORMATION: primer

<400> SEQUENCE: 76
aagcagagct ctctggctaa ctagagaacc cactgcttac tggcttatcg accatggcca    60
ataccaaata taacaaagag ttcc    84

<210> SEQ ID NO 77
<211> LENGTH: 36
<212> TYPE: DNA
<213> ORGANISM: artificial sequence
<220> FEATURE:
<223> OTHER INFORMATION: primer

<400> SEQUENCE: 77
ctgctctaga ctaaggagag gactttttct tctcag    36

<210> SEQ ID NO 78
<211> LENGTH: 38
<212> TYPE: DNA
<213> ORGANISM: artificial sequence
<220> FEATURE:
<223> OTHER INFORMATION: primer

<400> SEQUENCE: 78
tagacgagct cctacgggga ggatttcttc ttctcgct    38

<210> SEQ ID NO 79
<211> LENGTH: 32
<212> TYPE: DNA
<213> ORGANISM: artificial sequence
<220> FEATURE:
<223> OTHER INFORMATION: primer

<400> SEQUENCE: 79
acaggccatg gccaatacca aatataacaa ag    32

<210> SEQ ID NO 80
<211> LENGTH: 37
<212> TYPE: DNA
<213> ORGANISM: artificial sequence
<220> FEATURE:
<223> OTHER INFORMATION: primer

<400> SEQUENCE: 80
acaggccatg gccaacaaag agttcctgct gtacctg    37

<210> SEQ ID NO 81
<211> LENGTH: 31
<212> TYPE: DNA
<213> ORGANISM: artificial sequence
<220> FEATURE:
<223> OTHER INFORMATION: primer

<400> SEQUENCE: 81
gattgacggc cgccggggag gatttcttct t    31

<210> SEQ ID NO 82
<211> LENGTH: 37
<212> TYPE: DNA
<213> ORGANISM: artificial sequence
<220> FEATURE:
<223> OTHER INFORMATION: primer

<400> SEQUENCE: 82
gattgacggc cgctttcttc ttctcgctca ggctgtc    37

<210> SEQ ID NO 83
<211> LENGTH: 37
<212> TYPE: DNA
<213> ORGANISM: artificial sequence
<220> FEATURE:
<223> OTHER INFORMATION: primer

<400> SEQUENCE: 83
gattgacggc cgcgctcagg ctgtccagga cagcacg    37

<210> SEQ ID NO 84
<211> LENGTH: 37
<212> TYPE: DNA
<213> ORGANISM: artificial sequence
<220> FEATURE:
<223> OTHER INFORMATION: primer

<400> SEQUENCE: 84
gattgacggc cgccaggaca gcacgaacgg tttcaga    37

<210> SEQ ID NO 85
<211> LENGTH: 37
<212> TYPE: DNA
<213> ORGANISM: artificial sequence
<220> FEATURE:
<223> OTHER INFORMATION: primer

<400> SEQUENCE: 85
gattgacggc cgcagaagtg gttttacgcg tcttaga    37

<210> SEQ ID NO 86
<211> LENGTH: 131
<212> TYPE: DNA
<213> ORGANISM: artificial sequence
<220> FEATURE:
<223> OTHER INFORMATION: primer

<400> SEQUENCE: 86
tatcggccgg tggatctgat aagtataatc aggctctgtc taaatacaac caagcactgt    60
ccaagtacaa tcaggccctg tctggtggag gcggttccaa caaagagttc ctgctgtatc    120
ttgctggatt t    131

<210> SEQ ID NO 87
<211> LENGTH: 131
<212> TYPE: DNA
<213> ORGANISM: artificial sequence
<220> FEATURE:
<223> OTHER INFORMATION: primer

<400> SEQUENCE: 87
tatcggccgg tggatctgat aagtataatc aggctctgtc taaatacaac caagcactgt    60
ccaagtacaa tcaggccctg tctggtggag gcggttccaa caccaagtac aacaaagagt    120
tcctgctgta t    131

<210> SEQ ID NO 88
<211> LENGTH: 37
<212> TYPE: DNA
<213> ORGANISM: artificial sequence
<220> FEATURE:
<223> OTHER INFORMATION: primer

<400> SEQUENCE: 88
tagacgagct cctaaggaga ggactttttc ttctcag    37

<210> SEQ ID NO 89
<211> LENGTH: 38
<212> TYPE: DNA
<213> ORGANISM: artificial sequence
<220> FEATURE:
<223> OTHER INFORMATION: primer

<400> SEQUENCE: 89
tagacgagct cctactttt cttctcagag aggtcatc    38

<210> SEQ ID NO 90
<211> LENGTH: 38
<212> TYPE: DNA
<213> ORGANISM: artificial sequence
<220> FEATURE:
<223> OTHER INFORMATION: primer

<400> SEQUENCE: 90
tagacgagct cctaagagag gtcatccaga actgccct    38

<210> SEQ ID NO 91
<211> LENGTH: 38
<212> TYPE: DNA
<213> ORGANISM: artificial sequence
<220> FEATURE:
<223> OTHER INFORMATION: primer

<400> SEQUENCE: 91
tagacgagct cctacagaac tgccctcaca gtctcaga    38

<210> SEQ ID NO 92
<211> LENGTH: 38
<212> TYPE: DNA
<213> ORGANISM: artificial sequence
<220> FEATURE:
<223> OTHER INFORMATION: primer

<400> SEQUENCE: 92
tagacgagct cctaagaggt ggtttttctg gtcttgga    38

<210> SEQ ID NO 93
<211> LENGTH: 84
<212> TYPE: DNA
<213> ORGANISM: artificial sequence
<220> FEATURE:
<223> OTHER INFORMATION: CCM2ForE8K primer

<400> SEQUENCE: 93
aagcagagct ctctggctaa ctagagaacc cactgcttac tggcttatcg accatggcca    60
ataccaaata taacaaaaag ttcc    84

<210> SEQ ID NO 94
<211> LENGTH: 1065
<212> TYPE: DNA
<213> ORGANISM: artificial sequence
<220> FEATURE:
<223> OTHER INFORMATION: single chain M3-RM2-M2G19S coding sequence

<400> SEQUENCE: 94
atggccaata ccaaatataa caaagagttc ctgctgtacc tggccggctt tgtggacggt    60
gacggtagca tcatcgctca gattaatcca aaccagtctt ctaagtttaa acatcgtcta    120

```
cgtttgacct tttatgtgac tcaaaagacc cagcgccgtt ggtttctgga caaactagtg    180
gatgaaattg gcgttggtta cgtacgtgat tctggatccg tttcccagta cgttttaagc    240
gaaatcaagc cgctgcacaa cttcctgact caactgcagc cgtttctgaa actgaaacag    300
aaacaggcaa acctggttct gaaaattatc gaacagctgc cgtctgcaaa agaatccccg    360
gacaaattcc tggaagtttg tacctgggtg gatcagattg cagctctgaa cgattctaag    420
acgcgtaaaa ccacttctga aaccgttcgt gctgtgctgg acagcctgag cgggaagaag    480
aaatcctccc cggcggccgg tggatctgat aagtataatc aggctctgtc taaatacaac    540
caagcactgt ccaagtacaa tcaggccctg tctggtggag gcggttccaa caagagttc     600
ctgctgtatc ttgctggatt tgtggattct gatggctcca tcattgctca gataaaacca    660
cgtcaatcta acaagttcaa acaccagctc tccttgactt ttgcagtcac tcagaagaca    720
caaagaaggt ggttcttgga caaattggtt gatgagattg gtgtgggcta tgtctatgac    780
agtggctctg tgtcagacta ccgcctgtct gaaattaagc tcttcataa ctttctcacc     840
caactgcaac ccttcttgaa gctcaaacag aagcaagcaa atctggtttt gaaaatcatc    900
gagcaactgc catctgccaa ggagtcccct gacaagtttc ttgaagtgtg tacttgggtg    960
gatcagattg ctgccttgaa tgactccaag accagaaaaa ccacctctga gactgtgagg   1020
gcagttctgg atagcctctc tgagaagaaa agtcctctc cttag                    1065

<210> SEQ ID NO 95
<211> LENGTH: 354
<212> TYPE: PRT
<213> ORGANISM: artificial sequence
<220> FEATURE:
<223> OTHER INFORMATION: single chain M3-RM2-M2G19S

<400> SEQUENCE: 95

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Asn Pro Asn Gln
            20                  25                  30

Ser Ser Lys Phe Lys His Arg Leu Arg Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Gln Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Gly Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190
```

Gly Gly Gly Ser Asn Lys Glu Phe Leu Leu Tyr Leu Ala Gly Phe Val
            195                 200                 205
Asp Ser Asp Gly Ser Ile Ile Ala Gln Ile Lys Pro Arg Gln Ser Asn
210                 215                 220
Lys Phe Lys His Gln Leu Ser Leu Thr Phe Ala Val Thr Gln Lys Thr
225                 230                 235                 240
Gln Arg Arg Trp Phe Leu Asp Lys Leu Val Asp Glu Ile Gly Val Gly
                245                 250                 255
Tyr Val Tyr Asp Ser Gly Ser Val Ser Asp Tyr Arg Leu Ser Glu Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 96
<211> LENGTH: 1065
<212> TYPE: DNA
<213> ORGANISM: artificial sequence
<220> FEATURE:
<223> OTHER INFORMATION: single chain M3--RM2-M2+G19S coding sequence

<400> SEQUENCE: 96

```
atggccaata ccaaatataa cgaagagttc ctgctgtacc tggccggctt tgtggacggt      60
gacggtagca tcatcgctca gattaatcca aaccagtctt ctaagtttaa acatcgtcta     120
cgtttgacct tttatgtgac tcaaaagacc cagcgccgtt ggtttctgga caaactagtg     180
gatgaaattg gcgttggtta cgtacgtgat tctggatccg tttcccagta cgttttaagc     240
gaaatcaagc cgctgcacaa cttcctgact caactgcagc cgtttctgga actgaaacag     300
aaacaggcaa acctggttct gaaaattatc gaacagctgc cgtctgcaaa agaatccccg     360
gacaaattcc tggaagtttg tacctgggtg gatcagattg cagctctgaa cgattctaag     420
acgcgtaaaa ccacttctga accgttcgt gctgtgctgg acagcctgag cgggaagaag     480
aaatcctccc cggcggccgg tggatctgat aagtataatc aggctctgtc taaatacaac     540
caagcactgt ccaagtacaa tcaggccctg tctggtggag gcggttccaa caaaaagttc     600
ctgctgtatc ttgctggatt tgtggattct gatggctcca tcattgctca gataaaacca     660
cgtcaatcta acaagttcaa acaccagctc tccttgactt ttgcagtcac tcagaagaca     720
caaagaaggt ggttcttgga caaattggtt gataggattg gtgtgggcta tgtctatgac     780
agtggctctg tgtcagacta ccgcctgtct gaaattaagc ctcttcataa cttttctcacc     840
caactgcaac ccttcttgaa gctcaaacag aagcaagcaa atctggtttt gaaaatcatc     900
gagcaactgc catctgccaa ggagtcccct gacaagtttc ttgaagtgtg tacttgggtg     960
gatcagattg ctgccttgaa tgactccaag accagaaaaa ccacctctga gactgtgagg    1020
gcagttctgg atagcctctc tgagaagaaa agtcctctc cttag                     1065
```

<210> SEQ ID NO 97
<211> LENGTH: 354
<212> TYPE: PRT
<213> ORGANISM: artificial sequence
<220> FEATURE:
<223> OTHER INFORMATION: single chain M3--RM2-M2+G19S

<400> SEQUENCE: 97

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Asn Pro Asn Gln
            20                  25                  30

Ser Ser Lys Phe Lys His Arg Leu Arg Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Gln Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Gly Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Arg Gln Ser Asn
    210                 215                 220

Lys Phe Lys His Gln Leu Ser Leu Thr Phe Ala Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 98

```
<211> LENGTH: 20
<212> TYPE: DNA
<213> ORGANISM: artificial sequence
<220> FEATURE:
<223> OTHER INFORMATION: F2-neo primer

<400> SEQUENCE: 98
aggatctcct gtcatctcac                                              20

<210> SEQ ID NO 99
<211> LENGTH: 24
<212> TYPE: DNA
<213> ORGANISM: artificial sequence
<220> FEATURE:
<223> OTHER INFORMATION: RagEx2-R12 primer

<400> SEQUENCE: 99
ctttcacagt cctgtacatc ttgt                                         24
```